US010987161B2

(12) United States Patent
Shuman et al.

(10) Patent No.: US 10,987,161 B2
(45) Date of Patent: Apr. 27, 2021

(54) USER INTERFACE AND LOCK FEATURES FOR POSITIONING MULTIPLE COMPONENTS WITHIN A BODY

(71) Applicant: Spiration, Inc.—Olympus Respiratory America, Redmond, WA (US)

(72) Inventors: Brandon J. Shuman, Kirkland, WA (US); David H. Dillard, Grapeview, WA (US); Peter A. Lambe, Redmond, WA (US); Nathan Dale, Mill Creek, WA (US); Cassandra R. Saleira, Bothell, WA (US); Fan Zhang, Seattle, WA (US); Nicolas G. Hostein, Seattle, WA (US); Randall D. Mills, Sultan, WA (US); Christine N. Jurevicius, Issaquah, WA (US); Michael S. Smith, Sammamish, WA (US)

( * ) Notice: Subject to any disclaimer, the term of this patent is extended or adjusted under 35 U.S.C. 154(b) by 671 days.

(21) Appl. No.: 15/462,872

(22) Filed: Mar. 19, 2017

(65) Prior Publication Data
US 2018/0263681 A1     Sep. 20, 2018

Related U.S. Application Data

(60) Provisional application No. 62/311,226, filed on Mar. 21, 2016.

(51) Int. Cl.
*A61B 18/12*     (2006.01)
*A61B 18/14*     (2006.01)
*A61B 18/00*     (2006.01)

(52) U.S. Cl.
CPC .............. *A61B 18/1492* (2013.01); *A61B 2018/00196* (2013.01); *A61B 2018/00577* (2013.01);
(Continued)

(58) Field of Classification Search
CPC ...... A61B 18/1492; A61B 2018/00196; A61B 2018/00577; A61B 2018/00589;
(Continued)

(56) References Cited

U.S. PATENT DOCUMENTS

| 4,869,259 | A | | 9/1989 | Elkins | |
|---|---|---|---|---|---|
| 5,919,202 | A | * | 7/1999 | Yoon | ................ A61B 17/12013 606/139 |

(Continued)

OTHER PUBLICATIONS

International Search Report and Written Opinion of related Application PCT/US2017/023242.

*Primary Examiner* — Daniel W Fowler

(57) ABSTRACT

Disclosed embodiments include apparatuses, systems, and methods for positioning electrodes within a body. In an illustrative embodiment, an apparatus for slidably moving multiple features relative to a sheath inserted into a body and positioned relative to a reference point includes a primary actuator configured to move a primary electrode, a secondary actuator configured to move a secondary electrode, and a control mechanism. The control mechanism is configured to selectively prevent movement of at least one of the primary actuator based on a position of the secondary actuator and of the secondary actuator based on a position of the primary actuator and lock positions of the primary actuator and the secondary actuator.

17 Claims, 40 Drawing Sheets

(52) U.S. Cl.
CPC ........... *A61B 2018/00589* (2013.01); *A61B 2018/00982* (2013.01); *A61B 2018/126* (2013.01); *A61B 2018/1407* (2013.01); *A61B 2018/1427* (2013.01); *A61B 2018/1435* (2013.01); *A61B 2018/1475* (2013.01)

(58) Field of Classification Search
CPC .... A61B 2018/00982; A61B 2018/126; A61B 2018/1407; A61B 2018/1427; A61B 2018/1435; A61B 2018/1475
See application file for complete search history.

(56) References Cited

U.S. PATENT DOCUMENTS

| | | |
|---|---|---|
| 6,416,510 B1 | 7/2002 | Altman et al. |
| 6,749,604 B1 | 6/2004 | Eggers et al. |
| 7,357,798 B2 | 4/2008 | Sharps et al. |
| 7,419,488 B2 | 9/2008 | Ciarrocca et al. |
| 8,043,286 B2 | 10/2011 | Palanker et al. |
| 8,114,071 B2 | 2/2012 | Woloszko et al. |
| 8,361,066 B2 | 1/2013 | Long et al. |
| 9,539,012 B2 | 1/2017 | Landry et al. |
| 9,888,926 B2 | 2/2018 | Phan et al. |
| 2002/0091382 A1* | 7/2002 | Hooven ............ A61B 18/1445 606/41 |
| 2003/0028231 A1 | 2/2003 | Partridge et al. |
| 2003/0083682 A1* | 5/2003 | Heise ............... A61B 17/32006 606/169 |
| 2004/0059328 A1 | 3/2004 | Daniel et al. |
| 2005/0113827 A1* | 5/2005 | Dumbauld ......... A61B 18/1445 606/45 |
| 2009/0076412 A1* | 3/2009 | Rioux ............... A61B 10/0266 600/564 |
| 2009/0299362 A1 | 12/2009 | Long et al. |
| 2010/0004723 A1 | 1/2010 | Foster et al. |
| 2010/0256627 A1* | 10/2010 | Ma .................... A61B 18/1492 606/41 |
| 2010/0324637 A1 | 12/2010 | Trip et al. |
| 2012/0035474 A1 | 2/2012 | Deckman et al. |
| 2012/0053485 A1 | 3/2012 | Bloom |
| 2013/0190609 A1 | 7/2013 | Fischer |
| 2013/0204068 A1 | 8/2013 | Gnanashanmugam et al. |
| 2013/0226026 A1 | 8/2013 | Dillard et al. |
| 2013/0310823 A1 | 11/2013 | Gelfand et al. |
| 2014/0276764 A1* | 9/2014 | Shuman ............ A61B 18/1477 606/34 |
| 2015/0005769 A1 | 1/2015 | Klink et al. |
| 2016/0015451 A1 | 1/2016 | Shikhman |
| 2018/0206903 A1 | 7/2018 | Podany |

* cited by examiner

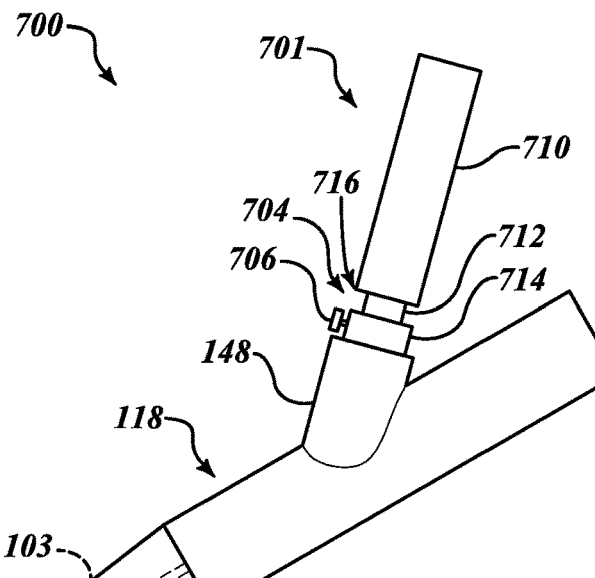
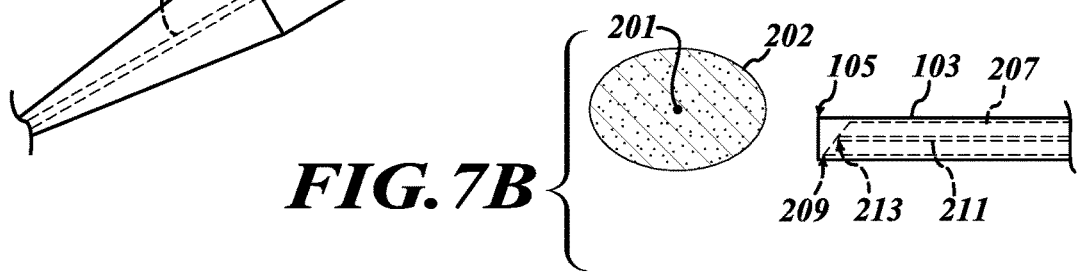
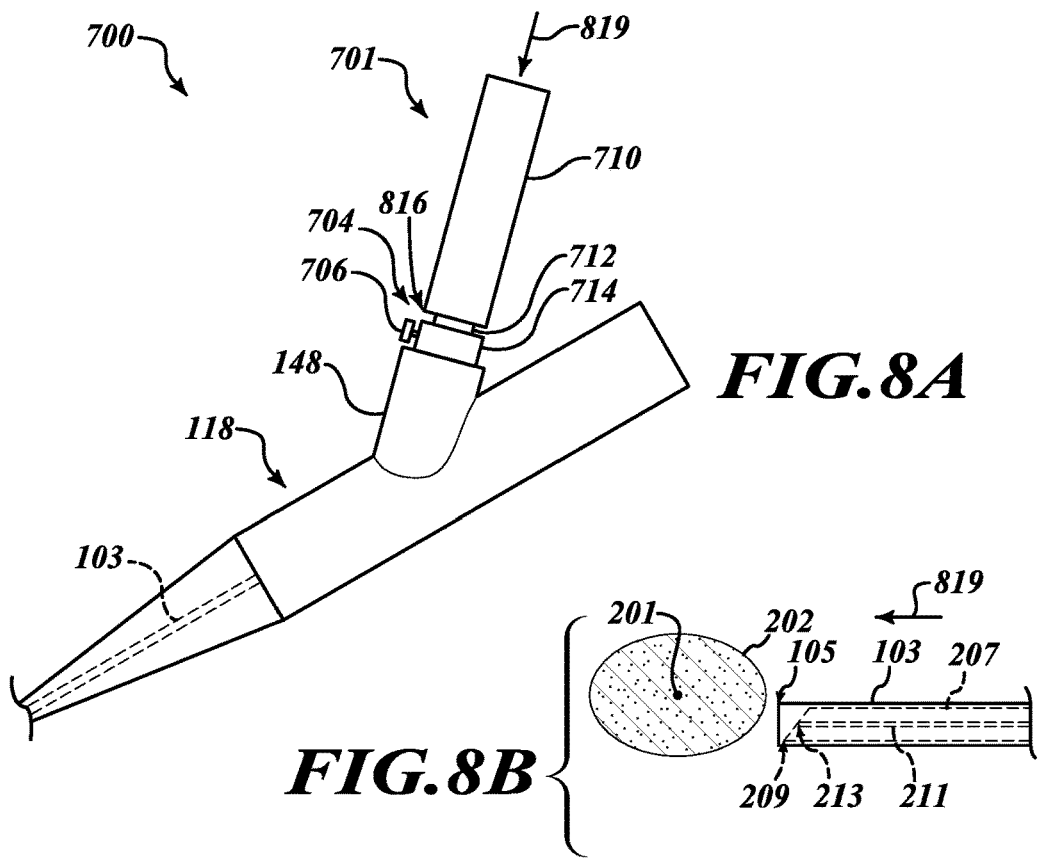
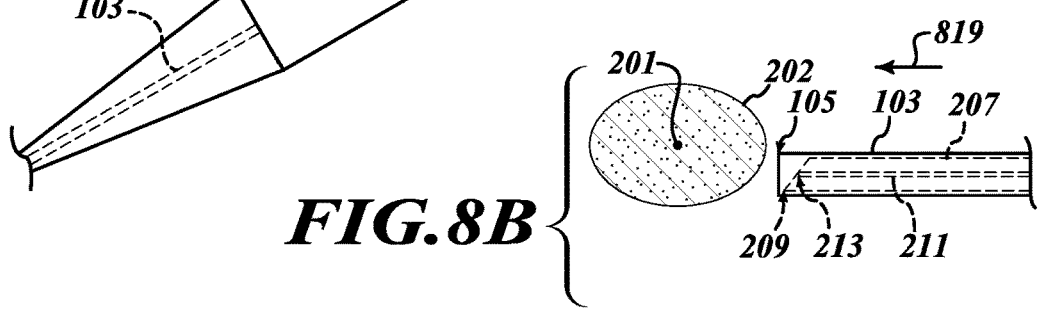

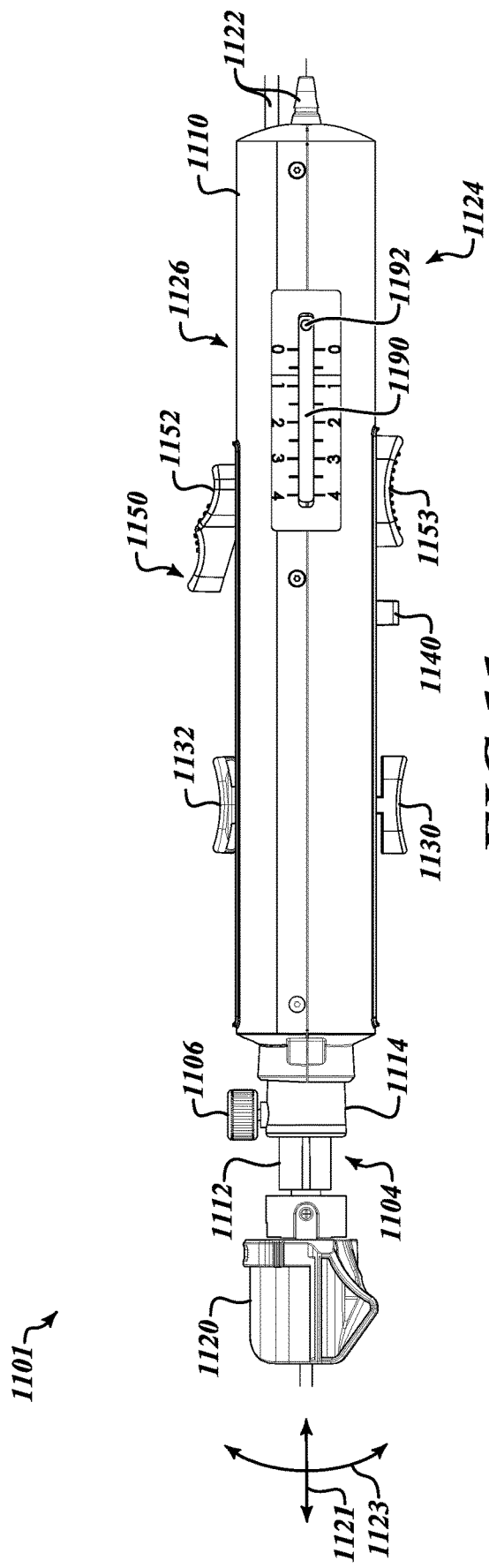

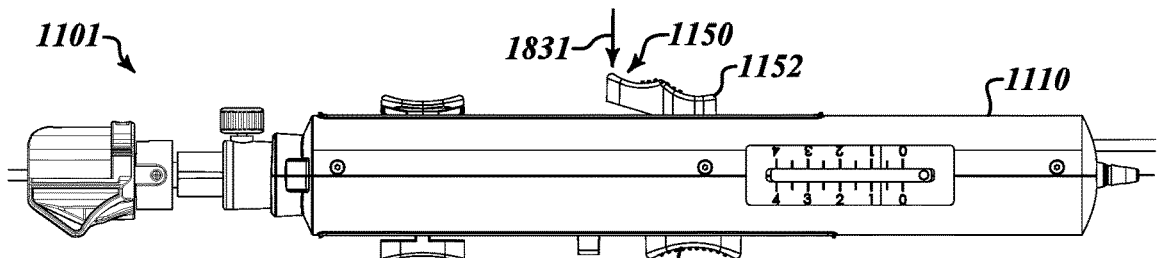
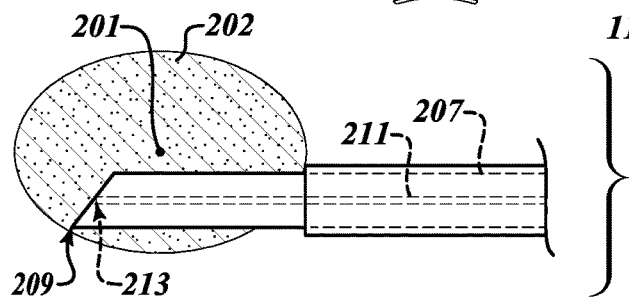
FIG.18A
FIG.18B
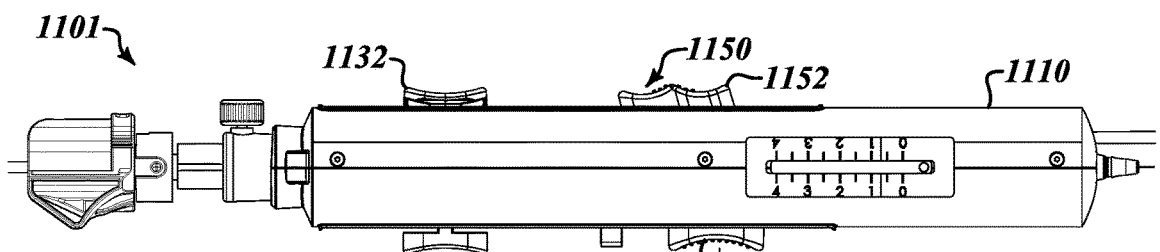
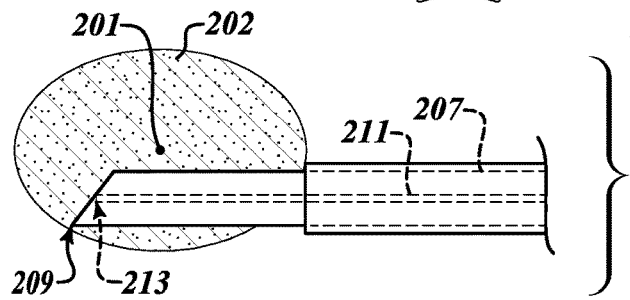
FIG.19A
FIG.19B
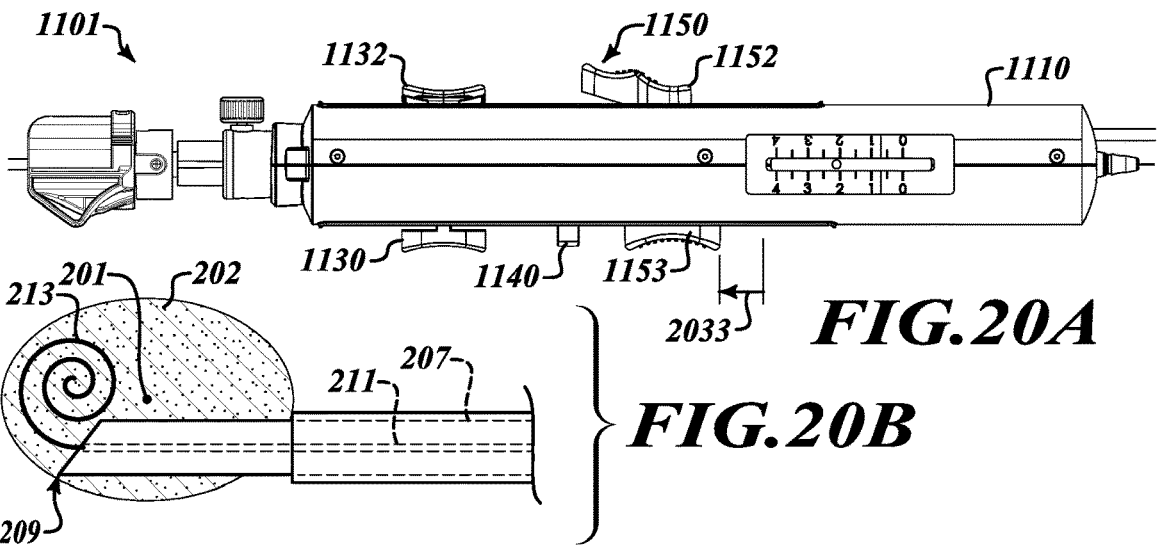
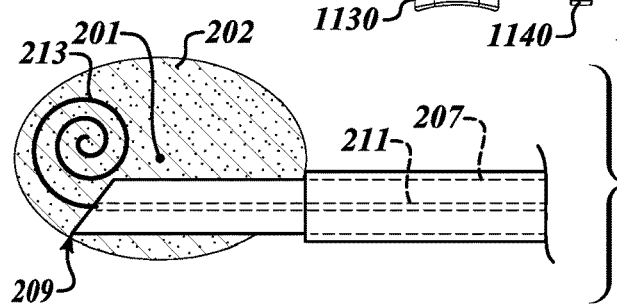
FIG.20A
FIG.20B

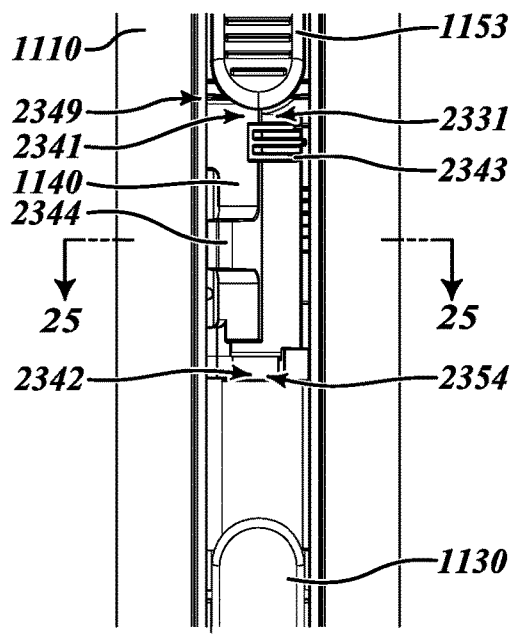
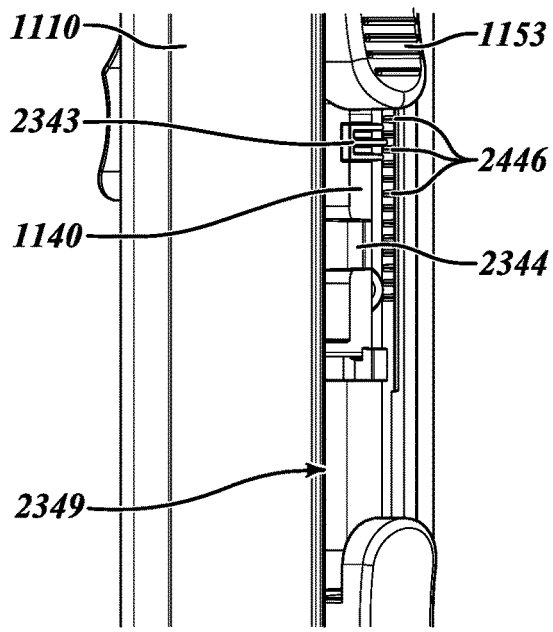
FIG.23  FIG.24
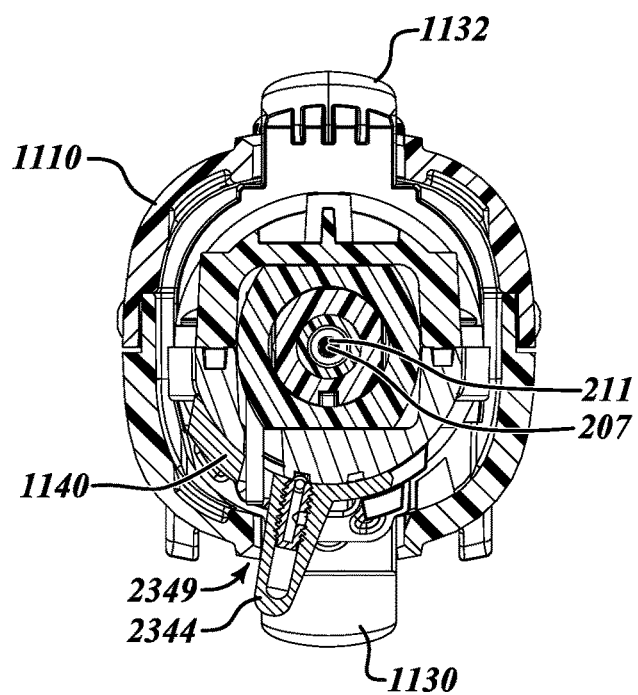
FIG.25

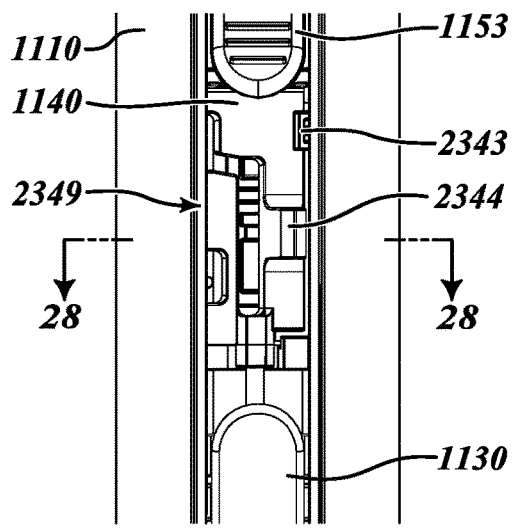
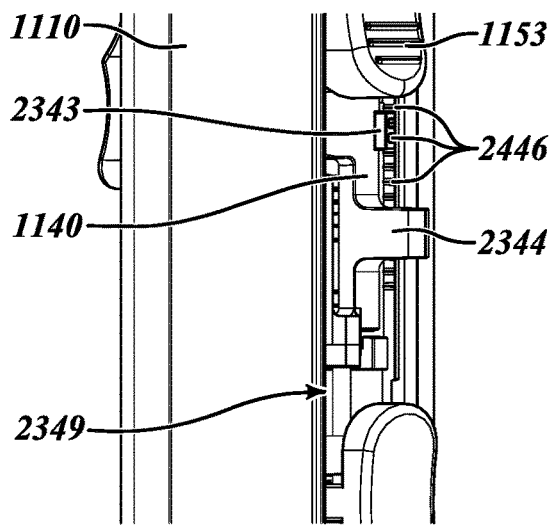
FIG.26  FIG.27
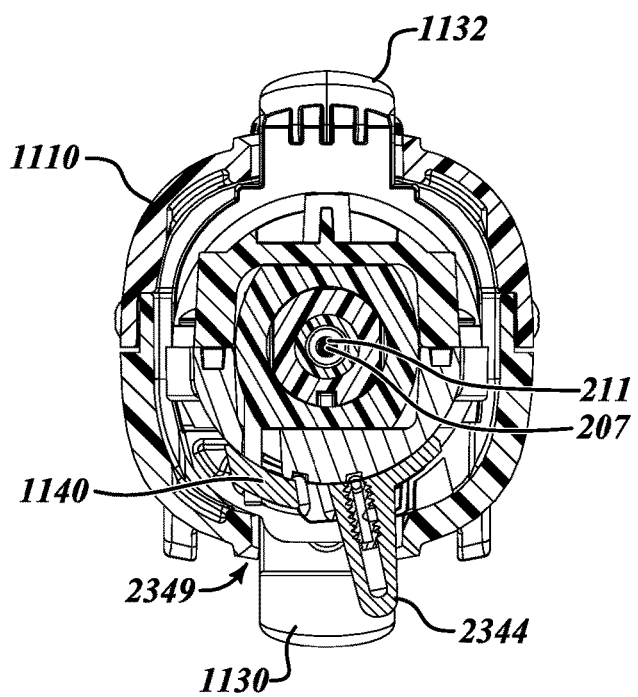
FIG.28

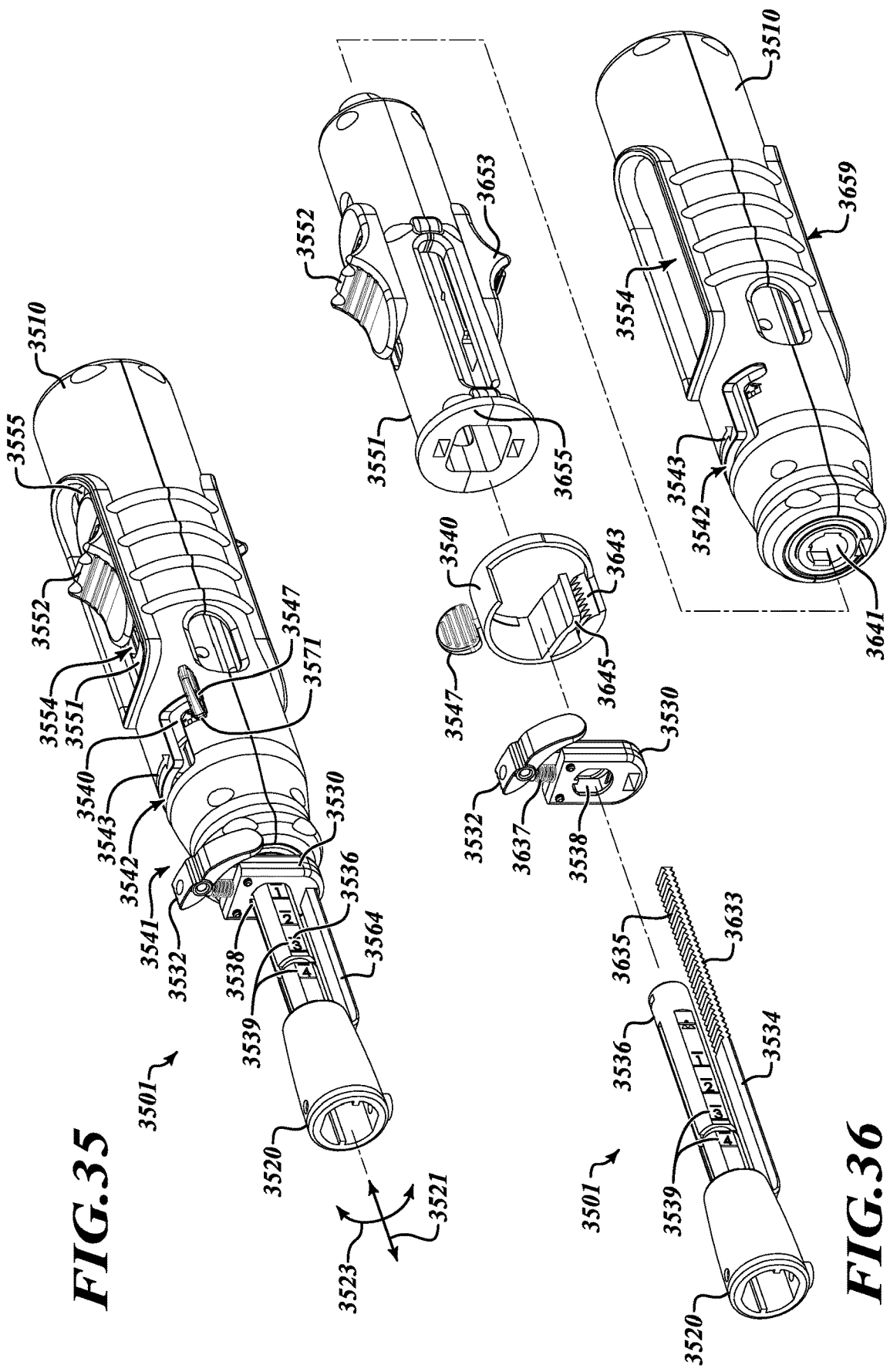

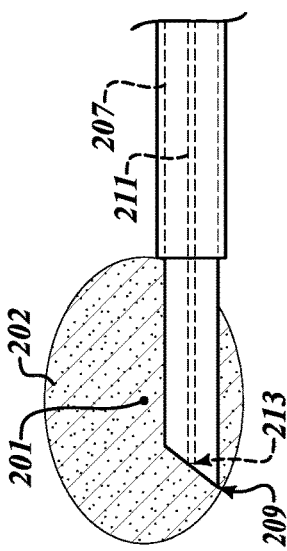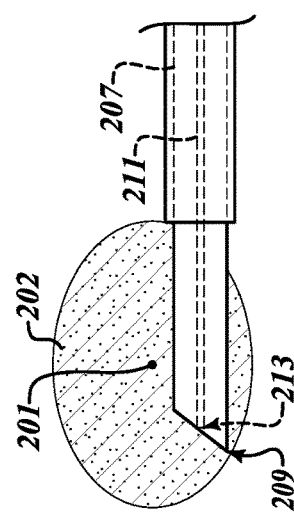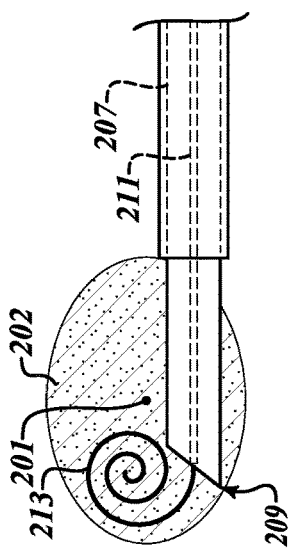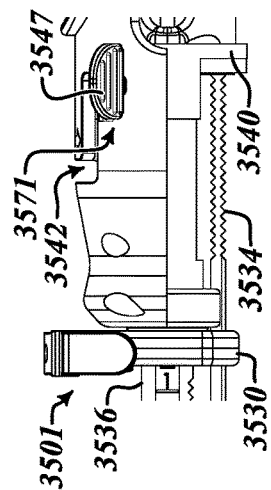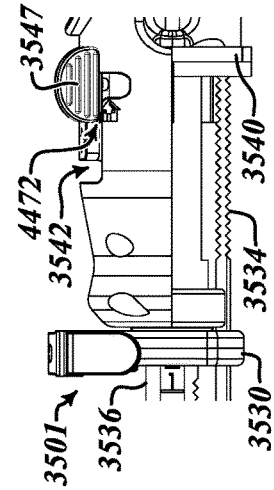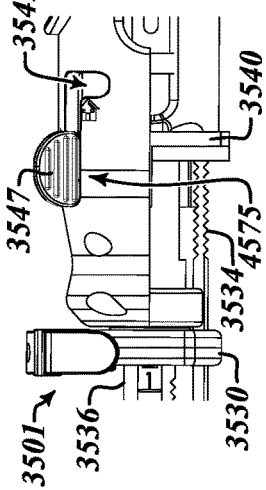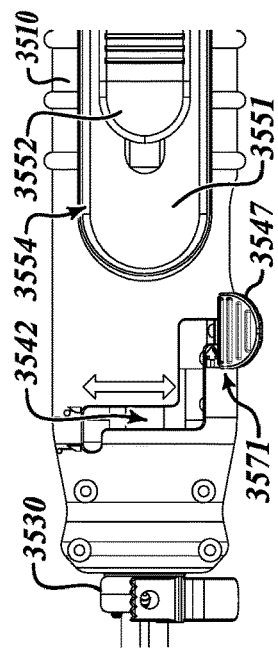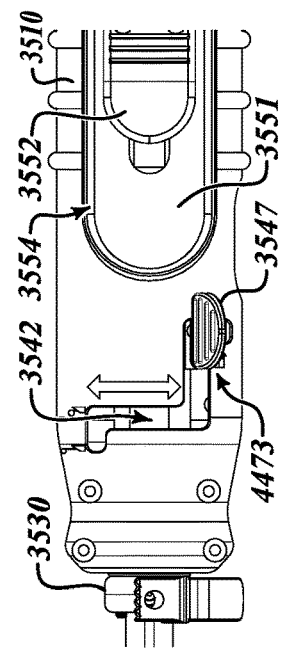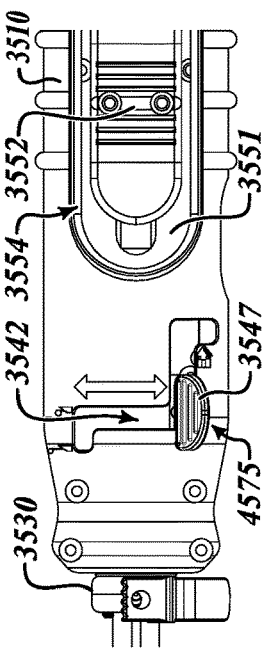

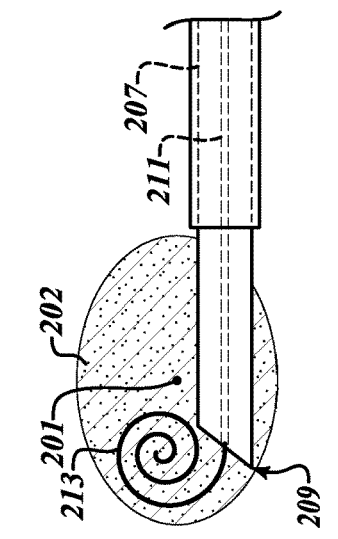 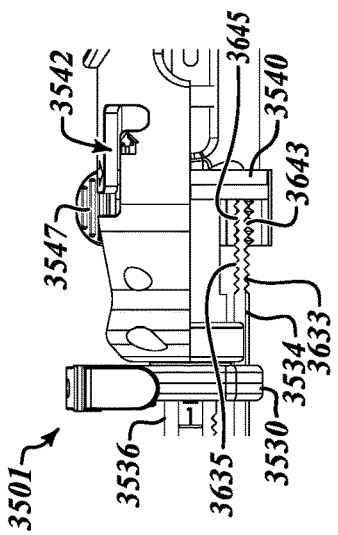 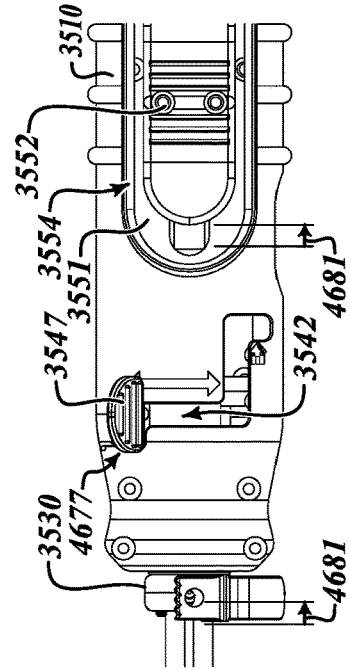
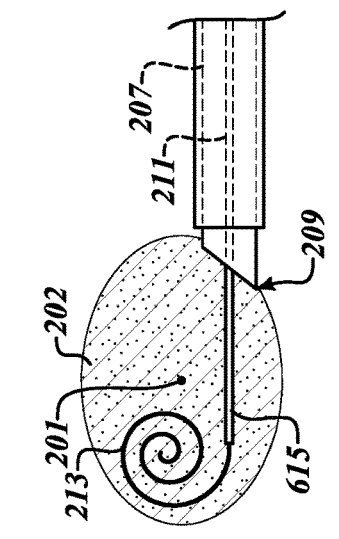 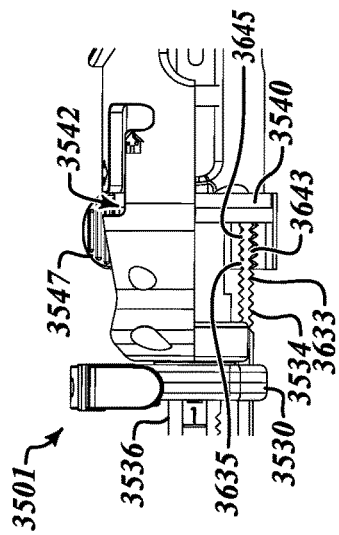 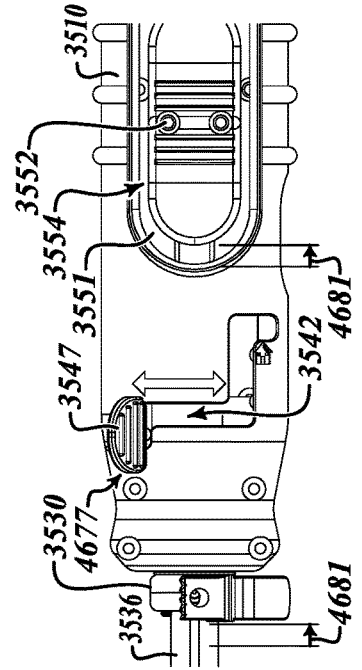

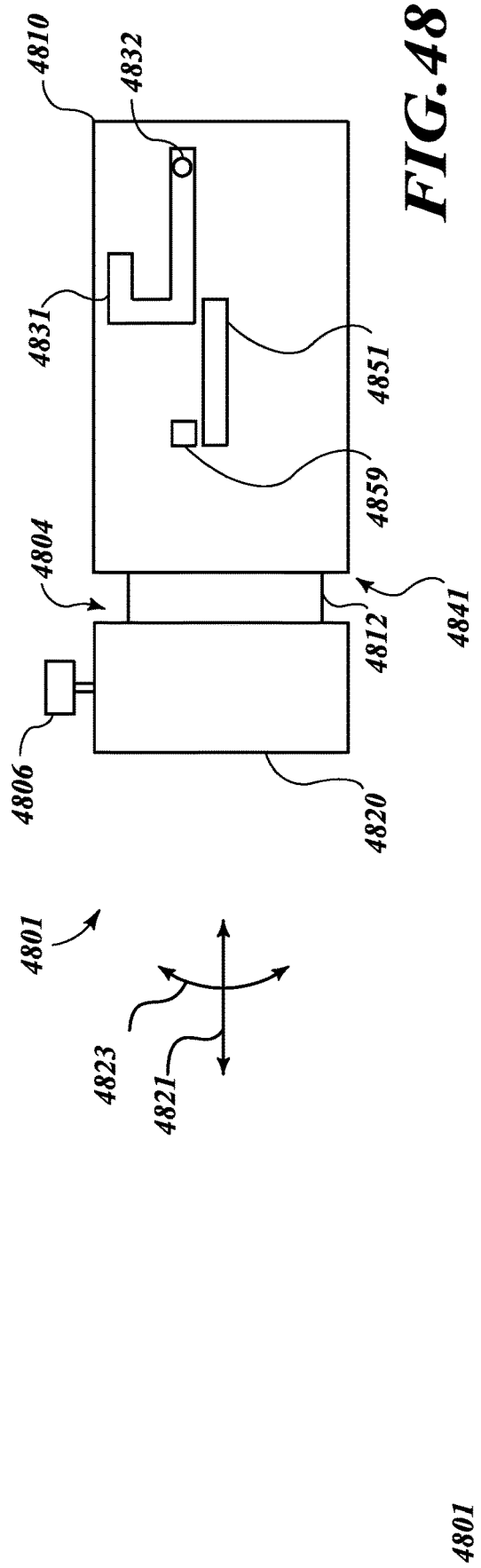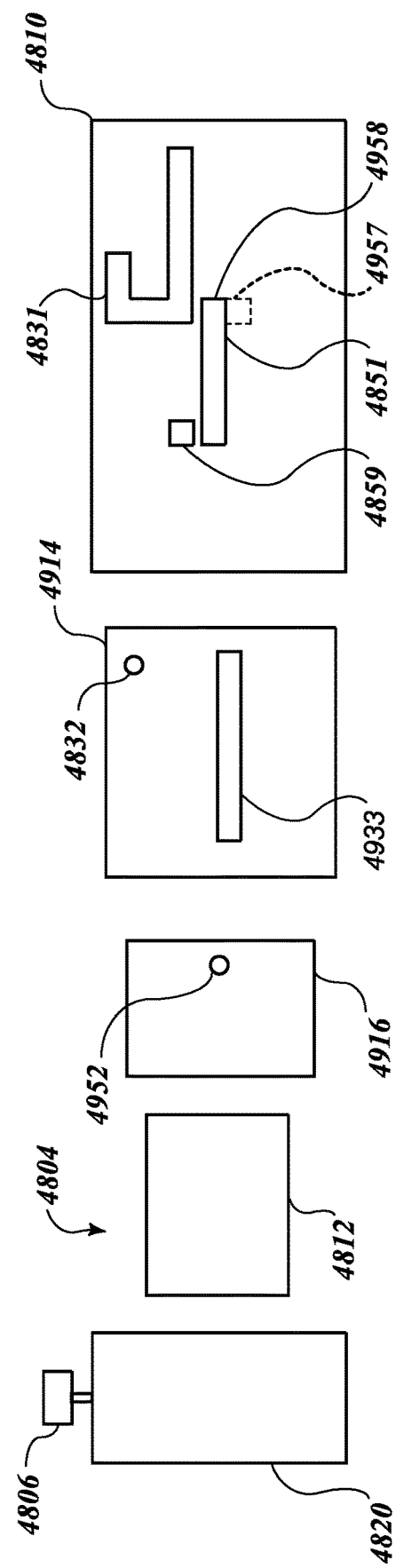

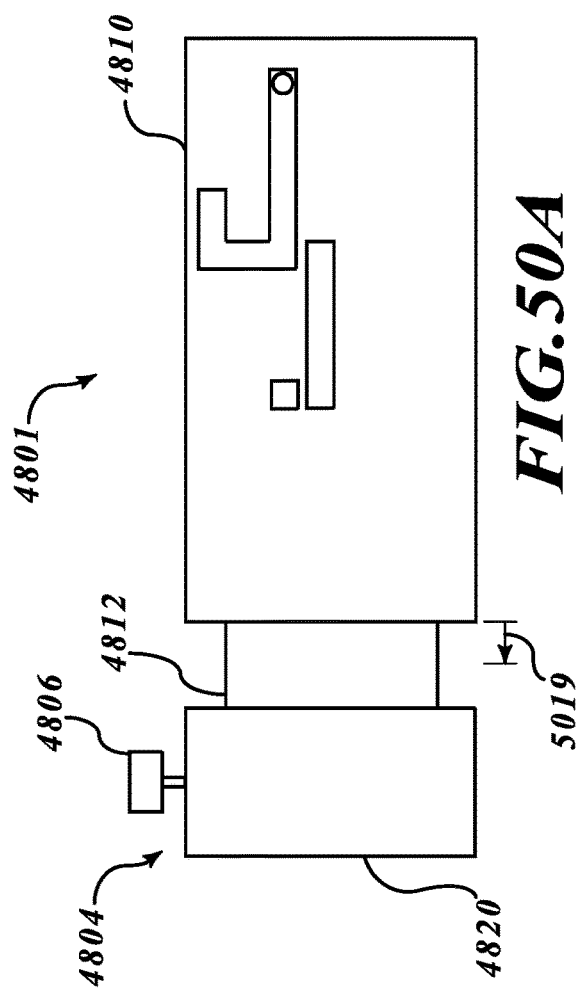
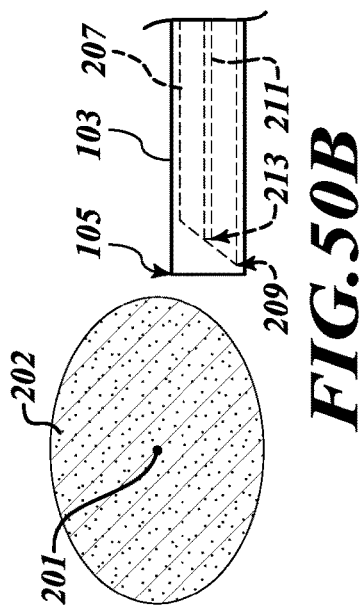
FIG.50A
FIG.50B
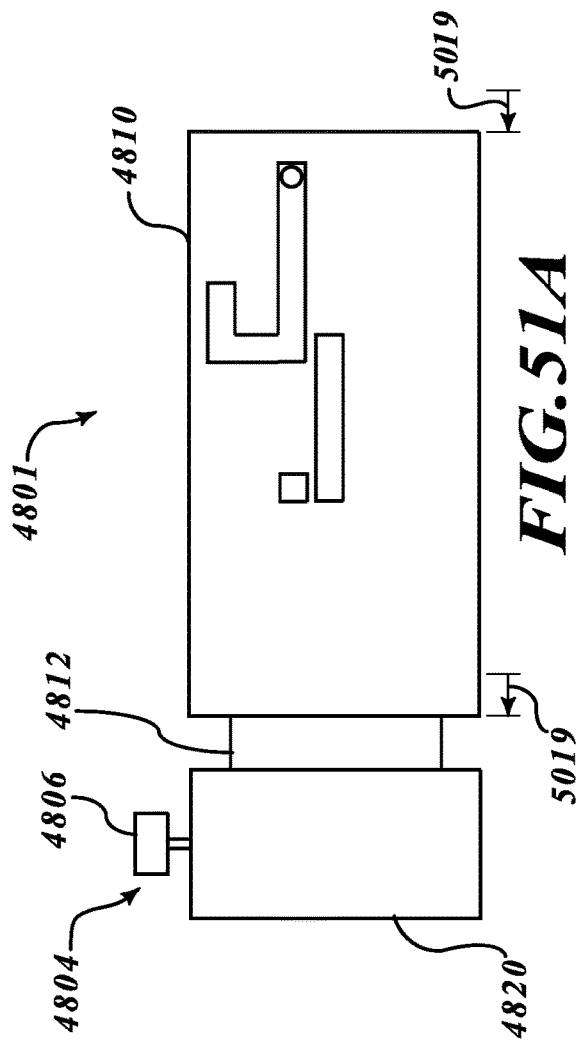
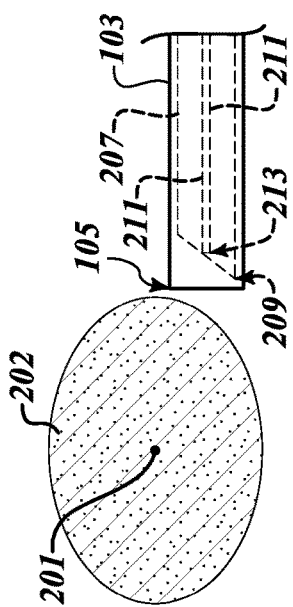
FIG.51A
FIG.51B

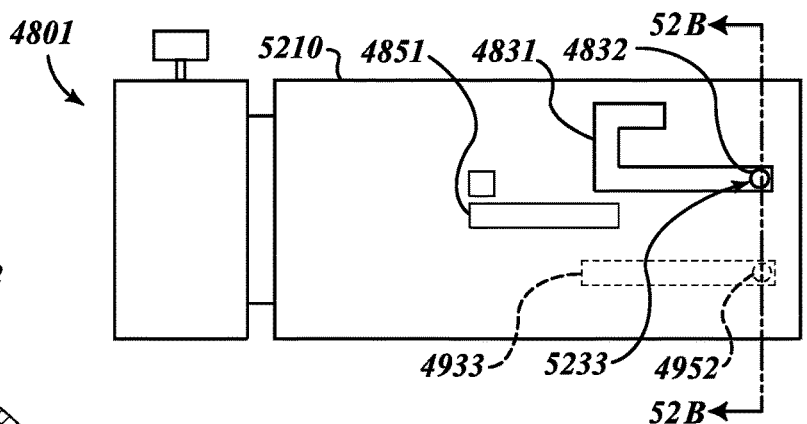
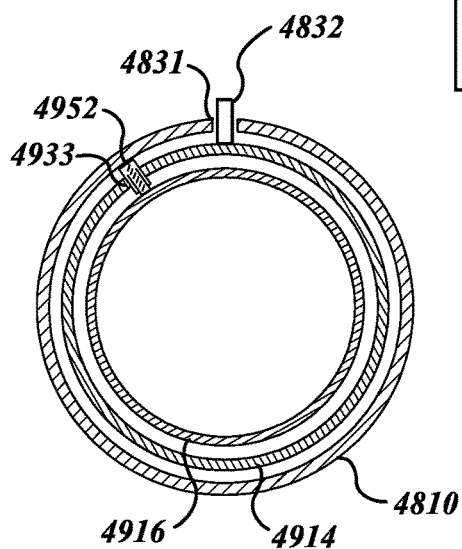
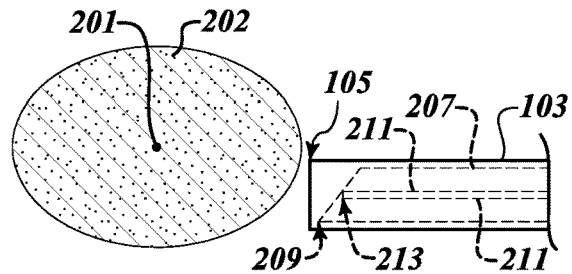
FIG.52A
FIG.52B
FIG.52C
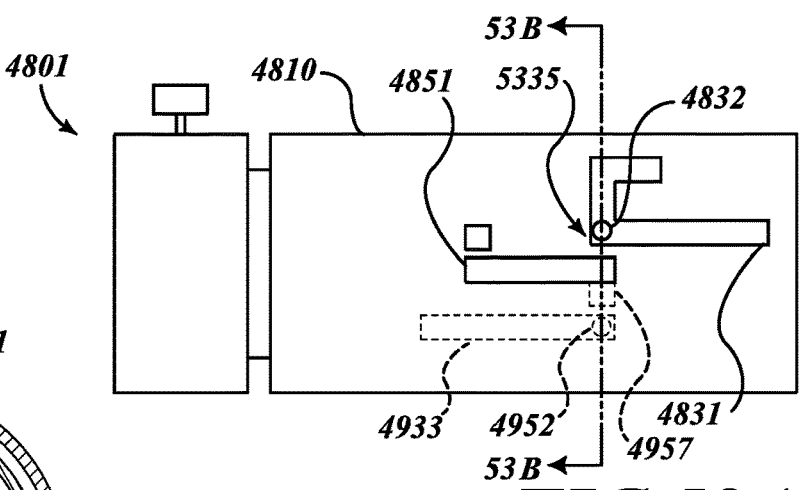
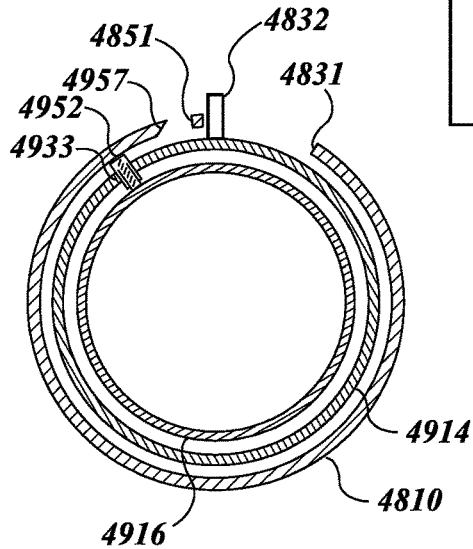
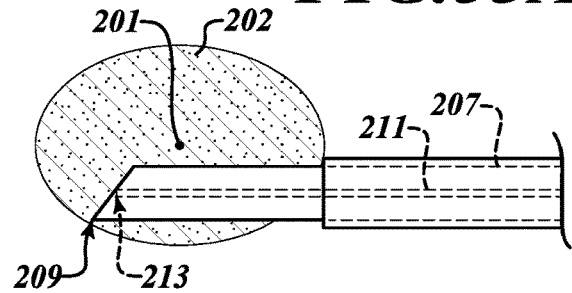
FIG.53A
FIG.53B
FIG.53C

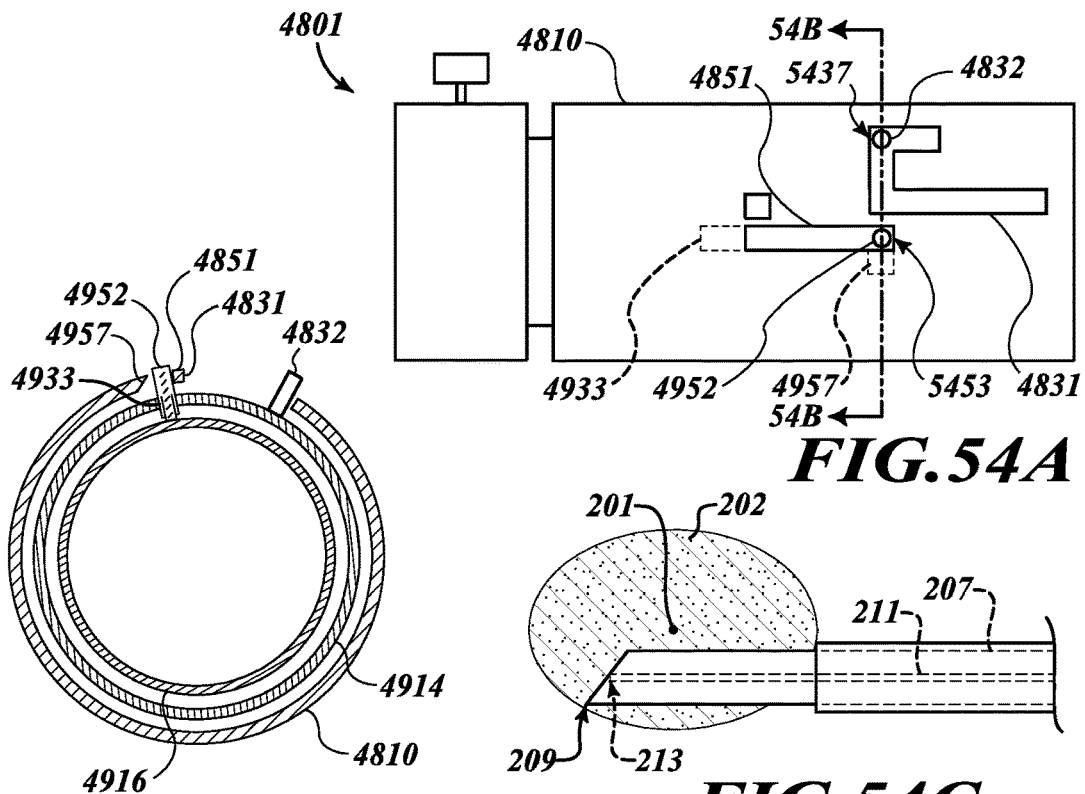
FIG.54A
FIG.54B
FIG.54C
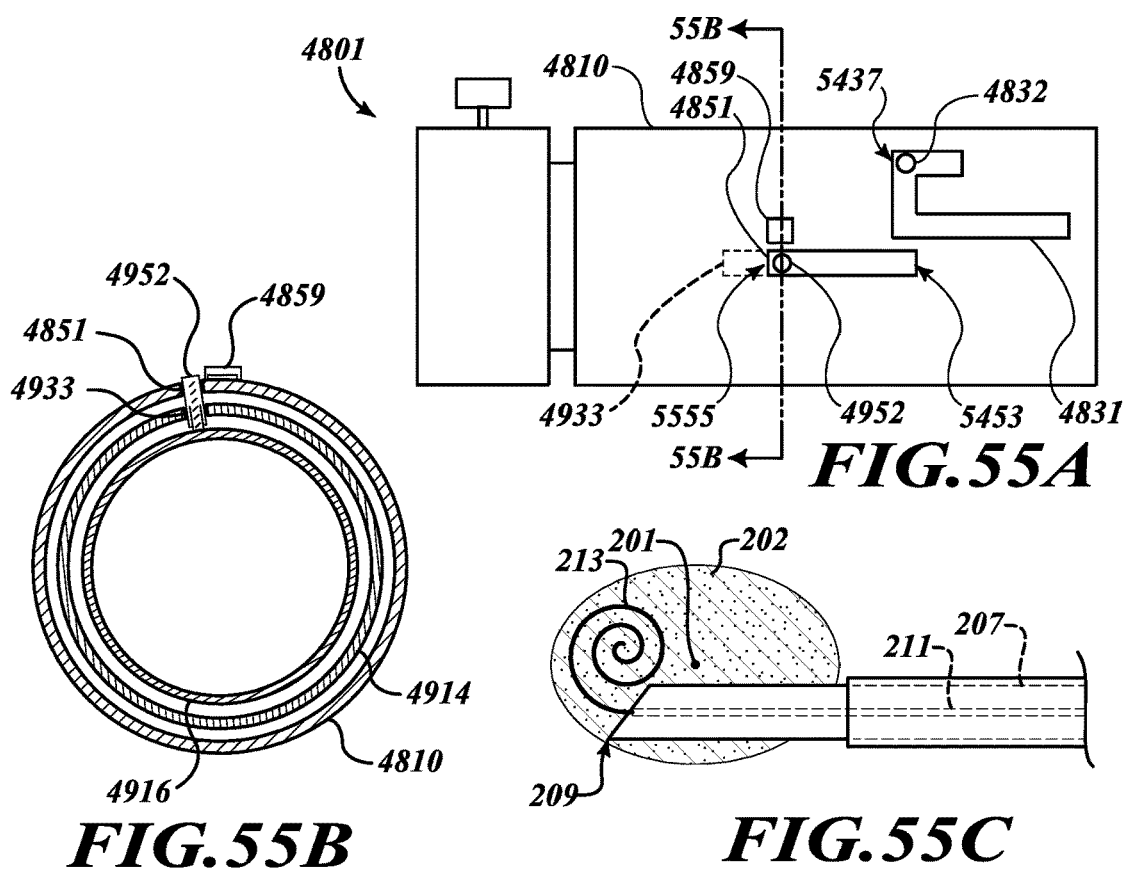
FIG.55A
FIG.55B
FIG.55C

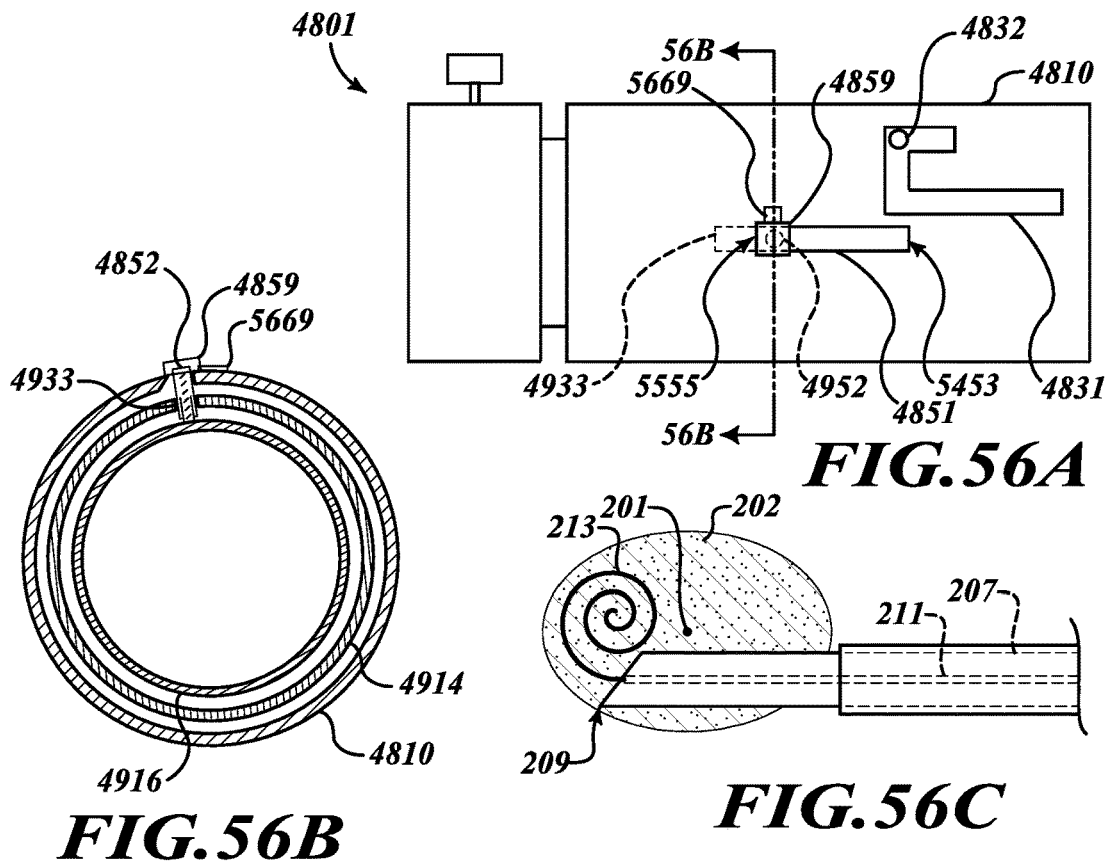
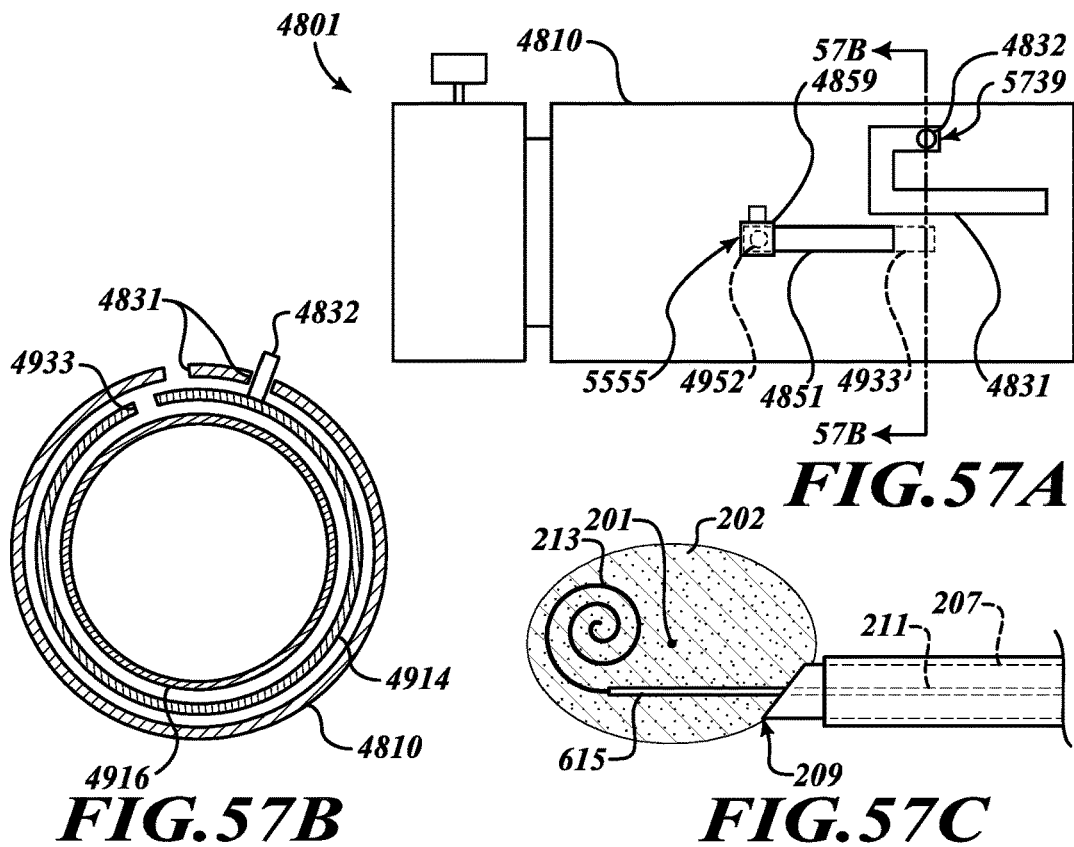

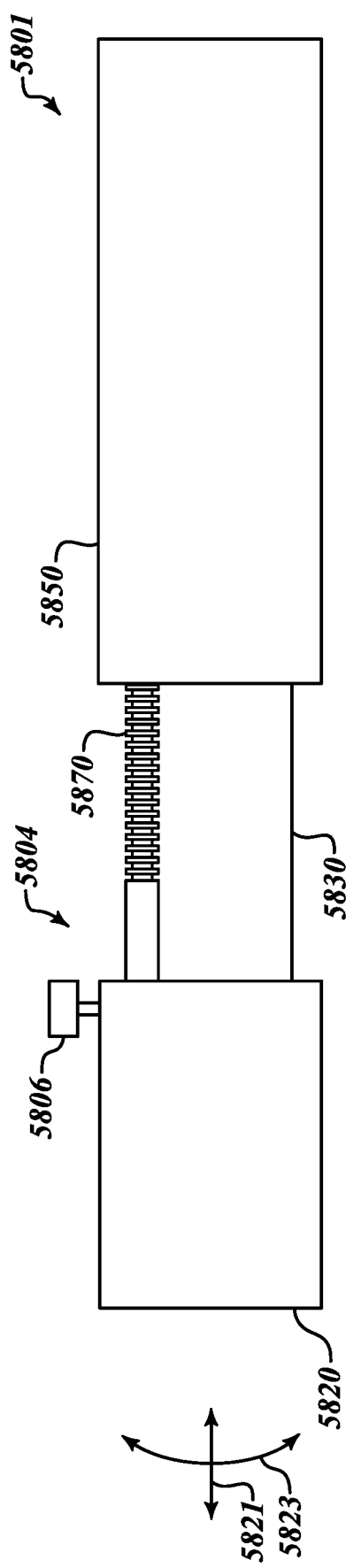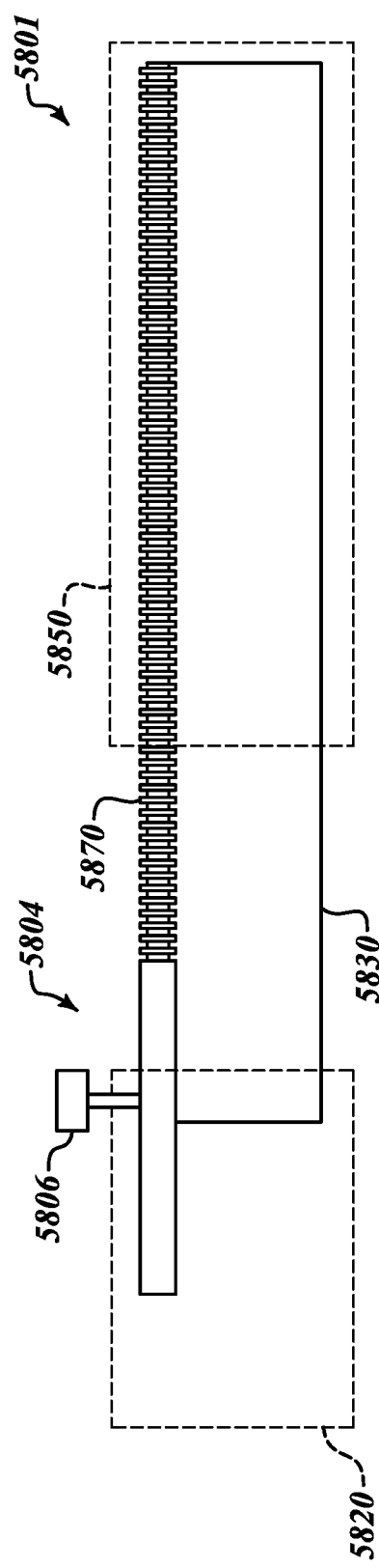

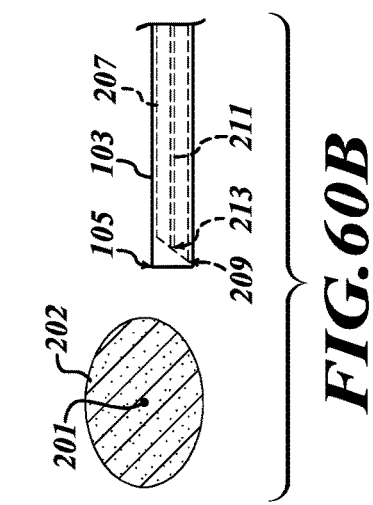
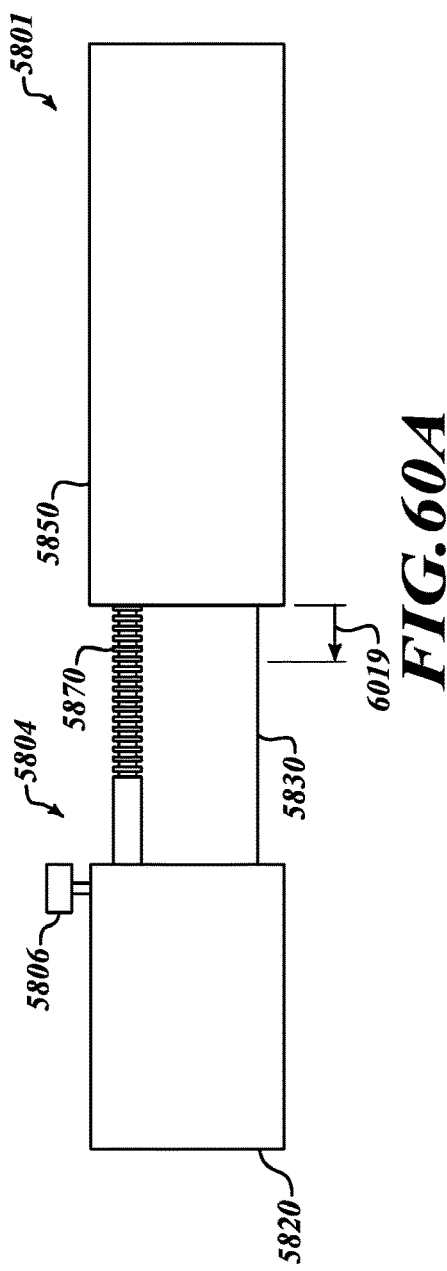
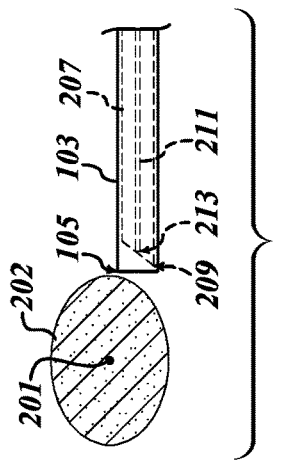
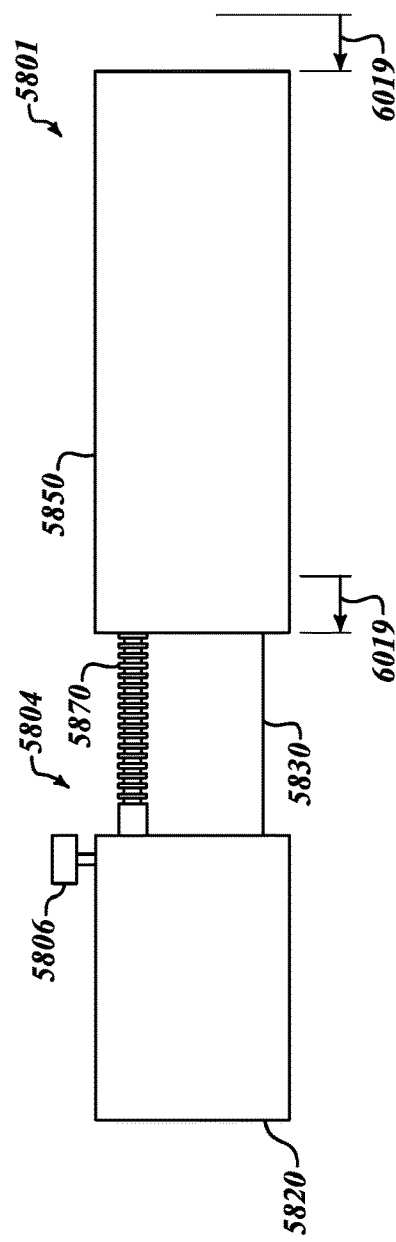

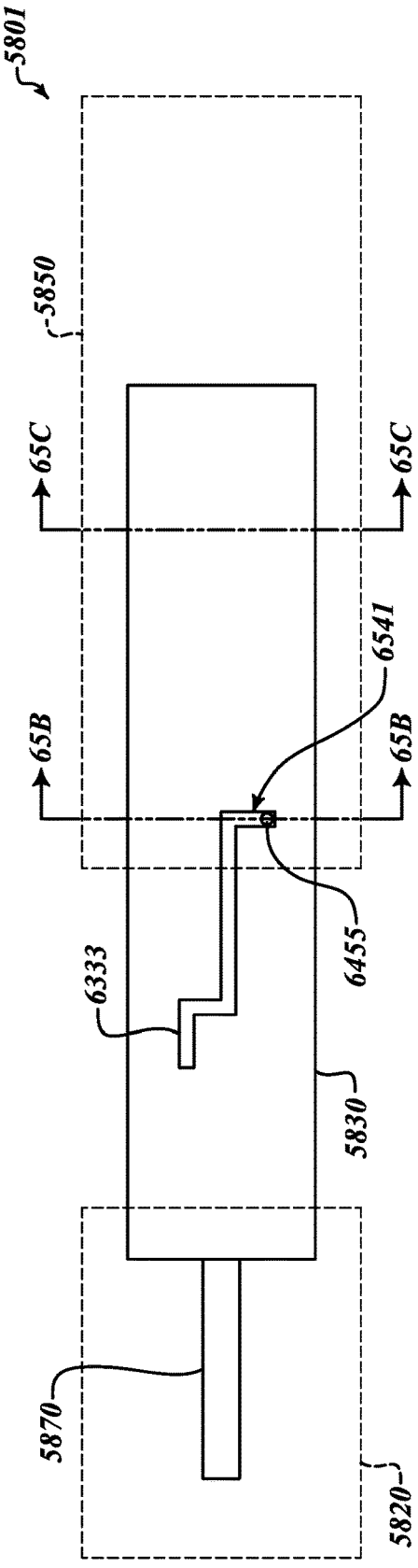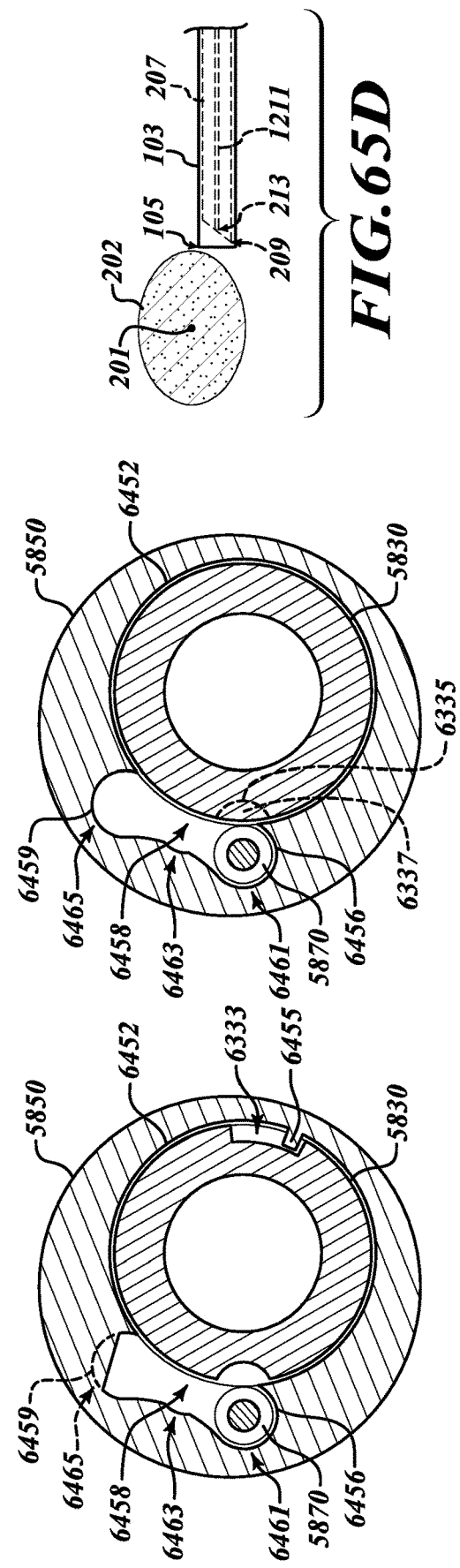

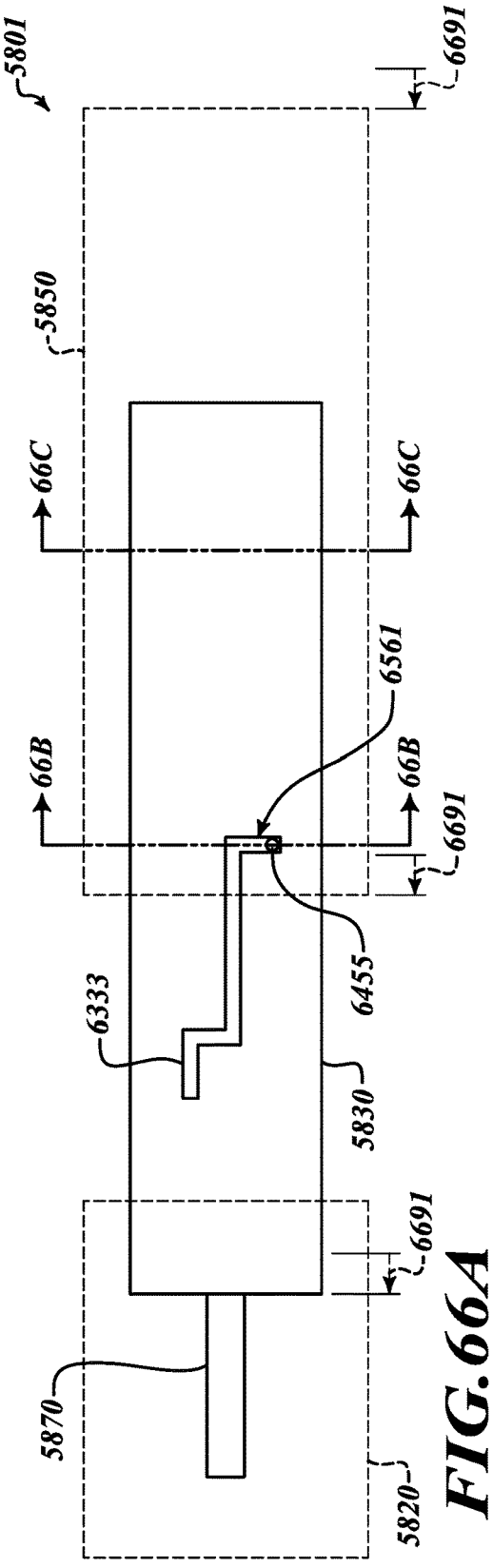
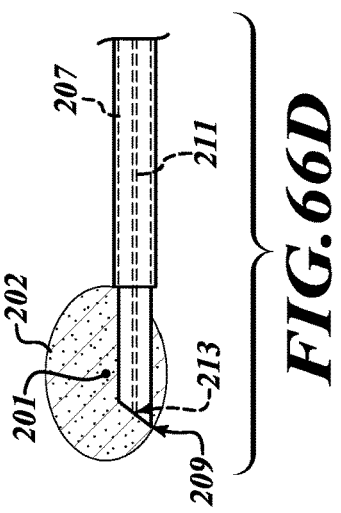
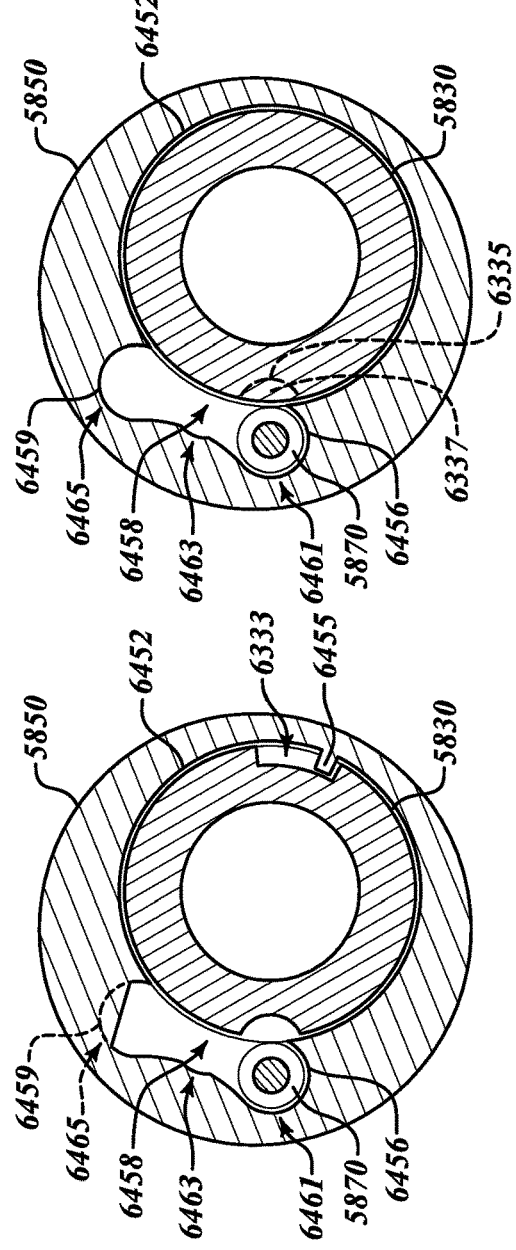
FIG. 66A
FIG. 66D
FIG. 66B
FIG. 66C

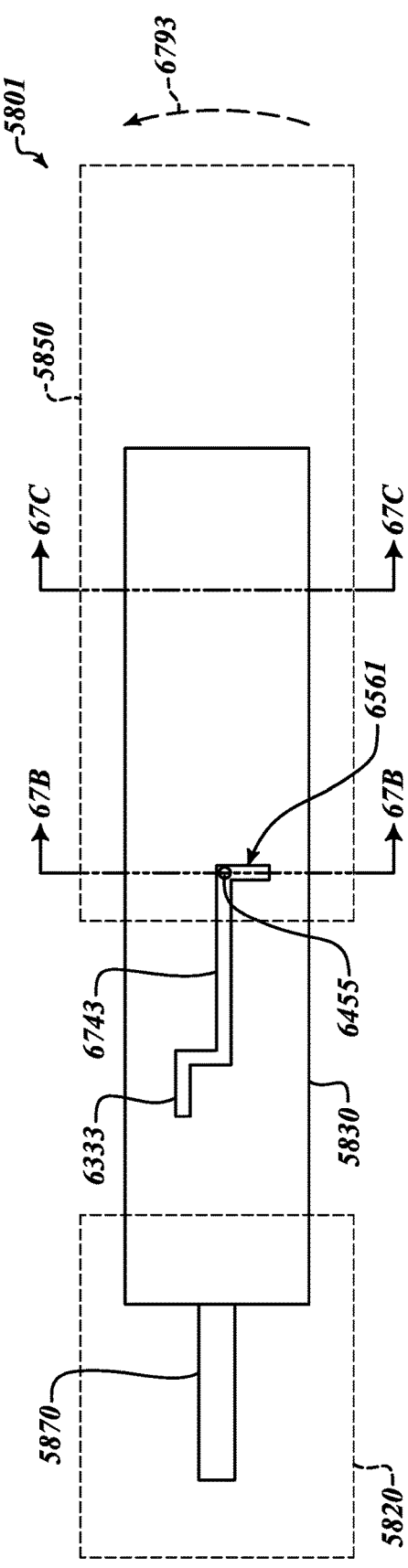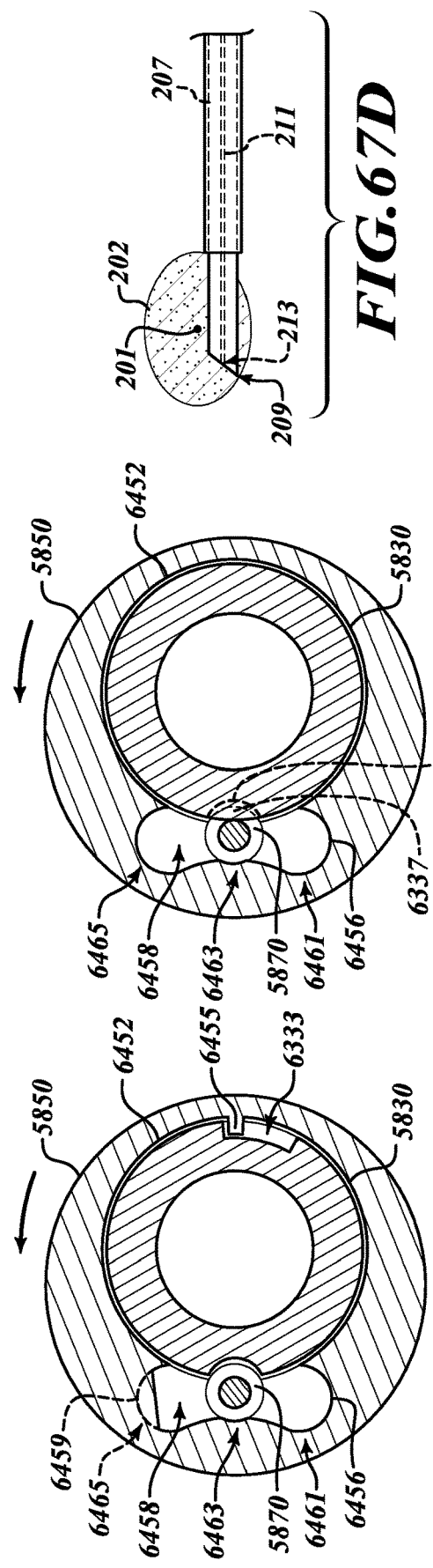
FIG.67A  FIG.67B  FIG.67C  FIG.67D

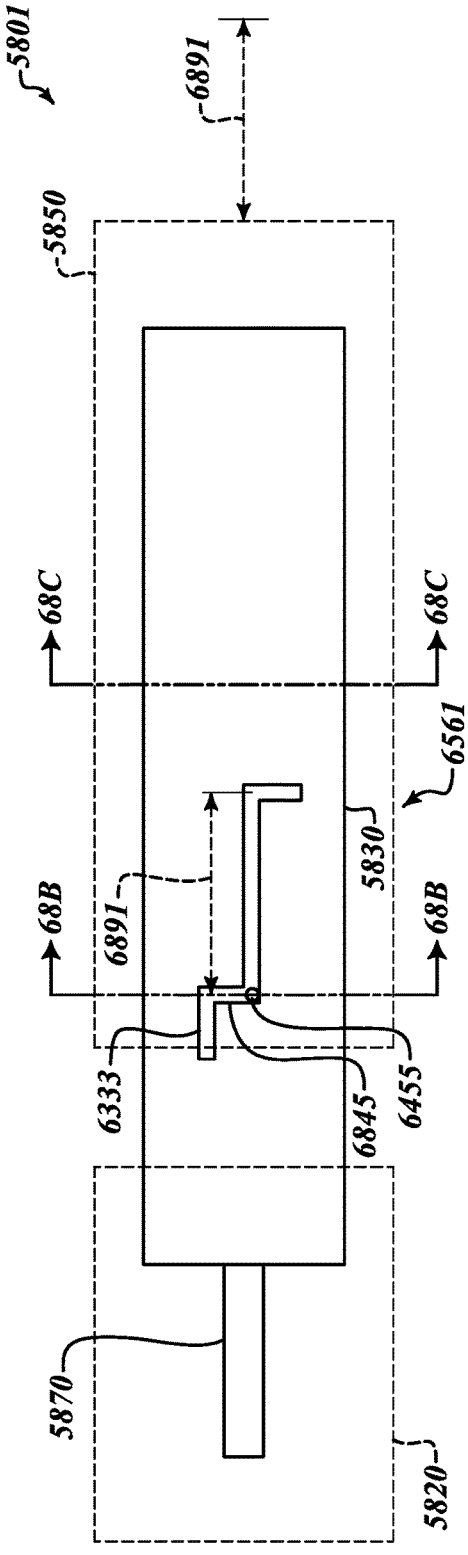
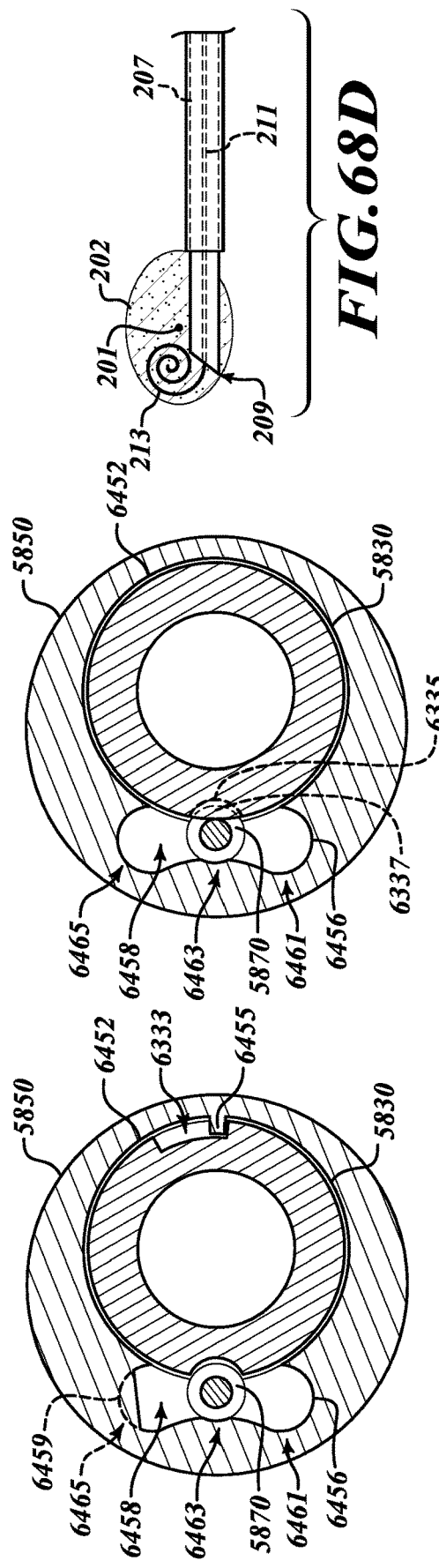
FIG. 68A
FIG. 68B
FIG. 68C
FIG. 68D

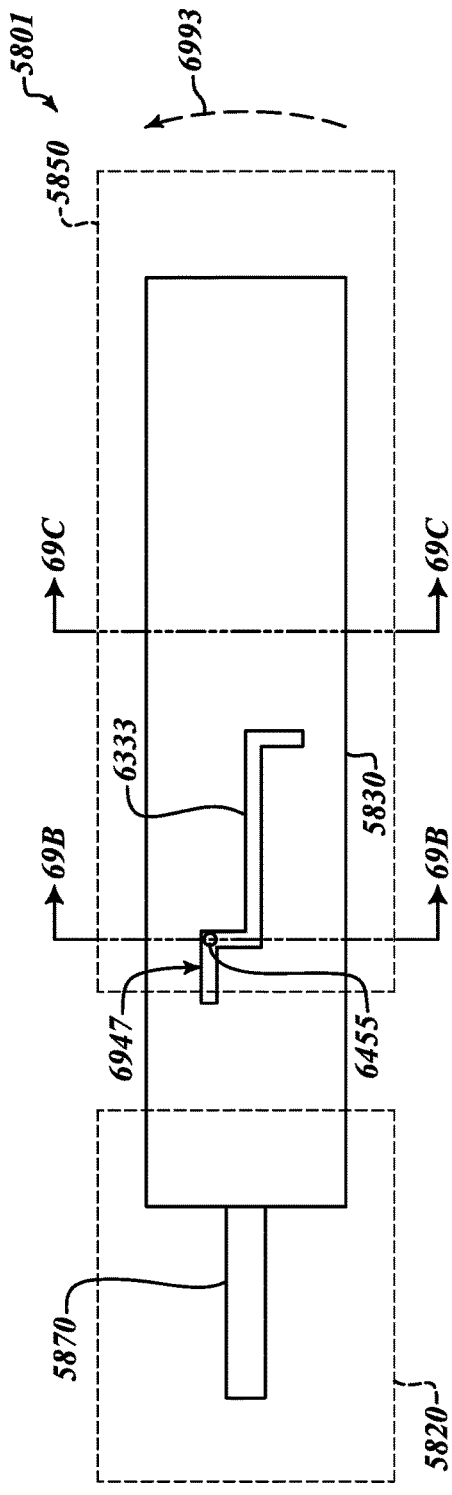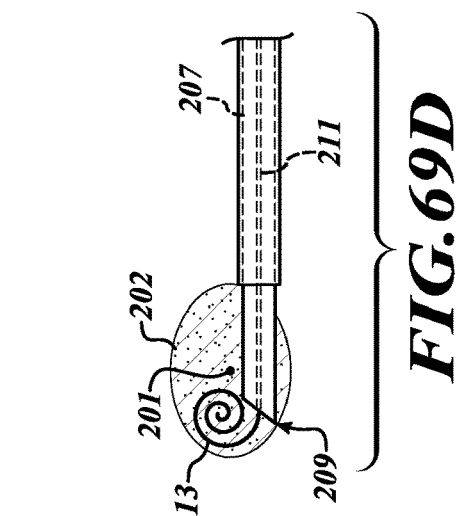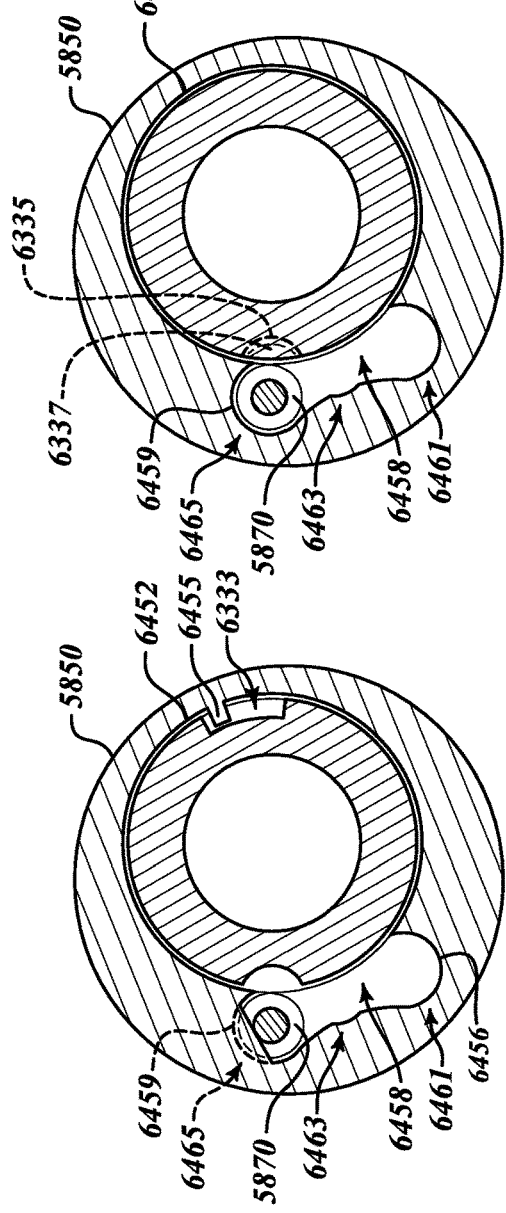

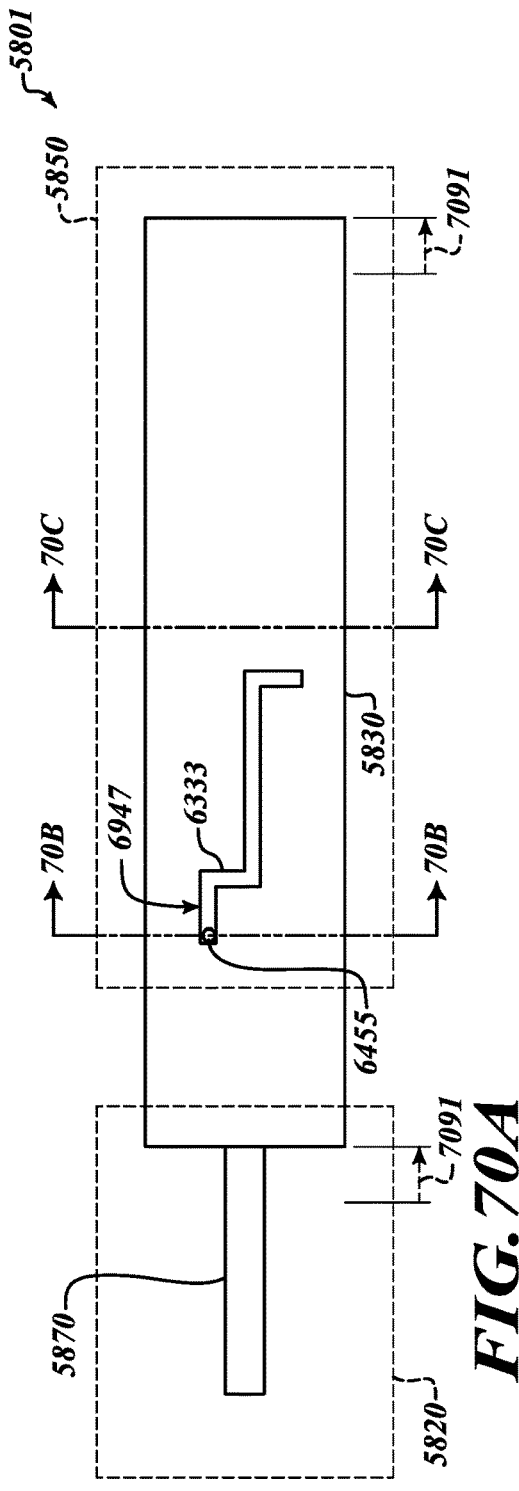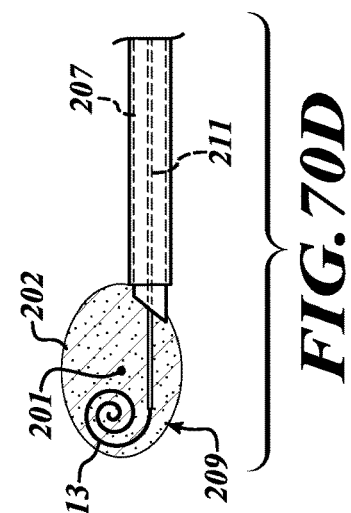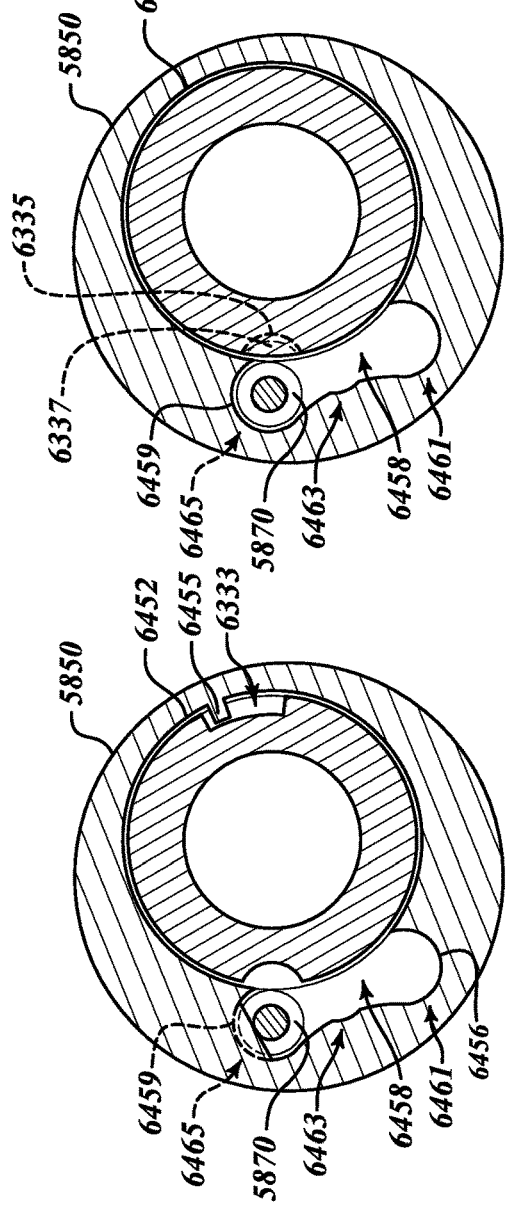

USER INTERFACE AND LOCK FEATURES FOR POSITIONING MULTIPLE COMPONENTS WITHIN A BODY

PRIORITY CLAIM

The present application claims the priority and benefit of U.S. Provisional Patent Application Ser. No. 62/311,226 entitled "HANDLE FOR AN ABLATION DEVICE," filed on Mar. 21, 2016.

FIELD

The present disclosure relates to a user interface and lock features for positioning multiple components within a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve extending one or more electrodes through an orifice or a small incision to a desired location within a body, then applying a radio frequency ("RF") electric current to the electrodes to coagulate and/or ablate tissue at that location. Monopolar electrosurgical instruments only entail use of one electrode that interacts with a neutral electrode, which is likewise connected to the body of a patient. A bipolar electrosurgical instrument typically includes a user interface used for positioning two electrodes, which may include a distal electrode and a proximal electrode.

Positioning one or two electrodes at the desired location is an important part of such electrosurgical treatments. Moving and holding electrodes in place, particularly when more than one electrode has to be moved or held independently of another electrode, may present a challenge for the medical personnel directing the treatment.

SUMMARY

Disclosed embodiments include apparatuses for slidably moving multiple components within a body, systems for treating tissue at a reference point, and methods for moving electrodes into positions for ablative electrical treatment at a reference point.

In an illustrative embodiment, an apparatus for slidably moving multiple features relative to a sheath inserted into a body and positioned relative to a reference point includes a primary actuator configured to move a primary electrode, a secondary actuator configured to move a secondary electrode, and a control mechanism. The control mechanism is configured to selectively prevent movement of at least one of the primary actuator based on a position of the secondary actuator and of the secondary actuator based on a position of the primary actuator and lock positions of the primary actuator and the secondary actuator.

In another illustrative embodiment, a system for treating tissue at a reference point includes a controllable electrical power source configured to selectively provide electrical power between a first pole and a second pole. An electrosurgical apparatus is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point. A sheath lock is configured to selectively lock a position of the sheath. A primary actuator is configured to move the primary electrode. A secondary actuator is configured to move the secondary electrode. A control mechanism includes a control mechanism configured to selectively prevent movement of at least one of the primary actuator based on a position of the secondary actuator and of the secondary actuator based on a position of the primary actuator and to lock positions of the primary actuator and the secondary actuator.

In a further illustrative embodiment, a method is provided for preparing electrodes for ablative electrical treatment of tissue at a reference point. A sheath containing a primary electrode and a secondary electrode is extended, wherein the secondary electrode is contained within the primary electrode and initially coupled to move with the primary electrode. Movement of the primary electrode is unlocked, the primary electrode is moved to a first location near the reference point, and the primary electrode is locked in position at the first location. Movement of the secondary electrode is unlocked, the secondary electrode is moved to a second location near the reference point, and the secondary electrode is locked in position at the second location.

In an additional illustrative embodiment, an apparatus for slidably moving multiple features relative to a sheath inserted into a body and positioned relative to a reference point includes a primary actuator configured to move a primary electrode, a secondary actuator configured to deploy a secondary electrode by moving the secondary electrode independently of the primary electrode, and a control mechanism. The control mechanism includes a primary release configured to selectively permit movement of the primary actuator, a secondary release configured to selectively decouple the secondary actuator from the primary actuator and permit movement of the secondary actuator within a predetermined range, and an actuator interlock configured to selectively prevent activation of the primary release.

In another illustrative embodiment, a system for treating tissue at a reference point includes an electrical power source configured to selectively provide electrical power between a first pole and a second pole. An electrosurgical apparatus is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point and a sheath lock configured to selectively lock a position of the sheath. A primary actuator is configured to move the primary electrode. A secondary actuator is configured to deploy the secondary electrode by moving the secondary electrode independently of the primary electrode. A control mechanism includes a primary release configured to selectively permit movement of the primary actuator, a secondary release configured to selectively decouple the secondary actuator from the primary actuator and permit movement of the secondary actuator within a predetermined range, and an actuator interlock configured to selectively prevent activation of the primary release.

In a further illustrative embodiment, a method of using an apparatus to move electrodes into positions for ablative electrical treatment of tissue at a reference point includes extending a sheath toward a reference point. The sheath contains a primary electrode mechanically coupled to a primary actuator and selectively lockable by a primary release. The sheath also contains a secondary electrode mechanically coupled to a secondary actuator and lockable by a secondary release, where the secondary electrode is slidably received within the primary electrode. The primary release is activated to permit movement of the primary actuator. The primary actuator is moved to move the primary electrode to a first location relative to the reference point. The primary release is locked to lock the primary actuator to maintain the primary electrode at the first location. The secondary release is activated to decouple the secondary actuator from the primary actuator to permit movement of the secondary actuator independent of the primary actuator. The secondary actuator is moved to move the secondary electrode to a second location relative to the reference point. The secondary release is locked to lock the secondary actuator to maintain the secondary electrode at the second location.

In an additional illustrative embodiment, an apparatus for slidably moving multiple features relative to a sheath inserted into a body and positioned relative to a reference point includes a housing mechanically coupled with a primary electrode and defining a guide slot having sections transverse and parallel to an axis of the housing. A sleeve having a distal end is configured to engage an electrosurgical device and a proximal end configured to be slidably received within a first end of the housing. A latch disposed at the first end of the housing is configured to selectively enable the housing to move along the sleeve to move the primary electrode to a first location relative to the reference point. A secondary actuator is received within the housing and coupled with a secondary electrode, where the secondary actuator is configured to move independently of the primary electrode parallel to the axis of the housing. An interlock lever mechanically is coupled with the secondary actuator and extends through the guide slot. An interlock lever also includes a clamp configured to lock the secondary actuator to the sleeve when the secondary electrode reaches a second location relative to the reference point.

In another illustrative embodiment, a system for treating tissue at a reference point includes an electrical power source configured to selectively provide electrical power between a first pole and a second pole. An electrosurgical device is configured to be inserted into a body to convey a sheath containing a primary electrode electrically coupled to the first pole of the electrical power source and a secondary electrode electrically coupled to the second pole of the electrical power source to a vicinity of a reference point. A sheath actuator is configured to move the sheath relative to the reference point. A sheath lock is configured to selectively lock a position of the sheath. A housing is mechanically coupled with a primary electrode and includes a guide slot having sections transverse and parallel to an axis of the housing. A sleeve having a distal end is configured to engage a bronchoscope and a proximal end configured to be slidably received within a first end of the housing. A latch is disposed at the first end of the housing and is configured to selectively enable the housing to move along the sleeve to move the primary electrode to a first location relative to the reference point. A secondary actuator received within the housing is coupled with a secondary electrode and is configured to move independently of the primary electrode parallel to the axis of the housing. An interlock lever is mechanically coupled with the secondary actuator and extends through the guide slot, and the interlock lever further includes a clamp configured to lock the secondary actuator to the sleeve when the secondary electrode reaches a second location relative to the reference point.

In a further illustrative embodiment, a method of moving electrodes into positions for ablative electrical treatment of tissue at a reference point includes extending a sheath that contains a primary electrode that is mechanically coupled to a housing and is selectively lockable by a latch and a secondary electrode that is mechanically coupled to the secondary actuator and is lockable by an interlock lever. The secondary electrode is slidably received within the primary electrode. The latch is released to enable the housing to move the primary electrode relative to the reference point. The housing is slid to move the primary electrode to a first location relative to the reference point. The latch is secured to prevent movement of the housing relative to the sleeve. The interlock lever is moved through a series of positions in the guide slot on the housing for decoupling the secondary electrode from the primary electrode and moving the secondary electrode to a second location relative to the reference point.

In an additional embodiment, an apparatus for slidably moving multiple features relative to a sheath inserted into a body and positioned relative to a reference point includes a secondary electrode slider that is mechanically coupled with a secondary electrode and that supports a secondary actuator. A primary electrode slider is configured to slidably and rotatably receive the secondary electrode slider, the primary electrode slider being mechanically coupled with a primary electrode, supporting a primary actuator, and defining an intermediate guide slot configured to receive and engage the secondary actuator. An outer housing includes a first end facing toward the reference point. The outer housing is configured to slidably and rotatably receive the primary electrode slider and defines a first guide slot configured to receive and engage the primary actuator and a second guide slot configured to receive the secondary actuator when the secondary actuator is positioned under the second guide slot.

In another illustrative embodiment, a system for treating tissue at a reference point includes an electrical power source configured to selectively provide electrical power between a first pole and a second pole. An electrosurgical device is configured to be inserted into a body to convey a sheath containing a primary electrode electrically coupled to the first pole of the electrical power source and a secondary electrode electrically coupled to the second pole of the electrical power source to a vicinity of the reference point. A sheath actuator is configured to move the sheath relative to the reference point. A sheath lock is configured to selectively lock a position of the sheath. A secondary electrode slider is mechanically coupled with a secondary electrode and supports a secondary actuator. A primary electrode slider is configured to slidably and rotatably receive the secondary electrode slider, is mechanically coupled with a primary electrode, supports a primary actuator, and defines an intermediate guide slot configured to receive and engage the secondary actuator. An outer housing has a first end facing toward the reference point and is configured to slidably and rotatably receive the primary electrode slider. The outer housing also includes a first guide slot configured to receive and engage the primary actuator and a second guide slot configured to receive the secondary actuator when the secondary actuator is positioned under the second guide slot.

In a further illustrative embodiment, a method of moving electrodes into positions for ablative electrical treatment of tissue at a reference point includes extending a sheath, wherein the sheath contains a primary electrode and a secondary electrode slidably received within the primary electrode. An apparatus coupled with the primary electrode and the secondary electrode is deployed, wherein the apparatus includes a secondary electrode slider mechanically coupled with a secondary electrode and supporting a secondary actuator. The apparatus includes a primary electrode slider that is mechanically coupled with a primary electrode, supports a primary actuator, and defines an intermediate guide slot configured to receive and engage the secondary actuator. The apparatus also includes an outer housing having a first end, wherein the outer housing defines a first guide slot configured to receive and engage the primary actuator and a second guide slot configured to receive the secondary actuator when the secondary actuator is positioned under the second guide slot. The primary actuator is moved toward the front end of the outer housing to position the primary electrode at a first location relative to the reference point. The outer housing is rotated to expose the intermediate guide slot beneath the second guide slot. The secondary actuator is moved toward the first end of the outer housing to position the secondary electrode at a second location relative to the reference point.

In an additional illustrative embodiment, an apparatus is provided for slidably moving multiple features relative to a sheath inserted into a body and positioned relative to a reference point. A lock rod is configured to be fixed in a position relative to a reference point. A primary housing is mechanically coupled with a primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. A secondary housing is mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. Rotation of the secondary housing selectively moves the lock rod in and out of the primary lock channel and within the secondary lock channel to selectively allow and prevent sliding movement relative to the lock rod of at least one of the primary housing and the secondary housing.

In another illustrative embodiment, a system for treating tissue at a reference point includes an electrical power source configured to selectively provide electrical power to a primary electrode and a secondary electrode between a first pole and a second pole. A lock rod is configured to be fixed in a position relative to a reference point. A sheath actuator is configured to move a sheath housing the primary electrode and the secondary electrode relative to a reference point and to set a position of the lock rod relative to the reference point. A sheath lock is configured to selectively lock a position of the sheath and the lock rod. A primary housing is mechanically coupled with the primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. A secondary housing is mechanically coupled with the secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. Rotation of the secondary housing selectively moves the lock rod in and out of the primary lock channel and within the secondary lock channel to selectively allow and prevent sliding movement relative to the lock rod of at least one of the primary housing and the secondary housing.

In a further illustrative embodiment, a method is provided for using an apparatus to move electrodes into positions for ablative electrical treatment of tissue at a reference point. A sheath is extended, wherein the sheath contains a primary electrode and a secondary electrode slidably received within the primary electrode. An apparatus coupled with the primary electrode and the secondary electrode is deployed. The apparatus includes a lock rod configured to be fixed in a position relative to a reference point. The apparatus also includes a primary housing is mechanically coupled with a primary electrode. The primary housing further includes an outward-facing guide slot configured to selectively limit and enable sliding movement of a guide member. The primary housing also includes a primary lock channel configured to rotatably receive the lock rod to prevent sliding movement of the primary housing relative to the lock rod. The apparatus also includes a secondary housing mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod. The secondary housing is successively slide and rotated to move the secondary housing and the primary housing to move the primary electrode and the secondary electrode to positions relative to the reference point, and the primary housing is slide to move the primary electrode.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 7A and 8A are schematic diagrams of a sheath actuator for positioning a sheath relative to a reference point;

FIGS. 7B and 8B are schematic diagrams of positioning of distal ends of the sheath, a primary electrode, and a secondary electrode relative to a reference point corresponding to positions of the sheath actuator of FIGS. 7A and 8A, respectively;

Figure 15:
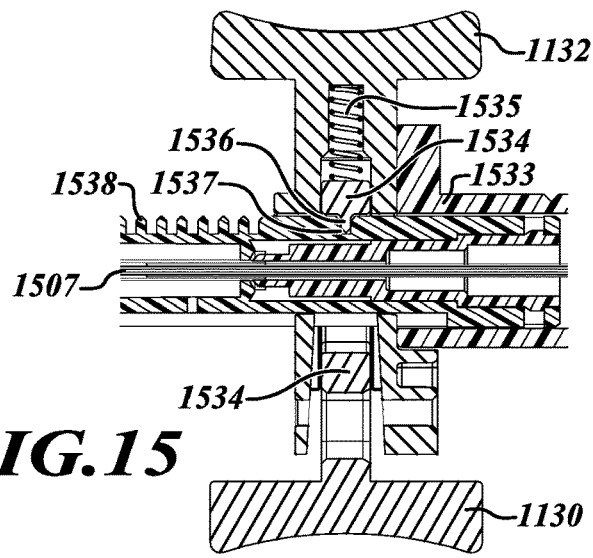
Figure 16:
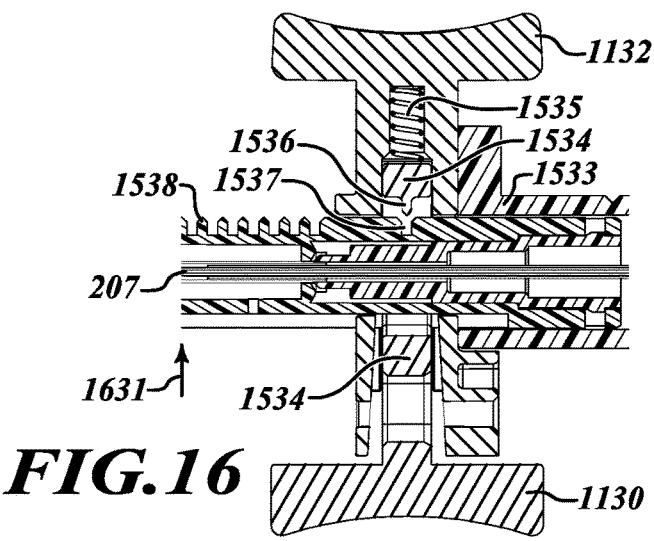
Figure 17:
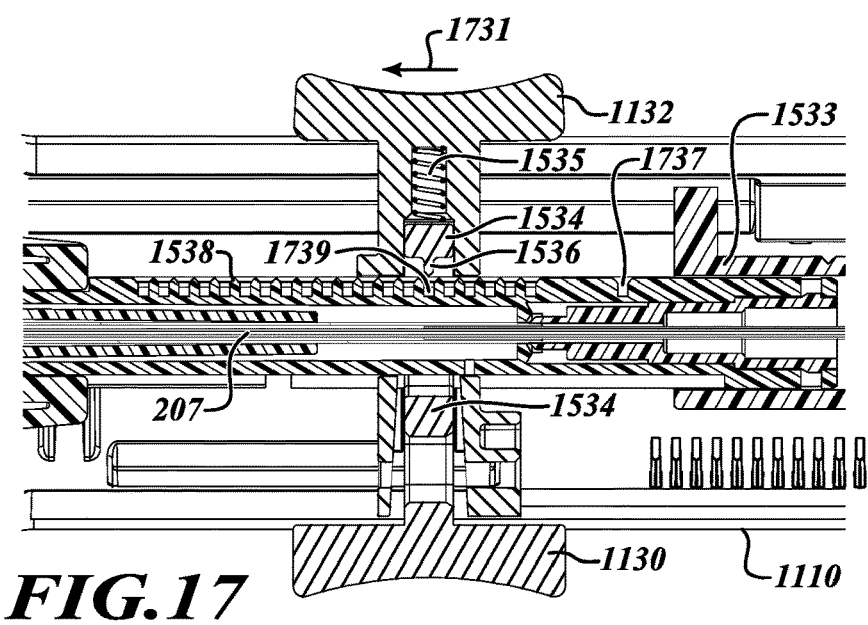
Figure 21:
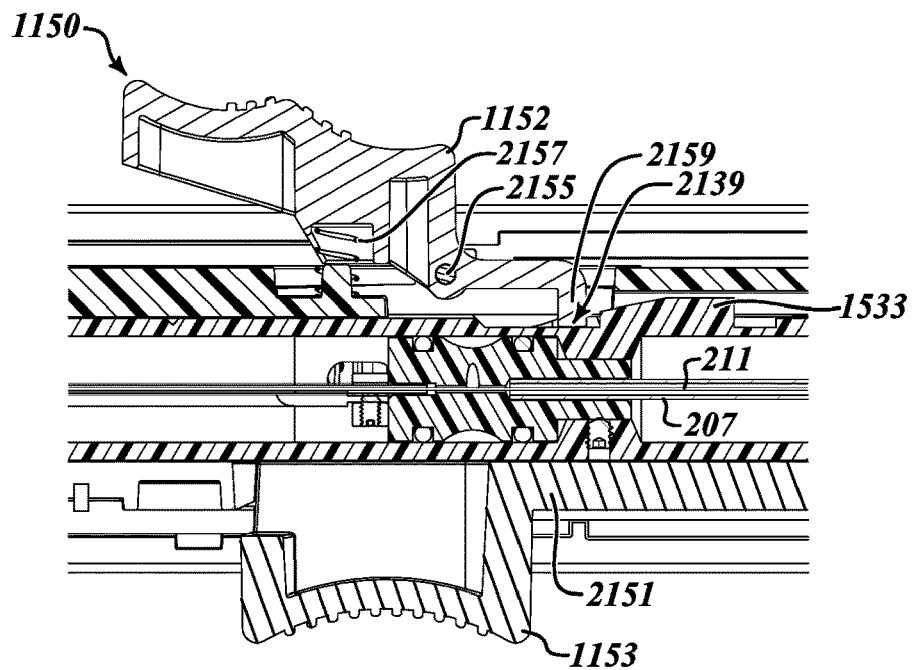
Figure 22:
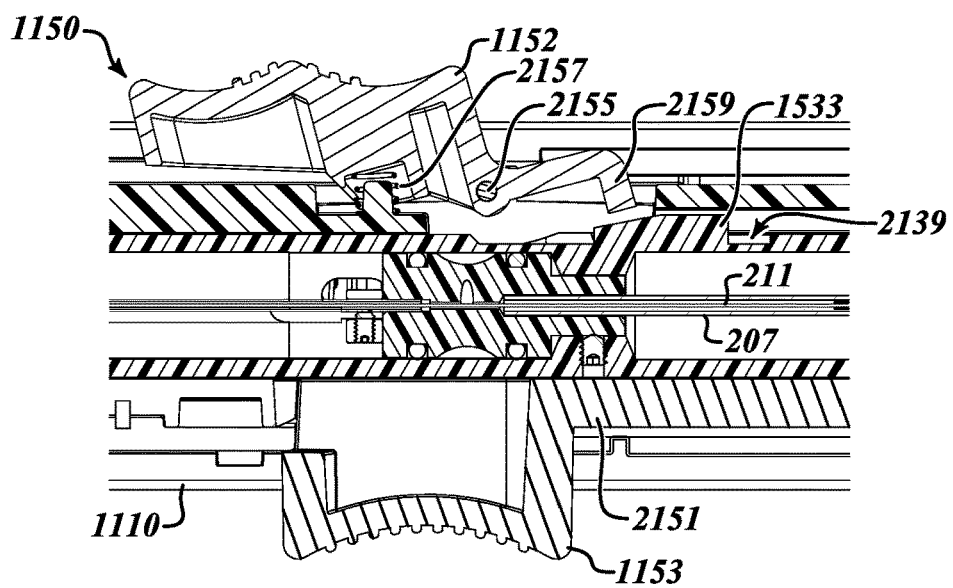
Figure 29:
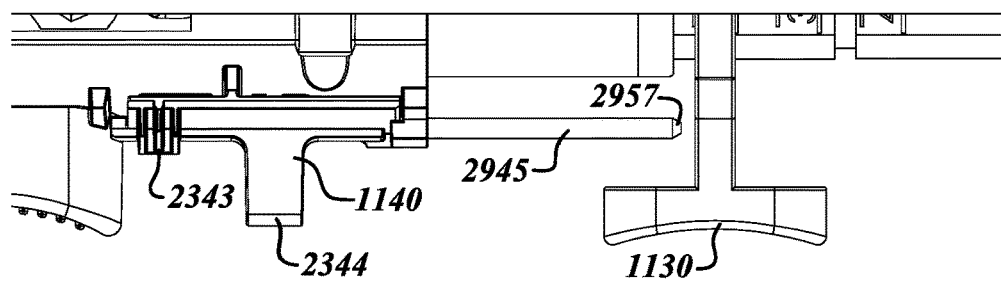
Figure 30:
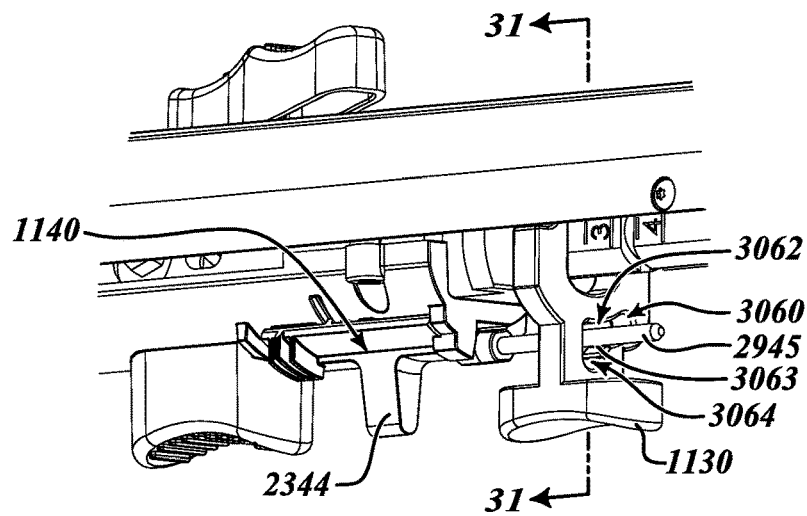
Figure 31:
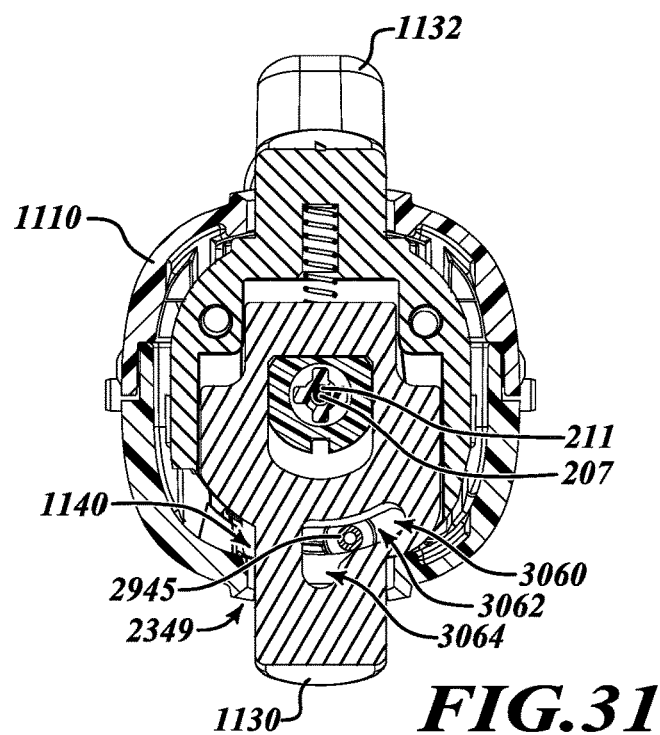
Figure 37A:
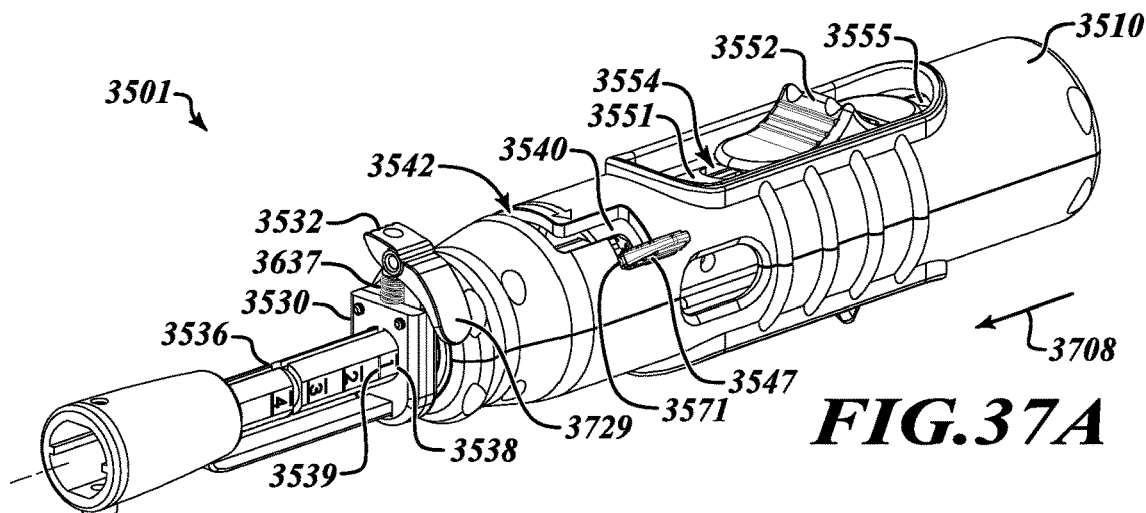
Figure 37B:
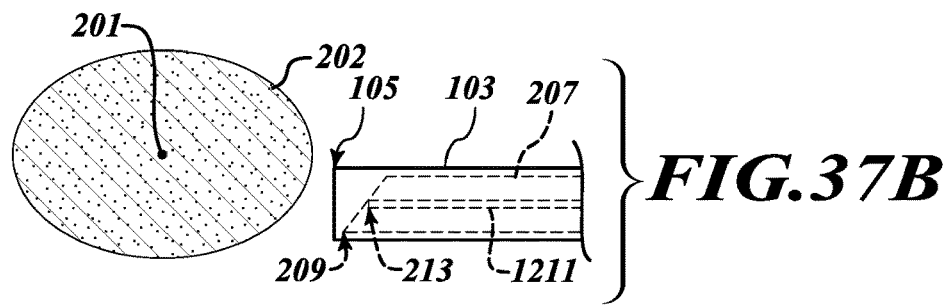
Figure 38A:
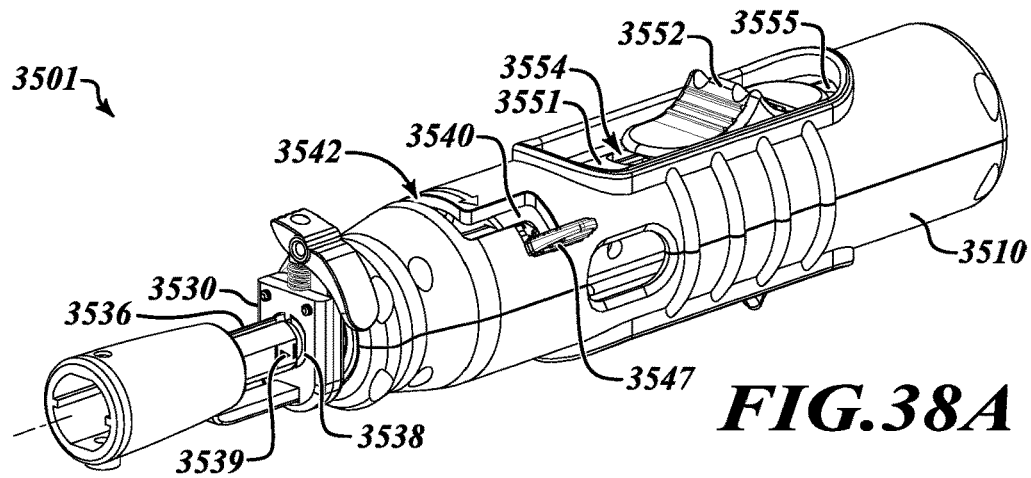
Figure 38B:
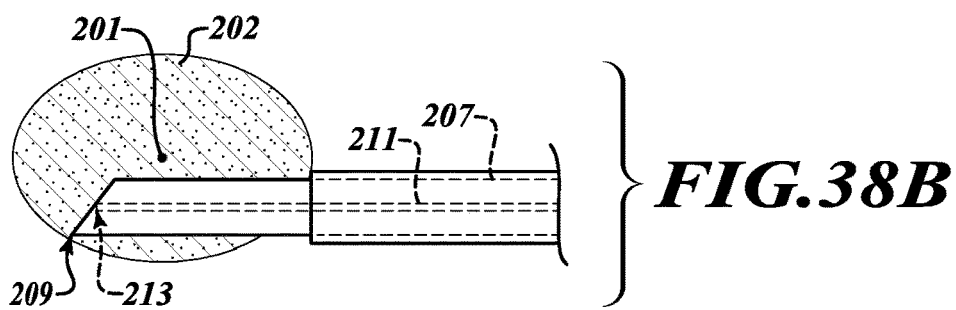
Figure 39:
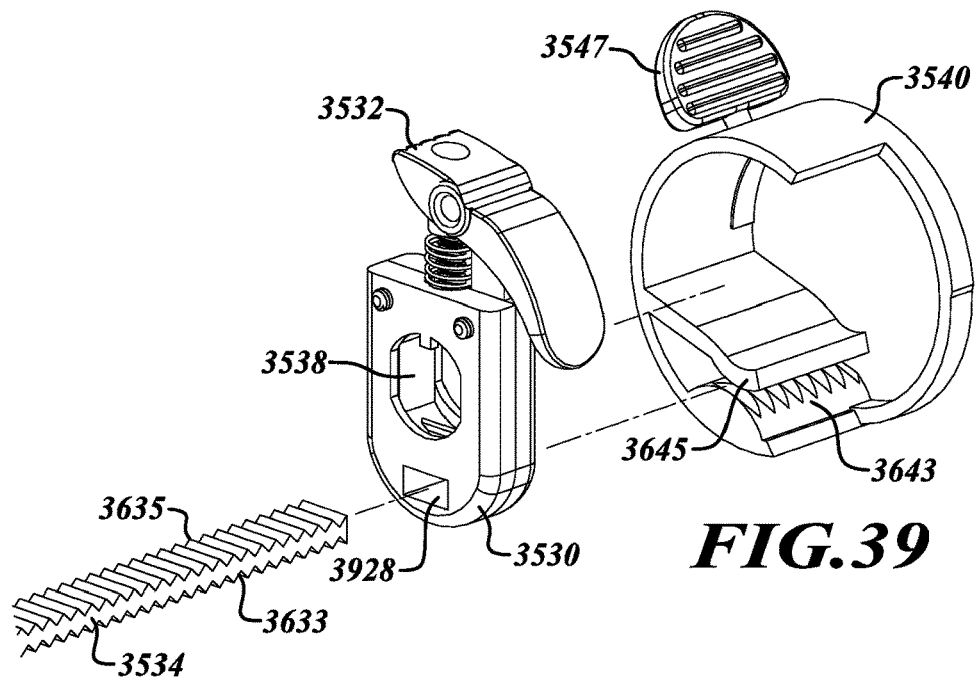
Figure 40:
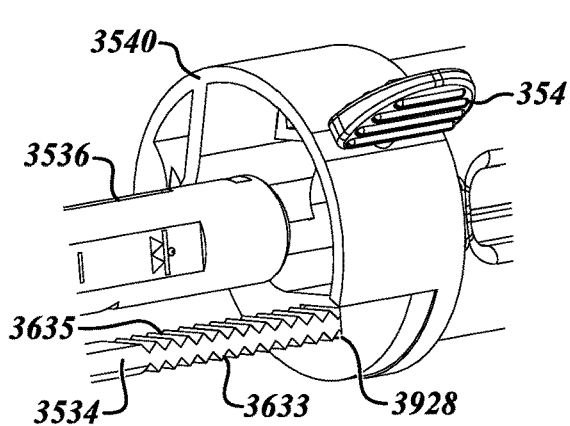
Figure 41:
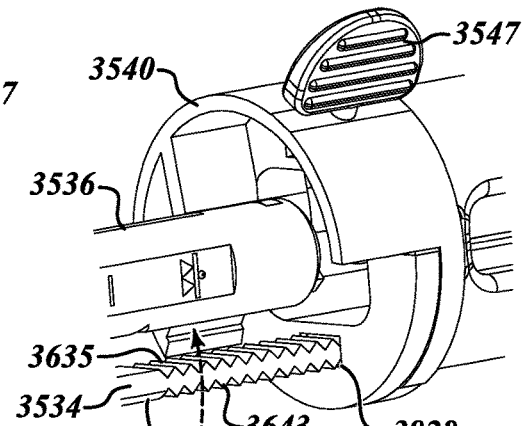
Figure 42:
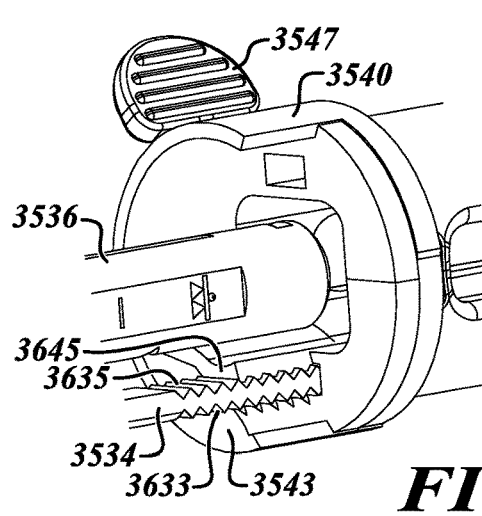
Figure 62:
Figure 63A:
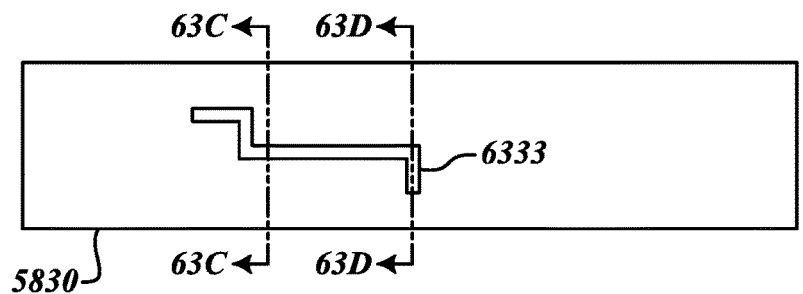
Figure 63B:
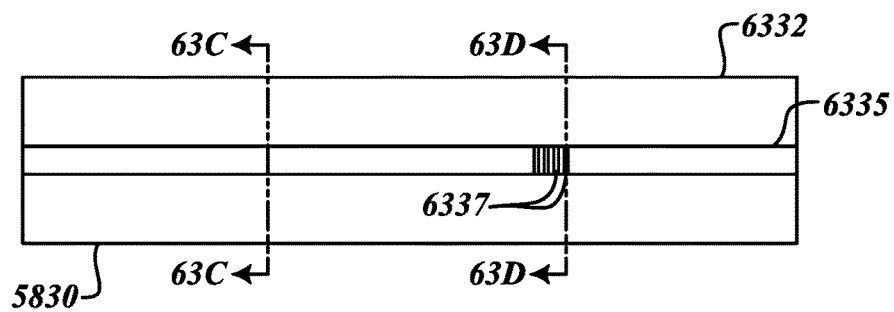
Figure 63C:
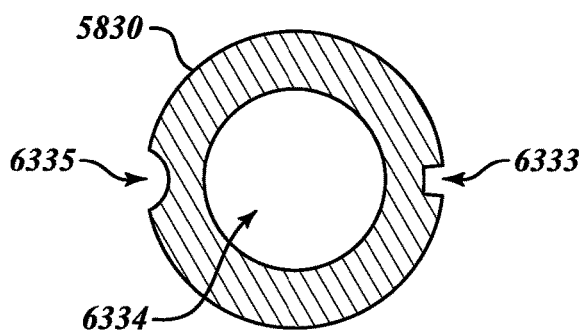
Figure 63D:
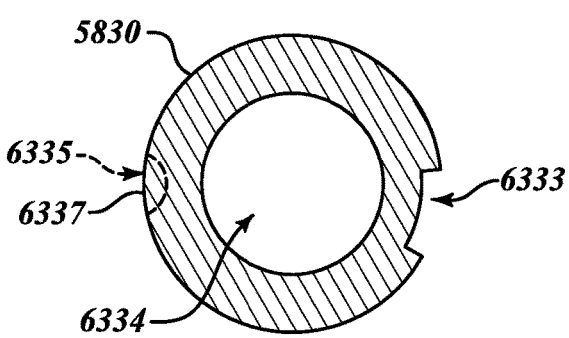
Figure 64A:
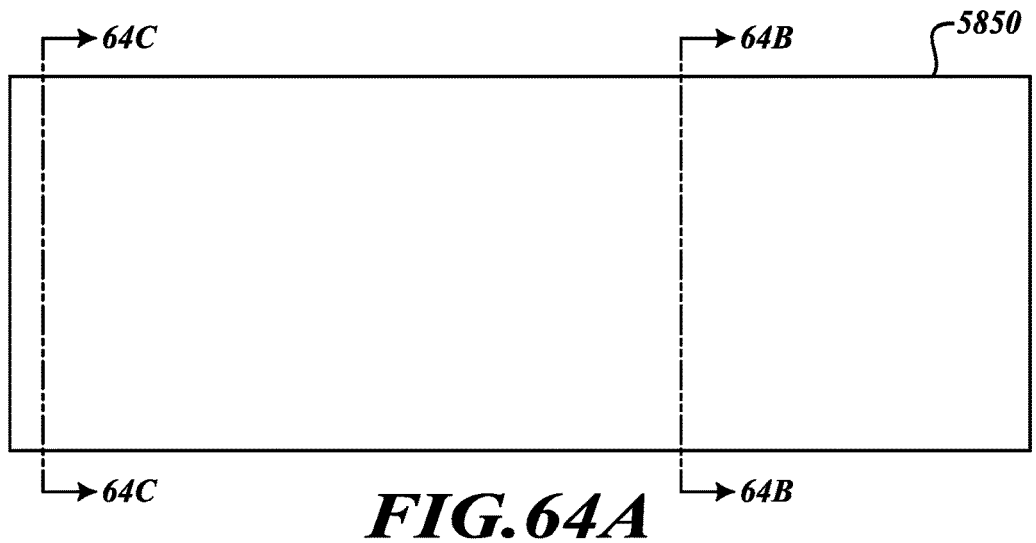
Figure 64B:
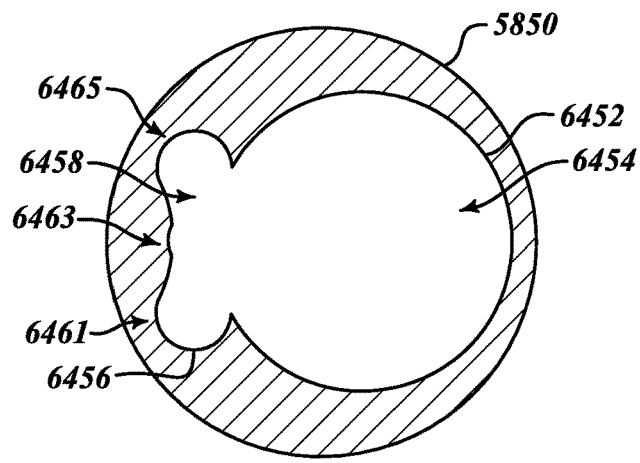
Figure 64C:
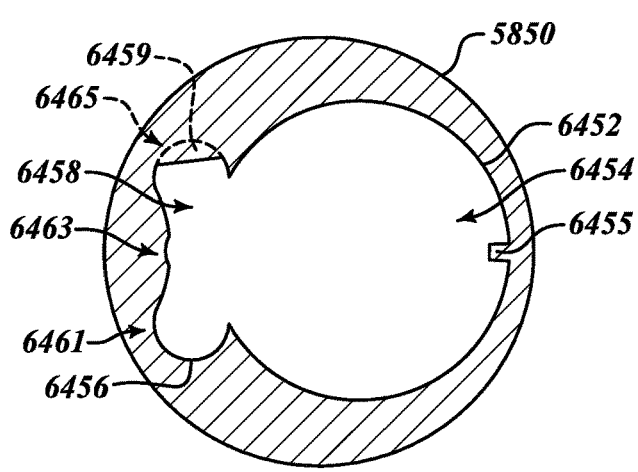

FIGS. 11, 12A, 13A, 14A, 18A, 19A, 20A, 32A, 33A, and 34A are side views of an embodiment of a user interface for positioning multiple components relative to the reference point;

FIGS. 12B, 13B, 14B, 18B, 19B, 20B, 32B, 33B, and 34B are schematic diagrams of positioning of distal ends of a sheath, primary electrode, and secondary electrode relative to a reference point corresponding to positions of the components of the user interface of FIGS. 12A, 13A, 14A, 18A, 19A, 20A, 32A, 33A, and 34A, respectively;

FIGS. 15-17 are cutaway views of the primary actuator and the primary release of the user interface of FIG. 11;

FIGS. 21 and 22 are cutaway views of the secondary actuator and the secondary release of the user interface of FIG. 11;

FIG. 23 is a partial bottom view of the user interface of FIG. 11 showing the actuator interlock in a first position;

FIG. 24 is another partial bottom view of the user interface of FIG. 11 showing the actuator interlock in the first position corresponding to the position of the actuator interlock of FIG. 23;

FIG. 25 is a cross-sectional view of the user interface of FIG. 11 showing the actuator interlock in the first position corresponding to the position of the actuator interlock of FIGS. 23 and 24;

FIG. 26 is a partial bottom view of the user interface of FIG. 11 showing the actuator interlock in a second position;

FIG. 27 is another partial bottom view of the user interface of FIG. 11 showing the actuator interlock in the second position corresponding to the position of the actuator interlock of FIG. 26;

FIG. 28 is a cross-sectional view of the user interface of FIG. 11 showing the actuator interlock in the second position corresponding to the position of the actuator interlock of FIGS. 26 and 27;

FIG. 29 is a partial cutaway side view of the user interface of FIG. 11 illustrating the actuator interlock in a second position to enable use of the primary release;

FIG. 30 is a partial cutaway perspective view of the user interface of FIG. 11 illustrating the actuator interlock in the second position to enable use of the primary release;

FIG. 31 is a cross-sectional view of the user interface of FIG. 11 showing the actuator interlock in the second position corresponding to the position of the actuator interlock of FIG. 30 to enable use of the primary release;

FIG. 35 is a perspective view of another embodiment of a user interface for positioning multiple components relative to the reference point;

FIG. 36 is an exploded view of the user interface of FIG. 35;

FIGS. 37A and 38A are perspective views of the user interface of FIG. 35 for positioning multiple components relative to the reference point;

FIGS. 37B and 38B are schematic diagrams of positioning of distal ends of a sheath, primary electrode, and secondary electrode relative to the reference point corresponding to positions of the primary release and a housing of the user interface of FIGS. 37A and 38A, respectively;

FIG. 39 is an exploded view of the latch and the interlock lever of the user interface of FIG. 35;

FIGS. 40-42 are partial perspective views of the user interface of FIG. 35 illustrating positions of the interlock lever of the user interface of FIG. 35;

FIGS. 43A, 44A, 45A, 46A, and 47A are partial top views of the user interface of FIG. 35;

FIGS. 43B, 44B, 45B, 46B, and 47B are partial side views of the user interface of FIG. 35 corresponding with the partial top views of FIGS. 43A, 44A, 45A, 46A, and 47A, respectively;

FIGS. 43C, 44C, 45C, 46C, and 47C are schematic diagrams of positioning of distal ends of the sheath, primary electrode, and secondary electrode relative to the reference point corresponding to positions of the user interface shown in FIGS. 43A-43B, 44A-44B, 45A-45B, 46A-46B, and 47A-47B, respectively;

FIG. 48 is a side view of another embodiment of a user interface for positioning multiple components relative to a reference point;

FIG. 49 is an exploded view of the user interface of FIG. 48;

FIGS. 50A and 51A are side views of the user interface of FIG. 48 being manipulated to position a sheath;

FIGS. 50B and 51B are schematic diagrams of positioning of distal ends of the sheath, primary electrode, and secondary electrode relative to a reference point corresponding to positions of the sheath actuator of FIGS. 50A and 51A, respectively;

FIGS. 52A, 53A, 54A, 55A, 56A, and 57A are side views of the user interface of FIG. 48 being used to position electrodes within a body;

FIGS. 52B, 53B, 54B, 55B, 56B, and 57B are cross-sectional views of the user interface of FIG. 48 corresponding with the side views of FIGS. 52A, 53A, 54A, 55A, 56A, and 57A, respectively;

FIGS. 52C, 53C, 54C, 55C, 56C, and 57C are schematic diagrams of positioning of distal ends of the sheath, primary electrode, and secondary electrode relative to the reference point corresponding to positions of the user interface shown in FIGS. 52A-52B, 53A-53B, 54A-54B, 55A-55B, 56A-56B, and 57A-57B, respectively;

FIG. 58 is a side view of another embodiment of a user interface for positioning multiple components relative to a reference point;

FIG. 59 is a partial cutaway view of the user interface of FIG. 58;

FIGS. 60A and 61A are side views of the user interface of FIG. 58 being manipulated to position a sheath;

FIGS. 60B and 61B are schematic diagrams of positioning of distal ends of the sheath, primary electrode, and secondary electrode relative to a reference point corresponding to positions of the sheath actuator of FIGS. 60A and 61A, respectively;

FIG. 62 is a side view of a lock rod of the user interface of FIG. 58;

FIG. 63A is a side view of a primary housing of the user interface of FIG. 58;

FIG. 63B is a bottom view of the primary housing of the user interface of FIG. 58;

FIGS. 63C and 63D are cross-sectional views of the primary housing of the user interface of FIG. 58;

FIG. 64A is a side view of the secondary housing of the user interface of FIG. 58;

FIGS. 64B and 64C are cross-sectional views of the secondary housing of the user interface of FIG. 58;

FIGS. 65A, 66A, 67A, 68A, 69A, and 70A are partial cutaway side views of the user interface of FIG. 58 being used to position electrodes within a body;

FIGS. 65B-65C, 66B-66C, 67B-67C, 68B-68C, 69B-69C, and 70B-70C are cross-sectional views of the user interface of FIG. 58 corresponding with the partial cutaway side views of FIGS. 65A, 66A, 67A, 68A, 69A, and 70A, respectively;

FIGS. 65D, 66D, 67D, 68D, 69D, and 70D are schematic diagrams of positioning of distal ends of the sheath, primary electrode, and secondary electrode relative to the reference point corresponding to positions of the user interface shown in FIGS. 65A-65C, 66A-66C, 67A-67C, 68A-68C, 69A-69C, and 70A-70C, respectively;

FIGS. 71A, 72A, 73A, 74A, 75A, and 76A are side views of the user interface of FIG. 58 being manipulated to position multiple components relative to a reference point;

FIGS. 71B, 72B, 73B, 74B, 75B, and 76B are schematic diagrams of positioning of distal ends of the sheath, primary electrode, and secondary electrode relative to the reference point corresponding to positions of the user interface shown in FIGS. 71A, 72A, 73A, 74A, 75A, and 76A, respectively; and FIGS. 77-81 are flow diagrams of illustrative methods of positioning components using a user interface.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes adjacent a reference point where electrical treatment, such as ablative treatment, is to be applied. For a specific example, the user interfaces and methods of their use may be used for ablating and/or coagulating tissue, removing lesions, and for performing other medical procedures within the lung.

It will be appreciated that various embodiments of user interfaces described herein may help to simplify the process of positioning the electrodes and holding the electrodes in place. As will be described below, various embodiments of the user interface accomplish the selective positioning and locking in place of the electrodes by depressing releases and sliding levers, rotating and sliding a housing, or combinations of sliding levers and rotating housings.

Figure 1:
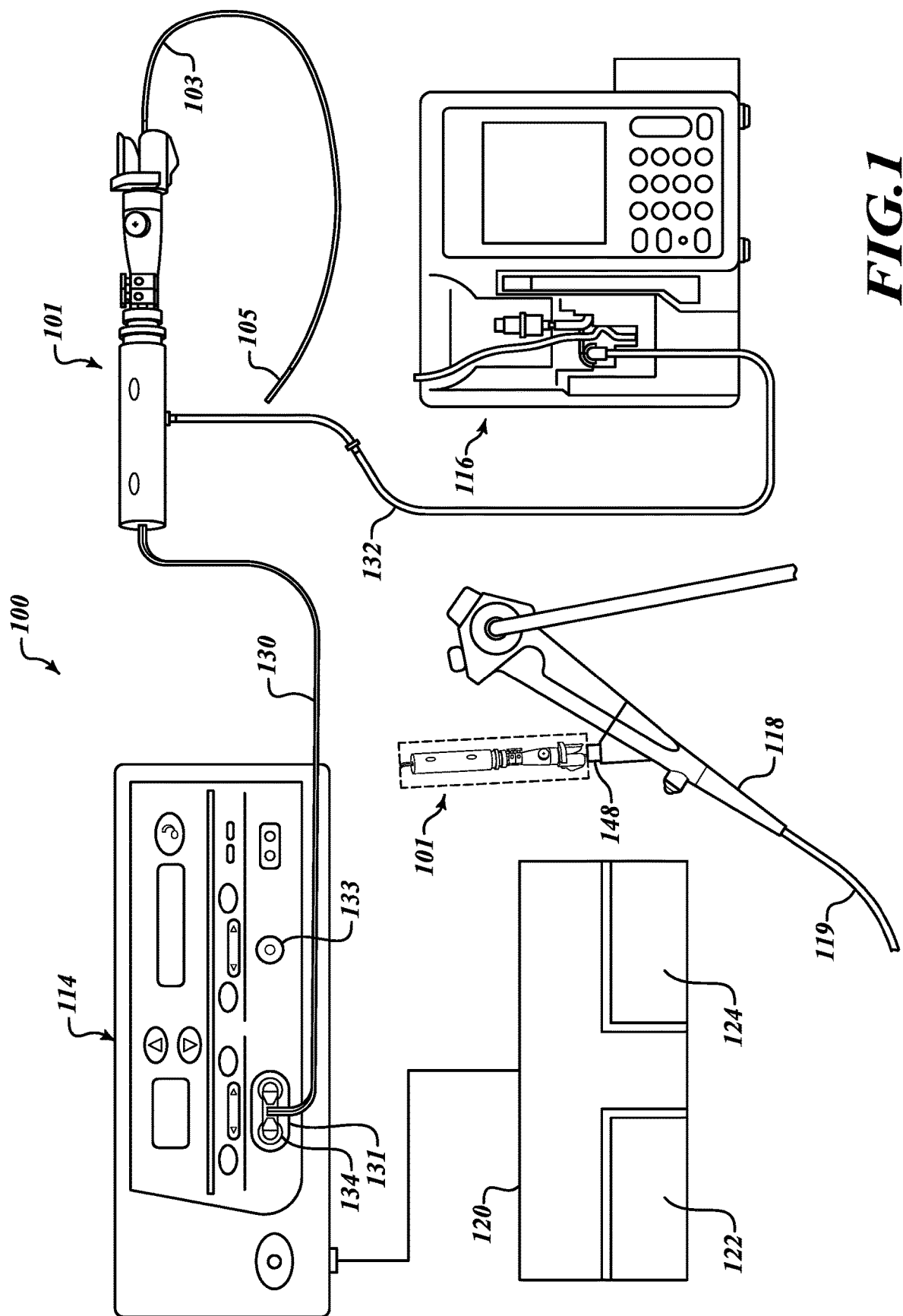
FIG. 1 is a block diagram in partial schematic form of an illustrative system for treating tissue.

Referring to FIG. 1, a system 100 is provided for treating tissue at a reference point in an anatomical region of a patient (not shown in FIG. 1). The system 100 may be a bipolar or monopolar radio frequency (RF) system, as desired, for treating tissue in a patient. Specifically, the system 100 may be employed for coagulation and/or ablation of soft tissue during percutaneous and/or endoscopic, including bronchoscopic, surgical procedures, such as, for example, partial and/or complete ablation of cancerous and/or noncancerous organ lesions. As will be further described, the tissue is treated by positioning one or more electrodes proximate the tissue to be treated and passing an electrical current through the tissue at a reference point.

In some embodiments, the system 100 includes a user interface 101, an electrosurgical radio frequency (RF) generator operating as a switchable current source 114, an infusion pump 116, and an electrosurgical instrument or apparatus, such as without limitation a bronchoscope 118. It will be appreciated that the electrosurgical instrument or apparatus may also include an endoscope or any other electrosurgical instrument as desired for a particular application. The bronchoscope 118 may be configured to receive the user interface 101 at a port 148 to enable the user interface 101 to manipulate electrodes at the reference point via the bronchoscope 118.

The user interface 101 electrically communicates with the switchable current source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. In some other embodiments, the system 100 can be operated in a monopolar mode when the electrical conductor 130 is connected to a secondary outlet 133 with an adapter (not shown in FIG. 1) as desired. The user interface 101 is further connected to the infusion pump 116 with a tube 132 that facilitates the flow of liquid, for example saline solution, from the infusion pump 116 to the user interface 101.

The switchable current source 114 can be operated with the use of a foot operated unit 120 electrically connected to the switchable current source 114. The foot operated unit 120 includes a pedal 122 that instructs the switchable current source 114 to apply an electrical current to electrode(s) (described below) to cut and/or ablate tissue and a pedal 124 that instructs the generator 114 to apply a lower electrical current to the electrode(s) to coagulate tissue.

In various embodiments the bronchoscope 118 includes an insertion tube 119 that permits insertion of a sheath 103 into a body (not shown). A distal end 105 of the sheath 103 is delivered to a location near the tissue to be treated at the reference point. The sheath 103 contains and conveys the electrodes (not shown) to a desired treatment location. Positioning of the distal end 105 of the sheath 103 and the distal ends of the electrodes (not shown in FIG. 1) may be controlled by the user interface 101 received by the bronchoscope 118 at a port 148.

Referring to FIGS. 2-6, distal ends of components are positioned relative to a reference point 201 using various embodiments of a user interface. The reference point 201, for example, may be at a point within a target tissue 202 such as a lesion or any portion of tissue to be treated within a body. Given by way of illustration only and not of limitation, the illustrative embodiments of the user interface described below all are capable of positioning the components as described with reference to FIGS. 2-6, as further described with reference to each of the described embodiments. The description of FIGS. 2-6 is provided as a baseline to describe the operation of the various embodiments of the user interface.

In particular embodiments, a secondary electrode 211 is slidably received within a primary electrode 207, and the primary electrode 207 is slidably received within a sheath 203. In particular embodiments, until a user interface is manipulated to separately move the primary electrode 207 and/or the secondary electrode 211, the primary electrode 207 and the secondary electrode 211 move in concert with the sheath 203, which means that the electrodes 207 and 211 move at a same time and through a same distance as the sheath 203. As will be described below, in some instances, the secondary electrode 211 also may move in concert with the primary electrode 209 while both electrodes move independently of the sheath 103. Components contained within other components are represented with dashed lines in FIGS. 2-6.

Figure 2:
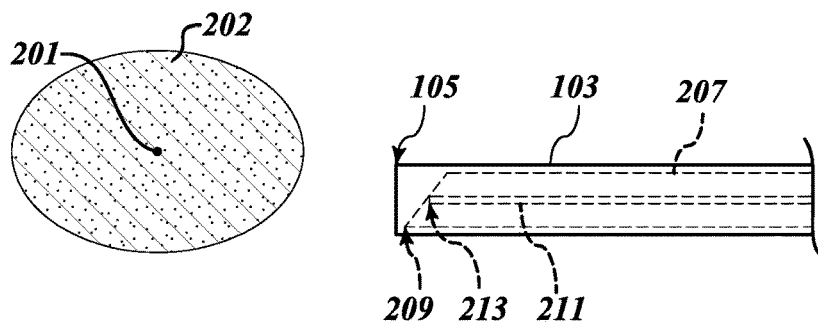
FIGS. 2-6 are schematic diagrams of positioning of distal ends of a sheath, primary electrode, and secondary electrode relative to a reference point.

Referring to FIG. 2, the sheath 203, the primary electrode 207, and the secondary electrode 211 are shown as they are positioned at an initial position relative to the reference point 201 at or near the target tissue 202. More particularly, FIG. 2 shows the components as they might be positioned upon the insertion of the sheath 203 through an insertion tube in a bronchoscope, such as the insertion tube 119 and the bronchoscope 118 of FIG. 1, before they are moved into precisely desired locations by manipulating the user interface (not shown) as further described below.

A distal end 205 of the sheath 203 is positioned close to the target tissue 202. The primary electrode 207 is slidably received within the sheath 203, with a distal end 209 of the primary electrode 207 at or near the distal end 205 of the sheath. Specifically, FIG. 2, for example, shows the distal end 209 of the primary electrode 207 positioned just short of the distal end 205 of the sheath 203. In turn, the secondary electrode 211 is slidably received within the primary electrode 207, with the distal end 213 of the secondary electrode 211 positioned just within the distal end 209 of the primary electrode 207.

Figure 3:
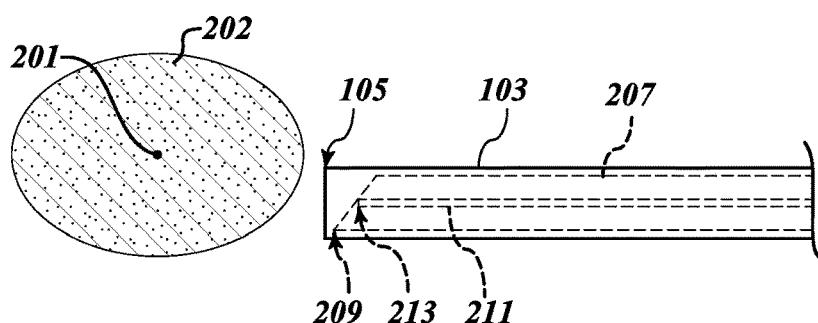

Referring to FIG. 3, the sheath 203, the primary electrode 207, and the secondary electrode 211 are shown as they are positioned once the sheath 203 has been moved closer to the reference point 201. As contrasted with FIG. 2, in FIG. 3, a distal end 205 of the sheath 203 has been moved closer to the reference point 201 at the edge of the target tissue 202. Just as in FIG. 2, because the primary electrode 207 and the secondary electrode 211 have not been separately moved through the manipulation of a user interface (not shown), the primary electrode 207 and the secondary electrode 211 have moved with the movement of the sheath 203. Thus, at the deployment position closer to the reference point 201, the distal end 209 of the primary electrode 207 remains positioned just short of the distal end 205 of the sheath 203. Similarly, the distal end 213 of the secondary electrode 211 remains positioned just within the distal end 209 of the primary electrode 207. As will be further described with reference to embodiments of a sheath lock that may be part of a user interface or used in conjunction with a user interface, once the distal end 205 of the sheath 203 has been moved to a desired location, the sheath 203 may be locked in place.

Figure 4:
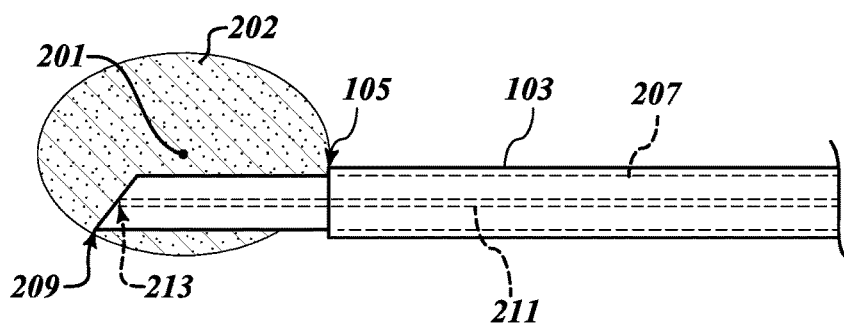

Referring to FIG. 4, the sheath 203, the primary electrode 207, and the secondary electrode 211 are shown as they are positioned once the primary electrode 207 has been extended from the sheath 203 toward the reference point 201 and into the target tissue 202. In particular embodiments, unless the user interface (not shown) is manipulated to disengage movement of the secondary electrode 211 from movement of the primary electrode 207, the secondary electrode 211 moves in concert with the primary electrode 207, with the secondary electrode 211 moving in the same direction and the same distance as the primary electrode 207. Thus, as shown in FIG. 4, the primary electrode 207 as the primary electrode 207 is extended beyond the distal end 105 of the sheath 103, and the secondary electrode 211 moves in concert with the primary electrode 207. As shown in FIG. 4, the distal end 209 of the primary electrode 207 is extended toward the reference point 201 and beyond the distal end 205 of the sheath 203. The distal end 213 of the secondary electrode 211 remains positioned just within the distal end 209 of the primary electrode 207. In particular embodiments, the primary electrode 207 is in the form of a needle, with the distal end 209 being configured to pierce tissue, such as the target tissue 202, to enable the distal end 209 of the primary electrode 207 to reach a desired position, and to be able to situate the secondary electrode 211 at a desired point.

As will be further described below, once the distal end 205 of the sheath 203 is in a desired location and locked in place, embodiments of the user interface allow the primary electrode 207 to be unlocked so that the primary electrode 207 may be moved independently of the sheath 103. As also further described below, embodiments of the user interface may keep motion of the secondary electrode 211 locked with motion of the primary electrode 207 so that the distal end 213 of the secondary electrode 211 moves in concert with the distal end 209 of the primary electrode 207. As also further described below, embodiments of a user interface permit one or both of the primary electrode 207 and the secondary electrode 211 to be fixed in position—that is, remain in place—so that one or both of the electrodes 207 and 211 are secured at a current position. Thus, for example, a position of the primary electrode 207 may be fixed while the secondary electrode 211 may be moved independently of the primary electrode 207, or a position of the secondary electrode 211 may be fixed while the primary electrode 207 may be moved independently of the secondary electrode 211. Also, both electrodes 207 and 211 may be fixed in place, for example, when treatment is administered by applying an electrical current using an electrosurgical apparatus such as that shown in the system 100 of FIG. 1.

Figure 5:
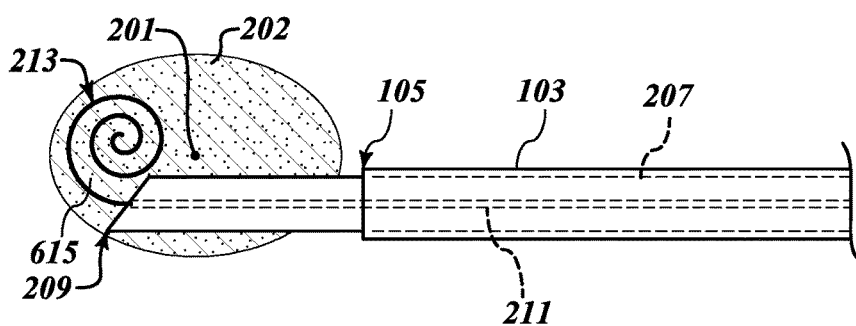

Referring to FIG. 5, the sheath 203, the primary electrode 207, and the secondary electrode 211 are shown as they are positioned once the secondary electrode 211 has been extended from the primary electrode 207. A distal end 213 of the secondary electrode 211 is deployed at a position on an opposite side of the reference point 201 and at an opposite side of the target tissue 202 from the primary electrode 207. In particular embodiments, the secondary electrode 211 is configured as coiled wire which is received within the primary electrode 207 in a straightened form. Once the user interface is manipulated to independently extend the secondary electrode 211 from the primary electrode 207, the secondary electrode 211 coils. As a result, the distal end 213 of the secondary electrode 211 corkscrews into tissue, such as the target tissue 202. The corkscrewing of the distal end 213 of the secondary electrode 211 may assist in securing the position of the distal end 213 of the secondary electrode 211 during treatment. FIG. 5 also shows insulation 615 along a length of the secondary electrode 211, but which stops short of the distal end 213 of the secondary electrode 211. The insulation 615 electrically insulates the secondary electrode 211 from the primary electrode 207 such that, when electrical current is applied to proximal ends (not shown) of the primary electrode 207 and the secondary electrode 211, the electrical current may only flow between the distal end 209 of the primary electrode 207 and the uninsulated distal end 213 of the secondary electrode 211.

Figure 6:
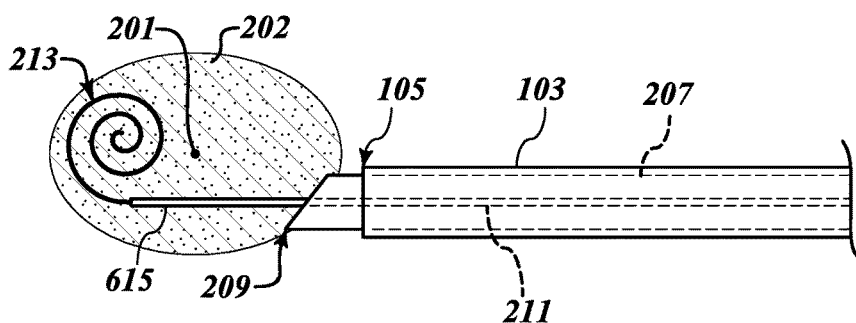

Referring to FIG. 6, the sheath 303, the primary electrode 207, and the secondary electrode 511 are shown as they are positioned once the primary electrode 207 is partially retracted away from the reference point 201 and partially retracted from the target tissue 202 and into the sheath 503. As previously described, a needle shape of the primary electrode 207 assists in positioning the distal end 213 of the secondary electrode 211 at a desired location. Once the distal end 213 of the secondary electrode 211 has been disposed at that location, however, it may be desired to move a distal end 209 of the primary electrode 207 away from the reference point 201 to create a desirable gap between the distal end 213 of the secondary electrode 211 and the distal end 209 of the primary electrode 207 across which electrical current may be applied to treat the target tissue 202 near the reference point 201. As will be described further below, once the distal end 213 of the secondary electrode 211 has been secured at a desirable location, embodiments of the user interface (not shown in FIG. 6) permit the primary electrode 207 to be unlocked and moved independently from the secondary electrode 211 to enable the partial retraction shown in FIG. 6. Once partially retracted, embodiments of the user interface also enable the primary electrode 207 to be locked in place.

Referring to FIGS. 7A and 7B, an apparatus 700 includes an illustrative user interface 701 received at a port 748 of an electrosurgical apparatus 718, such as a bronchoscope or another minimally invasive device used for performing diagnostic or therapeutic tasks by extending a sheath or catheter into a body (not shown in FIGS. 7A and 7B). In the apparatus 700 of FIG. 7A, the user interface 701 includes a sheath actuator 704 and a sheath lock 706 configured to move the sheath 103 to a desired location to position a distal end 105 of the sheath 103 relative to the reference point 201. In some embodiments, the sheath actuator 704 may be a slidable mechanism incorporating a slidable sleeve 712 that is received within a collar 714. The slidable sleeve 712 may be locked in position at the collar 714 by the sheath lock 706. The sheath lock 706 may be a spring loaded locking pin, a thumbscrew, or another mechanism configured to mechanically engage the slidable sleeve 712 to secure the slidable sleeve 712—and, in turn, the sheath 703—in place at a desired location.

In some embodiments, the sheath actuator 704 may be part of the user interface 701. For example, in the user interface 701 of FIG. 7A the slidable sleeve 712 is fixably engaged with an interface housing 710 at a distal end 716 of the interface housing 710. The collar 714 then may engage the port 748 on the electrosurgical apparatus 718, where movement of the slidable sleeve 712 within the collar 714 controls movement of the sheath 103. In some other embodiments, the sheath actuator 704 may, for example, be part of the electrosurgical apparatus 718. The collar 714 may be fixably joined to the port 748. The slidable sleeve 712 may be associated with the port 748 to engage the distal end 716 of the interface housing 710. In another embodiment, the slidable sleeve 712 may be fixably joined to the distal end 716 of the interface housing 710 and be configured to receivably engage the collar 714 that is fixably attached to the port 748. Any of these embodiments of the sheath actuator 704 may facilitate movement of the sheath 103 as described below.

In various embodiments the user interface 701 is mechanically coupled with a primary electrode 207 slidably received within the sheath 103, with a distal end 209 of the primary electrode 207 positioned just short of the distal end 105 of the sheath 103. The user interface 701 is also mechanically coupled with a secondary electrode 211 slidably received within the primary electrode 207, with the distal end 213 of the secondary electrode 211 positioned just within the distal end 209 of the primary electrode 207. Embodiments of the user interface 701 may be configured to secure the primary electrode 207 and the secondary electrode 211 relative to the sheath 103 so that both the primary electrode 207 and the secondary electrode 211 move in concert with the sheath 103 as the sheath is moved as described with reference to FIG. 3.

Referring to FIGS. 8A and 8B, manipulation of the sheath actuator 704 illustrates an example of how the sheath 103 may be unlocked and moved into position as previously described with reference to FIG. 3. In the configuration shown in FIGS. 8A and 8B, the sheath actuator 704 has been manipulated to enable the sheath 103 to be moved a distance 819 closer to the reference point 201 and the target tissue 202. Specifically, once the sheath lock 706 of the sheath actuator 704 is manipulated to enable movement of the slidable sleeve 712 within the collar 714, the interface housing 710 is moved the distance 819 to move the sheath 103 the same distance 819 toward the reference point 702. Once the sheath 103 has reached the desired location, the slidable sleeve 712 may be locked in position at the collar 714 by the sheath lock 706. As will be described further below, embodiments of the user interface 701 maintain the positions of the primary electrode 207 and the secondary electrode 211 relative to the sheath 103 as the sheath actuator 704 is used to move the sheath 103. Therefore, a distal end 209 of the primary electrode 207 and a distal end 213 of the secondary electrode 211 also are moved by the distance 219 toward the reference point 201.

Figure 9:
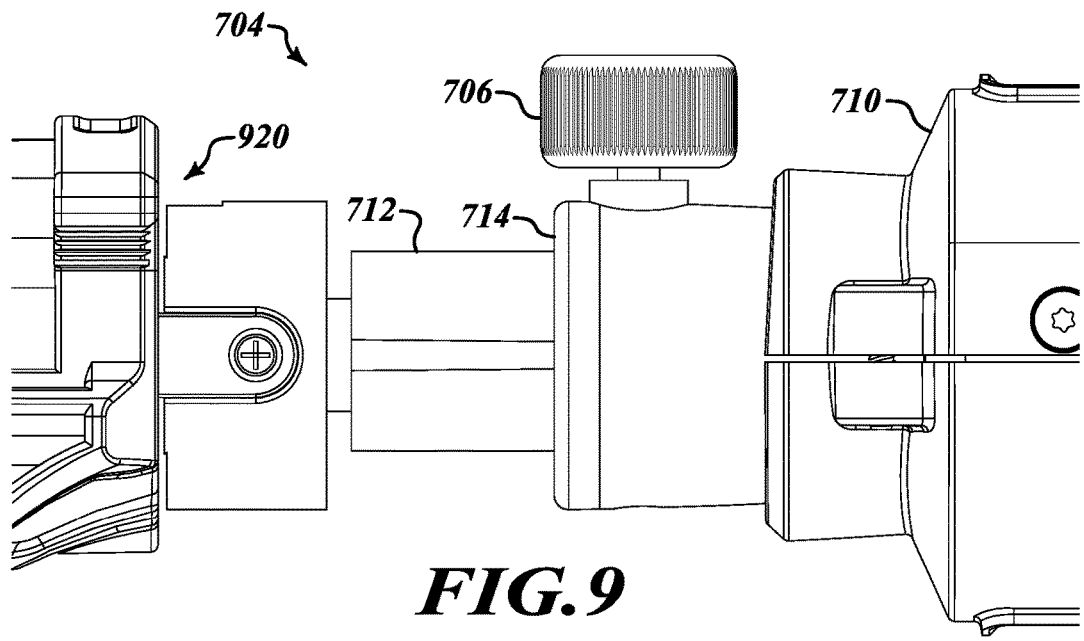
FIG. 9 is a side view of an illustrative sheath actuator and a sheath lock.

Referring to FIG. 9, an enlarged external view shows an illustrative sheath actuator 704 and a sheath lock 706 in greater detail. The sheath actuator 704 includes a slidable sleeve 712 that is fixably attached to a coupling 920 configured to engage a port (not shown in FIG. 9) of an electrosurgical apparatus (not shown in FIG. 9) such as a bronchoscope. The sheath lock 706 in the embodiment of FIG. 9 is a thumbscrew that may be loosened to permit movement of a collar 714 fixably attached to the interface housing 710 to move the sheath (not shown in FIG. 9) as previously described with reference to FIGS. 7 and 8. After the interface housing 710 has been manipulated to slide the collar 714 relative to the slidable sleeve 712 to move the sheath to a desired location, the sheath lock 706 is reengaged, such as by turning a thumbscrew, to fix the position of the sheath.

Figure 10:
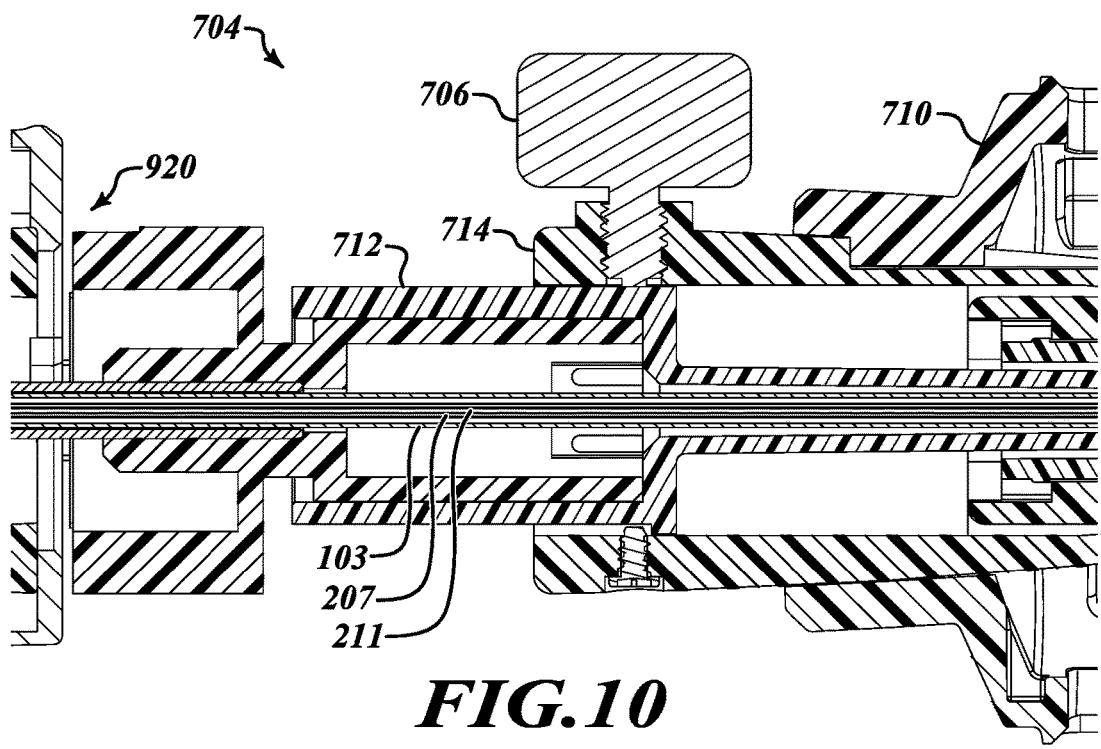
FIG. 10 is a cutaway view of the sheath actuator and sheath lock of FIG. 9.

Referring to FIG. 10, a cutaway view of the illustrative sheath actuator 704 shows internal operation of the sheath actuator 704 of FIG. 9. As previously described, the sheath actuator 704 includes the slidable sleeve 712 that is fixably attached to the coupling 920. In some embodiments the sheath lock 706 is a thumbscrew that may be loosened to permit movement of the collar 714 fixably attached to the interface housing 710 to move the sheath 103 and, in concert therewith, the primary electrode 207 and the secondary electrode 211 received within the sheath 103. After the interface housing 710 is manipulated to slide the collar 714 relative to the slidable sleeve 712 to move the sheath 103 to the desired location, the sheath lock 706 is turned to fix the position of the collar 714 relative to the slidable sleeve 712 to fix the position of the sheath 103.

Referring to FIG. 11, in some embodiments an illustrative user interface 1101 is used to position a sheath 1003, a primary electrode, and secondary electrode relative to a reference point (not shown in FIG. 11). The user interface 1101 includes components that are moved parallel with or transverse to an axis 1121 or rotated about a curve 1123 around the axis 1121, as further described below. The user interface 1101 includes a coupling 1120 and a sheath actuator 1104, including a slidable sleeve 1112 that moves within a collar 1114 fixably attached to the interface housing 1110 when released by a sheath lock 1106 to move the sheath 103, as previously described with reference to FIGS. 9 and 10. The user interface 1101 also receives leads 1122 that provides electrical connections between electrodes and a switchable current source (not shown in FIG. 11), as previously described with reference to FIG. 1. The user interface 1101, as well as other embodiments of the user interface described throughout this description, also receives a source of saline fluid (not shown) that may be passed through the sheath to facilitate the application of electrosurgical treatments. Although not expressly shown in subsequent depictions of other illustrative embodiments of the user interface described with reference to FIGS. 35-75, it will be appreciated that similar leads may be used to provide electrical connections between the electrodes and a switchable current source.

The illustrative user interface 1101 shown in FIG. 11 includes several user controls whose operation and effect are described in further detail in the following figures. A primary release 1130 extends from a lower side 1124 of the housing 1110 and is configured to unlock movement of the primary electrode (not shown) that is moved through manipulation of a primary actuator 1132 extending from an upper side 1126 of the housing 1110. The primary actuator 1132 is mechanically coupled with the primary electrode (not shown in FIG. 11) so that, when the primary actuator 1132 moves relative to the housing 1110, the primary electrode moves relative to the reference point (also not shown in FIG. 11). A depth gauge 1190 on the housing 1110 includes an indicator 1192 to indicate an insertion depth of the primary electrode beyond an end of the sheath (not shown).

A secondary release 1150 is integrated with a secondary actuator 1152 disposed along the upper side 1126 of the housing and is configured to unlock and control movement of the secondary electrode, respectively. The secondary actuator 1152 is fixably coupled with a secondary grip 1153 extending from the lower side 1124 of the housing 1110. The secondary actuator 1152 is mechanically coupled with the secondary electrode (not shown) so that, when the secondary actuator 1152 moves relative to the housing 1110, the secondary electrode moves relative to the reference point (not shown in FIG. 11).

An actuator interlock 1140 positioned along the lower side 1124 of the housing 1110 may restrict movement of the secondary electrode relative to the primary electrode, block use of the primary release 1130, and decouple the secondary electrode (not shown) from the primary electrode, as further described below. As will be shown below, when both the primary actuator 1132 and the secondary actuator 1152 move in concert, the actuator interlock 1140 moves in concert with the primary actuator 1132 and the secondary actuator. As will be further described below, the primary release 1130, the actuator interlock 1140, and the secondary release 1150 enable selective movement of the electrodes in concert and independently to facilitate placement of distal ends of the electrodes within a body.

Figure 12A:
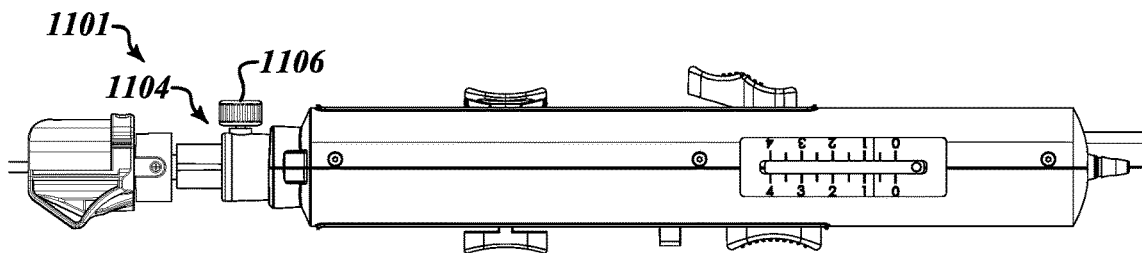
Figure 12B:
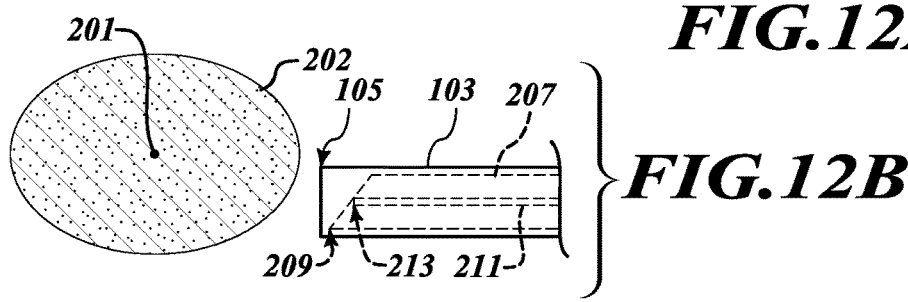

Referring to FIGS. 12A and 12B, in some embodiments the user interface 1101 has an initial deployment configuration once a sheath 103 has been deployed near the reference point 201. As described with reference to FIGS. 7A-10, a sheath actuator 1104 and sheath lock 1106 have been previously engaged to position a distal end 105 of the sheath 103 at a desired location near the reference point 201, as shown in an inset view. As previously described, a primary electrode 207 is received within the sheath 103, with the distal end 209 of the primary electrode 207 initially positioned just short of the distal end 105 of the sheath 103. A secondary electrode 211 is received within the primary electrode 207, with the distal end 213 of the secondary electrode 211 positioned just short of the distal end 209 of the primary electrode 207.

Figure 13A:
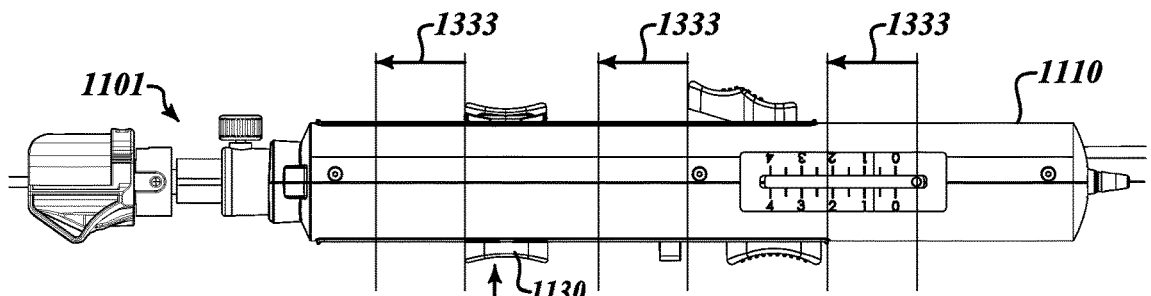
Figure 13B:
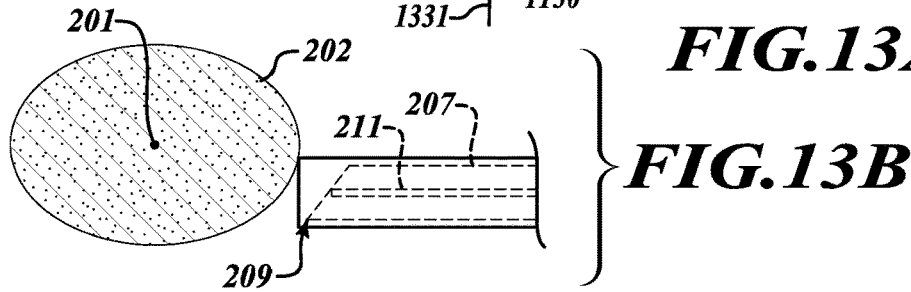

Referring to FIGS. 13A and 13B, in some embodiments of the user interface 1101, the primary release 1130 is engaged to allow the primary electrode 207 to be moved. Specifically, releasing the primary release 1130 is accomplished by depressing the primary release 1130 toward the housing 1110 of the user interface in a direction 1331. Activating the primary release 1130 does not cause movement of the sheath 103 or the electrodes 207 or 211 relative to the reference point 201 as shown in the inset view of FIG. 12B, but only enables movement of the primary electrode 207 which, as further described below, may or may not also move the secondary electrode 211.

Figure 14A:
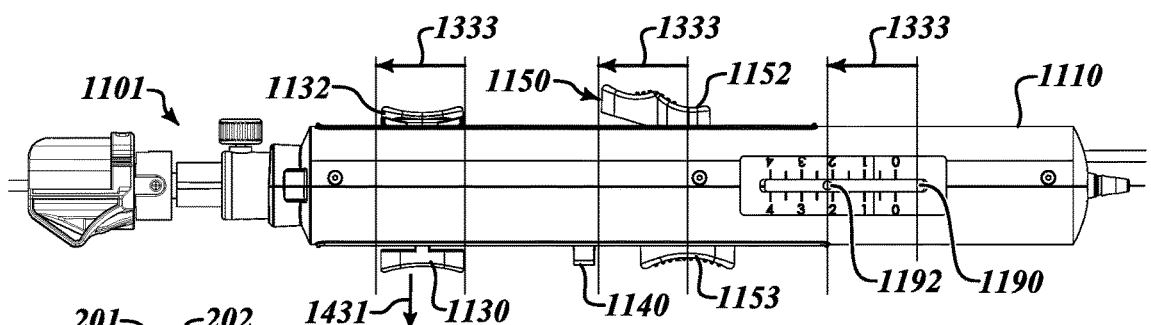
Figure 14B:
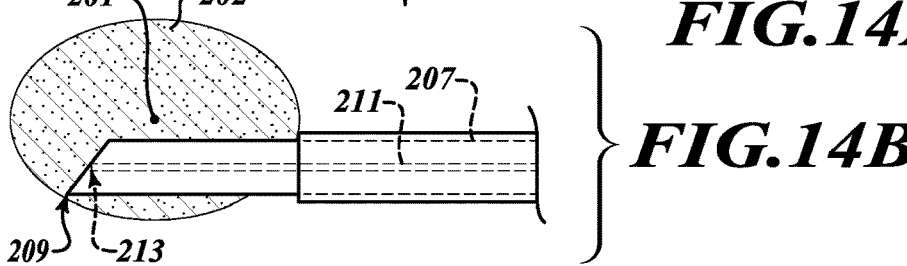

Referring to FIGS. 14A and 14B, the user interface 1101 is shown after a primary actuator 1132 has been moved a distance 1433. After the primary actuator 1132 is moved, the primary release 1130 is disengaged to allow the primary release to move in a direction 1431 away from the housing 1110 to resume its original position as shown with reference to FIG. 12A. Four actions result from the movement of the primary actuator 1132. First, as shown in the inset of FIG. 14B, movement of the primary actuator 1132 extends the primary electrode 207 beyond the distal end 105 of the sheath 103 and into the target tissue 202, thereby positioning the distal end 209 of the primary electrode 207 close to the reference point 201. Second, the secondary electrode 211 moves in concert with the primary electrode 207, with the distal end 213 of the secondary electrode 211 continuing to be positioned just short of the distal end 209 of the secondary electrode 207. Third, the concerted movement of the primary electrode 207 and the secondary electrode 211 is reflected in movements through the same distance 1433 of the actuator interlock 1140, the secondary release 1150, the secondary actuator 1152, and the secondary grip 1153. The primary actuator 1132 and the secondary actuator 1152 are mechanically linked to enable the concerted movement of the primary electrode 207 and the secondary electrode 211, as further described below. Fourth, the indicator 1192 of the depth gauge 1190 also is mechanically coupled to the primary actuator 1132. Thus, the distance 1433 the primary actuator 1132 and the primary electrode 207 are moved is shown on the depth gauge 1190 by the indicator 1192.

Referring to FIG. 15, a primary actuator 1132 and a primary release 1130 may be used in embodiments of the user interface described with reference to FIGS. 11-14B, with the primary release 1130 in a locked position as shown in FIGS. 12A and 14A. The primary actuator 1132 is mechanically coupled with a primary electrode slider 1533 that is mechanically coupled with the primary electrode 207 to move the primary electrode 207 as previously described with reference to FIGS. 2-6 and 12-14. When the primary release 1130 is in a locked position, a lock member 1534 that extends through the inside of the primary actuator 1132 is urged by a biasing member, such as a spring 1535, to force a locking pin 1536 into a starting notch 1537 in a locking rack 1538 within a housing (not shown in FIG. 15) of the user interface of FIGS. 11-14. The locking pin 1536 forcibly engages the starting notch 1537 to prevent movement of the primary actuator 1132, thus also preventing movement of the primary electrode slider 1533 and the primary electrode 207. Thus, with the primary release 1130 in the locked position shown in FIG. 15, the primary electrode slider 1530 and the primary electrode 207 are locked at their current positions.

Referring to FIG. 16, the operation of the primary actuator 1132 and a primary release 1130 are shown with the primary release 1130 engaged to enable movement of the primary actuator 1132. When a force is applied to the primary release 1130 to move the primary actuator 1132 in a direction 1631, the primary release 1130 causes the lock member 1534 to move in the direction 1631, compressing the spring 1535 and moving the locking pin 1536 out of the starting notch 1537 to enable movement of the primary actuator 1132. In other words, pressing the primary release 1130 frees the locking pin 1536 from the starting notch 1537 of the locking rack 1538 to allow the primary actuator 1132 to move the primary electrode slider 1533.

Referring to FIG. 17, the operation of a primary actuator 1132 in moving the primary electrode slider 1533 and the primary electrode 207 is shown while the primary release 1130 remains engaged to enable movement of the primary actuator 1132. As shown with reference to FIG. 16, enabling release of the locking pin 1536 from the starting notch 1537 by the primary actuator 1132 causes the lock member 1534 to compress the spring 1535 to allow the primary actuator 1132 and, thus, the primary electrode slider 1533 and the primary electrode 207, to move in a direction 1731 relative to the housing 1110. The force applied to the primary release 1130 continues to cause the lock member 1534 to compress the spring 1535 and thus allows the locking pin 1536 to move relative to the locking rack 1538 where, if released in the position shown in FIG. 17, the locking pin 1536 would be allowed to engage a selected notch 1739 in the locking rack 1538. It should be noted that the primary release 1130 moves in concert with the primary actuator 1132 as the primary actuator 1132 is moved relative to the housing 1110. Thus, only the starting notch 1537, the locking rack 1538, and the housing 1110 remain in the same position in the embodiment of FIG. 17.

Upon release of the primary release 1130, pressure previously applied by the lock member 1534 on the spring 1535 is released. As a result, the spring 1535 presses against the lock member 1534 and, in turn, causes the locking pin 1536 to engage the selected notch 1739 in the locking rack 1538. Then, similar to the configuration shown in FIG. 15, the primary electrode slider 1530 and the primary electrode 207 are then locked at a new position relative to the housing 1110 which also would move a distal end (not shown in FIG. 15) of the primary electrode 207 in a body (also not shown in FIG. 17).

Referring to FIGS. 18A and 18B, in some embodiments the primary electrode 207 has been deployed with the distal end 209 near the reference point 201 and locked in position as shown in FIG. 14B just before the secondary release 1150 is engaged to unlock movement of the secondary electrode 211. The secondary release 1150 is integrated with the secondary actuator 1152. Specifically, the secondary release 1150 constitutes an end of the secondary actuator 1152 that may be depressed in a direction 1831 that partially rotates the secondary actuator 1152 downward toward the interface housing 1110 to disengage the secondary actuator 1152 from the primary electrode slider (not shown in FIG. 18A). Disengagement of the secondary actuator 1152 permits the secondary actuator 1152 and a fixably coupled secondary grip 1153 to be moved independently of the primary actuator 1132 to enable the secondary electrode 211 to be moved independently of the primary electrode 207 toward the reference point 102. Operation of the secondary release 1152 to disengage the secondary actuator 1150 from the primary electrode slider is further described with reference to FIGS. 21 and 22.

Referring to FIGS. 19A and 19B, in some embodiments of the user interface 1101, the secondary release 1150 may be depressed to partially rotate the secondary actuator 1152 toward the interface housing 1110 to permit movement of the secondary actuator 1152 independent of the primary actuator 1132. Although the secondary actuator 1152 is unlocked by depressing the secondary release 1150, the secondary actuator 1152 and the associated secondary grip 1153 have not yet been moved. Thus, the distal end 213 of the secondary electrode 211 has not yet been moved relative to the distal end 209 of the primary electrode 207 toward the reference point 201, as shown in the inset view.

Referring to FIGS. 20A and 20B, the secondary actuator 1152 has been moved a distance 2033 to extend the distal end 213 of the secondary electrode 211 beyond the distal end 209 of the primary electrode 207 and beyond the reference point 201. The secondary actuator 1152 is fixably engaged with a secondary grip 1153. Thus, the secondary grip 1153 also moves the distance 2033. Fixably engaging the secondary actuator 1152 with the secondary grip 1153 enables a user (not shown) to apply more force in extending the secondary electrode 211 than may be possible if the user only were able to apply force on one side of the interface housing 1110 to move the secondary actuator 1152. This may be valuable if, for example, the distal end 213 of the secondary electrode 211 were being forced into tissue (not shown) such that a coiled shape of the distal end 213 of the secondary electrode 211 may corkscrew into the tissue to anchor the distal end 213 of the secondary electrode 211 in the tissue. With the secondary actuator 1152 having been moved to extend the distal end 213 of the secondary electrode 211, the secondary release 1150 is released to lock the position of the secondary actuator 1152 and, thus, to lock the position of the secondary electrode 211.

As the secondary actuator 1152 moves through the distance 2033, the actuator interlock 1140 also moves forward by the distance 2033. The term "forward," as used in this description, describes a direction toward a coupling 1120 (FIG. 11) where the user interface engages a port of an electrosurgical apparatus, such as the port 748 of bronchoscope 718 of FIGS. 7 and 8. In the FIGURES to follow, the forward direction consistently is positioned either toward the left-hand side of the FIGURE or coming out of the FIGURE. As further described below, the forward travel of the secondary actuator 1152 and the secondary grip 1153 is arrested when the actuator interlock 1140 abuts the primary release 1130 (and, thus, the coupled primary actuator 1132) and the secondary grip 1153 (and, thus, the coupled secondary actuator 1152). In various embodiments, for example, a pin (not shown) on a forward end of the primary electrode slider 1533 may reach an end of a slot on the actuator interlock 1140 that, in turn, stops the movement of the secondary actuator 1152 and the secondary grip 1153. Thus, the actuator interlock 1140 serves to limit the travel of the secondary actuator 1152 and, thus, a length by which the distal end 213 of the secondary electrode 211 may be extended beyond the distal end 209 of the primary electrode 207. A configuration of the actuator interlock 1140 and the operation of the actuator interlock is explained with reference to FIGS. 23-31.

Referring to FIG. 21, a secondary release 1150 and a secondary actuator 1152 are shown in a locked position. When the secondary release 1150 is in a locked position, the secondary electrode 211 moves in concert with the primary electrode 207 as previously described with reference to FIGS. 12-17. As previously described, the secondary release 1150 is integrated with the secondary actuator 1152 in the embodiment of FIG. 21. The secondary actuator 1152 is rotatably mounted to a secondary electrode slider 2151 at a pivot 2155. A spring 2157 maintains the secondary release 2150 in the locked position when the secondary release 1150 is not being depressed. A secondary grip 1153 is fixably coupled to the secondary electrode slider 2151 and moves (or does not move, as the case may be) in concert with the secondary actuator 1152. When the secondary release 1150 is in the locked position, a locking arm 2159 engages a locking notch 2139 in the primary electrode slider 1533. As shown in FIG. 21, the secondary electrode 211 is in an extended position in which the primary actuator 1132 and the secondary actuator 1152 no longer move in concert.

Referring to FIG. 22, a secondary release 1150 and a secondary actuator 1152 are shown in an unlocked position. As previously described with reference to FIG. 19, the secondary release 1150 is unlocked by depressing the secondary release 1150, thereby causing the secondary actuator 1152 to deform the spring 2157 and, thus, causing the secondary actuator 1152 to rotate about the pivot 2155 into an unlocked position. With the secondary actuator 1152 rotated into the unlocked position, the locking arm 2159 is withdrawn from the locking notch 2139, thereby enabling the secondary actuator 1152 to move. Then, by applying force to the secondary actuator 1152 and/or the secondary grip 1153, an operator (not shown in FIG. 22) can extend a secondary electrode 211 independently of the primary electrode 207 as previously described with reference to FIGS. 18-20.

According to various embodiments of the present disclosure and as previously described with reference to FIGS. 4 and 12-14, it may be desirable to selectively enable the primary electrode and the secondary electrode to move in concert. However, as described with reference to FIG. 6, once the secondary electrode is deployed, it may be desirable to partially withdraw the primary electrode while maintaining the position of the secondary electrode. Referring again to FIG. 4, the distal end 209 of the primary electrode 207 may be needle-shaped in order to pierce tissue at or adjacent the reference point 201. The secondary electrode 211 is moved in concert with the primary electrode 207, thereby positioning the distal end 213 of the secondary electrode closer to the reference point 201. Referring to FIG. 5, the piercing capability provided by this illustrative configuration of the primary electrode 207 may be useful to deploy the distal end 213 of the secondary electrode 211 at a desired location relative to the reference point 201.

However, once the position of the primary electrode 207 has been exploited to deploy the distal end 213 of the secondary electrode 211, with reference to FIG. 6, it may be desirable to partially retract the distal end 209 of the primary electrode 207 to apply an electrical current over a distance between the distal end 213 of the secondary electrode 211 and the distal end 209 of the secondary electrode 207. Providing a selective degree of movement of the distal end 213 of the secondary electrode 211 independent of the primary electrode 207, as shown in FIG. 6, as well as maintaining the distal end 213 of the secondary electrode 211 when the distal end 209 of the primary electrode 207 is partially withdrawn, is controlled by the actuator interlock 1140 working in concert with the primary actuator and the secondary actuator as further described below with reference to FIGS. 23-31.

Referring to FIG. 23, the actuator interlock 1140 is shown as situated within the housing 1110 of the user interface. Specifically, the actuator interlock 1140 is positioned between the secondary grip 1153 (which moves in concert with the secondary actuator, as previously described with reference to FIGS. 18-22) and the primary release 1130 (which moves in concert with the primary actuator 1132, as previously described with reference to FIGS. 12-17). Portions of the primary release 1130, the actuator interlock 1140, and the secondary grip 1153 extend from the housing 1110 through a channel 2349 on an underside of the housing 1110. As previously described with reference to FIGS. 21 and 22, the secondary actuator 1152 engages the primary electrode slider 1533 to cause the secondary electrode slider 2151 to move in concert with the primary electrode slider 1533. The actuator interlock 1140 is sized such that, in the first position shown in FIG. 23, a second end 2341 of the actuator interlock 1140 abuts a leading end 2331 of the secondary actuator 1153 and a first end 2342 of the actuator interlock 1140 abuts a trailing edge 2354 of the secondary electrode slider 1533 such that the actuator interlock 1140 controls relative movement of the primary release 1130 (and thus the primary actuator 1132) toward the secondary grip 1153 (and thus the secondary actuator 1152) toward one another. In various embodiments, a pin (not shown) fixed to the primary electrode slider 1533 slides within a slot (not shown) within the actuator interlock 1140, and ends of the slot in the actuator interlock 1140 present hard stops that limit the travel of the pin and, corresponding, limit the travel of the secondary electrode slider 2151. Thus, the secondary actuator 1140 operates to maintain a distance between the primary release 1130 and the secondary grip 1153 while the actuator interlock 1140 is in the first position shown in FIG. 23.

The actuator interlock 1140 also features a lock bar (not shown in FIG. 23) that engages the primary release 1130, as further described with reference to FIGS. 29-31. The lock bar prevents the primary release from being engaged while the actuator interlock 1140 is in the first position, as further described below. The actuator interlock 1140 also features locking teeth 2343 configured to engage locking notches (not shown in FIG. 23) within the housing 1110 when the actuator interlock 1140 is in a second position, as further described below with reference to FIG. 24. The locking teeth 2343 operate to secure the actuator interlock 1140 in place to enable the primary actuator (not shown in FIG. 23) and the primary release 1130 to be moved independently of the secondary actuator (not shown in FIG. 23) and the secondary grip 1153 to enable the primary electrode (not shown in FIG. 23) to be partially retracted while the secondary electrode (not shown in FIG. 23) stays in place, as further described below. Finally, a lever 2344 allows an operator to engage the actuator interlock 1140 to rotate the actuator interlock 1140 between the first position and the second position, as further described below.

Referring to FIG. 24, in a first position of the actuator interlock 1140, locking teeth 2343 are situated to potentially engage locking notches 2446 in the housing 1110 to lock the secondary electrode (not shown in FIG. 24) in place. The locking notches 2446 are positioned to receive the locking teeth 2343 after the secondary actuator and the secondary grip (not shown in FIG. 24) are moved to extend the distal end of the secondary electrode (not shown in FIG. 24) as previously described. As will be appreciated and as will be further described below, when the actuator interlock 1140 is rotated from the first position shown in FIG. 24 to a second position (shown in FIGS. 26-28), the locking teeth 2343 fit within the locking notches 2446 to prevent the actuator interlock 1140 from being moved relative to the housing 1110 when, for example, the primary release 1130 is engaged and moved relative to the housing. As further described below, the use of the locking teeth 2343 to secure the position of the actuator interlock 1140 serves to lock a secondary electrode slider to prevent movement of the secondary electrode (neither of which is shown in FIG. 24), as is further described below.

Referring to FIG. 25, the actuator interlock 1140 is disposed within the housing 1110 with the actuator interlock 1140 shown in a first position. The actuator interlock 1140 rotates within the housing 1110 around a primary electrode 207 and a secondary electrode 211. A lever 2344 extending out of the housing 1110 through the channel 2349 allows a user to engage and rotate the actuator interlock 1140. As previously shown in FIGS. 18-20, the interlock lever 2344 is situated forward of a secondary actuator 1152 and a secondary grip 1153, where a forward direction is the left side of the FIGURE.

Referring to FIG. 26, the actuator interlock 1140 is shown in a second position after the secondary electrode (not shown in FIG. 26) has been deployed and before the primary electrode (not shown in FIG. 26) is partially retracted. The lever 2344 is used to rotate the actuator interlock 1140 relative to the housing 1110 so as to cause locking teeth 2343 of the actuator interlock 1140 to move into a second position within the channel 2349 where the locking teeth 2343 engage locking notches (not shown in FIG. 26) to fix the actuator interlock 1140 in place. As previously described with reference to FIG. 23, the actuator interlock 1140 maintains a distance between the primary release (not shown in FIG. 26) and the secondary grip 1153 while the actuator interlock 1140 is in the first position. However, when the actuator interlock 1140 is in the second position as shown in FIG. 26, the actuator interlock 1140 no longer prevents relative motion of the primary release 1130 (and thus the primary actuator 1132) toward the secondary grip 1153 (and thus the secondary actuator 1152). With the actuator interlock 1140 in the second position, the position of the secondary electrode slider 2151 is secured relative to the housing 1110 and, thus, may not move longitudinally relative to the housing 1110; however, the primary actuator 1132 may be moved upon engaging the primary release 1130. Thus the primary actuator (also not shown in FIG. 26) is enabled to move independently of the secondary actuator (also not shown in FIG. 26) to allow the primary actuator to be moved toward the secondary grip 1153 to retract the primary electrode (not shown in FIG. 26) without moving the secondary electrode (not shown in FIG. 26).

Referring to FIG. 27, another view is provided of the actuator interlock 1140 in the second position to show how the locking teeth 2343 engages locking notches 2446 in the housing 1110 to lock the secondary electrode (not shown in FIG. 26) in place. The locking notches 2446 receive the locking teeth 2343 to lock the actuator interlock 1140 and to fix a position of the secondary electrode slider 2151 in place while the primary actuator 1132 and the primary electrode slider 1533 are able to move upon the primary release 1130 being engaged. Again, the lever 2344 allows a user to move the actuator interlock 1140 from the first position (shown in FIGS. 23-25) to the second position shown in FIGS. 26-28). It will be appreciated that the lever 2344, which is slidable across the channel 2349 to enable the actuator interlock 1140 to be moved into the second position, is in the nature of a swipe lock that can be swiped from the first position to the second position.

Referring to FIG. 28, in the user interface 1101 the actuator interlock 1140 has been rotated within the housing 1110 about the primary electrode 207 and the secondary electrode 211 into the second position. FIG. 28 is similar to FIG. 25 except, in FIG. 28, the actuator interlock 1140 has been rotated into the second position, whereas FIG. 25 showed the actuator interlock 1140 in the first position. The lever 2344 (extending from the actuator interlock 1140 and out of the housing 1110 through a channel 2349) has been engaged by a user to rotate the actuator interlock 1140 into the second position, as previously described with reference to FIGS. 26 and 27.

Referring to FIG. 29, another view of the actuator interlock 1140 is provided to show operation of a lock bar 2945 associated with the actuator interlock 1140. The lock bar 2945 selectively prevents movement of a primary release 1130. As previously described with reference to FIG. 5, once the primary electrode 207 is deployed with the distal end 209 at a desired location relative to the reference point 201, the primary electrode 207 remains stationary while the secondary electrode 211 is extended. The lock bar 2945 prevents the primary release 1130 from being engaged to prevent the primary actuator (not shown in FIG. 29) from being moved to prevent movement of the primary electrode while the secondary electrode (neither of which is shown in FIG. 29) is extended.

Still referring to FIG. 29, the actuator interlock 1140 is shown in the first position and is positioned before the secondary release and secondary actuator are engaged to move secondary electrode (none of which are shown in FIG. 29) independently of the primary actuator and the primary electrode (also not shown in FIG. 29) as shown in FIG. 5. In this position, a distal end 2957 of the lock bar 2945 does not engage the primary release 1130. As previously described with reference to FIGS. 12-17, the primary release 1130 and thus the primary actuator 1132 may be operated to move the primary electrode (not shown in FIG. 29) as desired. As also previously described, for example, and with reference to FIGS. 14 and 22, until the secondary release is engaged the secondary actuator and, thus, the secondary electrode move in concert with the primary actuator and the primary electrode, as previously described.

Referring to FIG. 30, with the actuator interlock 1140 in the first position, the secondary actuator (not shown in FIG. 30) and, thus, the secondary grip 1153 has been moved forward to extend the secondary electrode (not shown in FIG. 30). As a result, the actuator interlock 1140 moves forward and, thus, the lock bar 2945 extends through a lock channel 3060 in the primary release 1130. The lock channel 3060 includes a locking lobe 3062 and an open lobe 3064. When the actuator interlock 1140 is in the first position, the lock bar 2945 passes through the locking lobe 3062 of the lock channel 3060. As a result, if a user attempts to engage the primary release 1130 by depressing it as described with reference to FIG. 13, the lock bar 2945 engages a first inner surface 3063 within the locking lobe 3062, thereby preventing the primary release 1130 from being depressed. However, as further described with reference to FIG. 31, when the actuator interlock 1140 is rotated into the second position, the lock bar 2945 rotates with the actuator interlock 1140 and the lock bar 2945 moves into the open lobe 3064 where the lock bar 2945 no longer engages the first inner surface 3063 when a user attempts to depress the primary release 1130.

Referring to FIG. 31, the actuator interlock 1140 has been rotated within the housing 1110 about the primary electrode 207 and the secondary electrode 211 into the second position. With the actuator interlock 1140 rotated into the second position, the lock bar 2945 has rotated into the open lobe 3064. With the lock bar 2945 extending through the open lobe 3064, a user can depress the primary release 1130 without surfaces of the lock channel 3060 engaging the lock bar 2945. Thus, once the actuator interlock 1140 is moved into the second position, the primary release 1130 may be engaged to enable partial retraction of the primary electrode 207, as further described below.

Figure 32A:
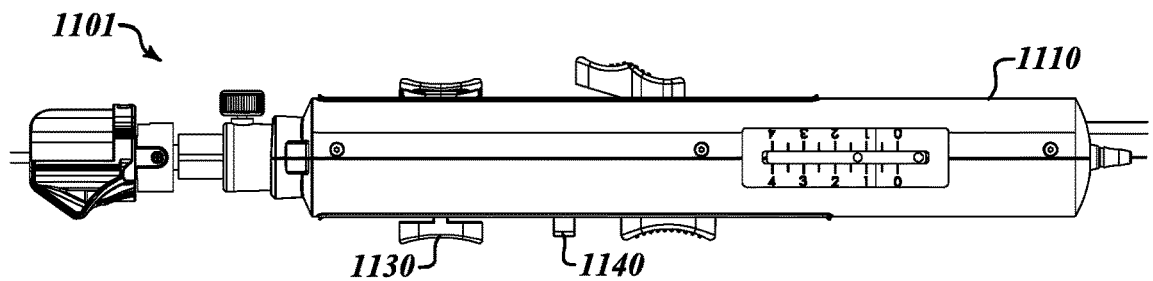
Figure 32B:
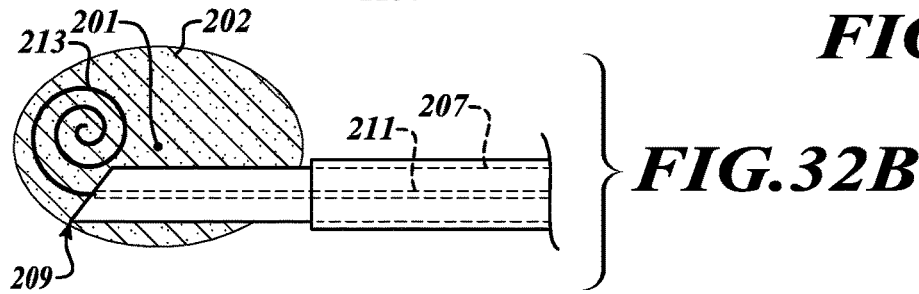

Referring to FIGS. 32A and 32B, the secondary electrode 211 has been deployed and locked in position. The distal end 213 of the secondary electrode 211 extends beyond the reference point 201, and the actuator interlock 1140 has been moved into the second position within the housing 1110 before the primary release 1130 is engaged to initiate retraction of the primary electrode 207 to withdraw the distal end 209 of the primary electrode 207 away from reference point 201. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment. As described with reference to FIGS. 29-31, once the actuator interlock 1140 is in the second position, the lock bar (not shown in FIG. 32A) does not prevent the depressing of the primary release 1130. Thus, the user interface is configured for partial withdrawal of the primary electrode 207.

Figure 33A:
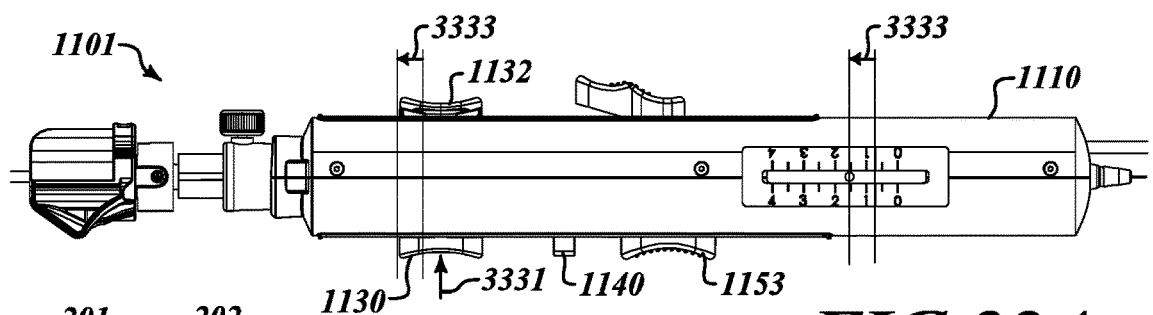
Figure 33B:
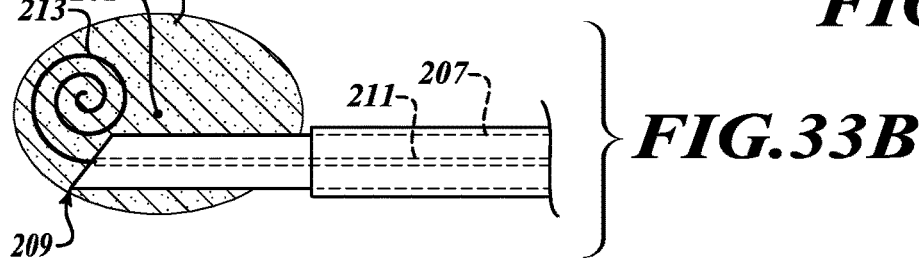

Referring to FIGS. 33A and 33, the primary release 1130 has been depressed in a direction 3331 toward the housing 1110 to release the primary actuator 1132. The primary actuator 1132 and the primary release 1130 may now be moved rearward to partially retract the distal end 209 of the primary electrode 207 away from the reference point 201. Depressing the primary release 1130 allows the primary actuator to move relative to the housing 1110 as previously described with reference to FIGS. 12A-17. As previously described with reference to FIG. 22, the previous activation of the secondary release 1150 caused the locking arm 2259 to disengage from the locking notch 2239 in the primary electrode slider 1533 so that movement of the secondary actuator 1152 and the secondary electrode slider 2151 is no longer coupled with the primary electrode slider 1533. Referring again to FIG. 33A, the actuator interlock 1140 has been rotated into the second position so as not to block relative movement between the primary release 1130 and the secondary grip 1153. Accordingly, the primary actuator 1132 and, thus, the primary electrode 207 may now be moved independently of the secondary electrode 211.

Figure 34A:
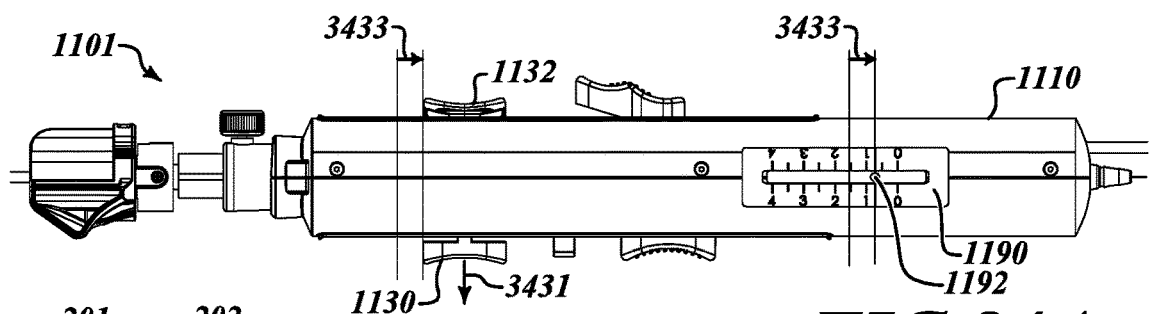
Figure 34B:
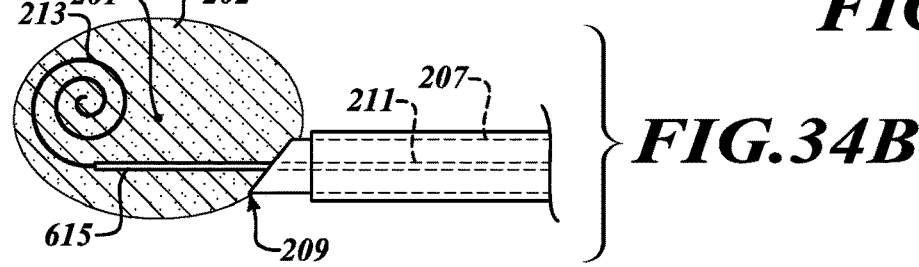

Referring to FIGS. 34A and 34B, the primary actuator 1132 has been moved a distance 3433 to retract the distal end 209 of the primary electrode 207 by that same distance 3433. The primary release 1130 is then released to travel in a direction 3431 where the primary actuator 1132 and the primary release 1130 are then locked in place relative to the housing 1110, as previously described with reference to FIGS. 14A-17. With the movement of the primary electrode 207, the indicator 1192 on the depth gauge 1190 also moves the distance 3433 to reflect the retraction of the distal end 209 of the primary electrode 207. Accordingly, in these embodiments the user interface has allowed the distal end 209 of the primary electrode 207 and the distal end 213 of the secondary electrode 211 to be positioned at desired locations proximate to the reference point 201 in preparation for application of electrical current to treat tissue at or near the reference point 201.

Referring to FIG. 35, another embodiment of a user interface 3501 may be used to position a primary electrode and a secondary electrode relative to a reference point (not shown in FIG. 35). As in previously-described embodiments, in these embodiments the user interface 3501 includes components that are moved parallel with or transverse to an axis 3521 or rotated along a curve 3523 around the axis 3521, as further described below. In such embodiments, the user interface 3501 includes a coupling 3520 configured to engage an electrosurgical apparatus, such as a bronchoscope (not shown in FIG. 35). By way of contrast to previous embodiments of the user interface, these embodiments of the user interface 3501 do not include a sheath actuator. However, a sheath actuator, like the sheath actuator described in connection with previous embodiments and as described with reference to FIGS. 7-11, may be added to these embodiments of the user interface 3501. Alternatively, the sheath actuator may be integrated with the electrosurgical apparatus as previously described with reference to FIG. 7. Also, although not shown in FIG. 35, like the previous embodiments of the user interface 1101 of FIGS. 11-24, leads from a switchable current source are received at the user interface 3501 and a sheath containing primary and secondary electrodes (not shown in FIG. 35) extend from the coupling 3520.

The user interface 3501 includes several user controls whose operation and effect are described in further detail in the following figures. A primary release 3530 coupled to the housing 3510 at a first end 3541 of the housing 3510 is configured unlock movement of the primary electrode (not shown in FIG. 35). The primary release 3530 includes a release lever 3532 and a release spring 3533 to bias the release lever 3532 in a locked position. The primary release 3530 engages a slidable shaft 3536 that is slidably received within a forward opening 3538 in the primary release 3530. The slidable shaft 3536 is fixably coupled to the coupling 3520. The slidable shaft 3536 is configured to move back and forth along the axis 3521. The slidable shaft 3536 is fixably coupled to a depth setter rod 3534 in the nature of a geared rack. As explained further below, the depth setter rod 3534 is engaged by the actuator interlock 3540 to selectively secure a position of the slidable shaft 3536 and, as a result, the position of the primary electrode.

The slidable shaft 3536 includes depth indicia 3539 that may be read at the forward opening 3538 to determine a position of the primary electrode (not shown). It will be appreciated that the depth indicia 3539 are read at the forward opening 3538 in a similar fashion, with reference to FIG. 11, to reading of the indicator 1192 on the depth gauge 1190 to determine a position of the primary electrode (not shown in FIG. 35). As will be further described below, the primary electrode is fixably coupled to the housing 3510 such that sliding the housing 3510 relative to the slidable shaft 3536 controls a position of the primary electrode. In other words, in contrast with previous embodiments of the user interface of FIG. 11 (which included a separate primary actuator 1132), the housing of the user interface 3501 itself acts as a primary actuator for the primary electrode. The housing 3510 is moved forward and back along the axis 3521 to extend and retract, respectively, the primary electrode, as further described below.

A secondary actuator 3552 is fixably coupled to a secondary electrode slider (not shown in FIG. 35), as will be described with reference to FIG. 36. Sliding the secondary actuator 3552 within the secondary channel 3554 channel permits movement of the secondary electrode (not shown in FIG. 35). The secondary actuator 3552 is selectively locked and unlocked relative to the housing 3510 (and, thus, relative to the primary electrode whose movement is controlled by movement of the housing 3510) by an interlock lever 3540 that is secured to the secondary electrode slider 3551. The interlock lever 3540 moves within a guide slot 3542 along the axis 3521 and along a curve 3523 around the axis 3521. A position of the interlock lever 3540 relative to the guide slot 3542 controls the locking and unlocking of the secondary actuator 3550 and, thus, of the secondary electrode, as further described below. In the initial configuration shown in FIG. 35, a lever end 3547 is situated at a first position 3571 within the guide slot 3542, which secures the secondary actuator 3552 at a second end 3555 of the secondary channel 3554. In an illustrative embodiment, guide indicia 3543 may be included on the housing 3510 near the guide slot 3542 to direct a user in moving the interlock lever 3540 to control operation of the secondary actuator 3550. As also described further below, in other configurations the depth setter rod 3534 may be engaged by the interlock lever 3540 to selectively lock the position of the primary electrode (not shown in FIG. 35).

Referring to FIG. 36, an exploded view of the user interface 3501 of FIG. 35 further details the composition and operation of the user interface 3501. As already described with reference to FIG. 35, the user interface 3501 includes a coupling 3520 fixably coupled to an end of the slidable shaft 3536. The slidable shaft 3536, which is fixably coupled with the depth setter rod 3534, is slidably received within the forward opening 3538 of the primary release 3530. The release lever 3532 selectively releases the slidable shaft 3536 to move relative to the forward opening 3538 and is biased in a locked position by a spring 3637 coupled between the primary release 3530 and the release lever 3532. The primary release 3530 is fixably coupled to the housing 3510. Beyond the primary release 3530, the slidable shaft 3536 is slidably received within an opening 3655 in a secondary electrode slider 3551.

The secondary electrode slider 3551 is fixably coupled to the secondary actuator 3552, which slidably moves within the secondary actuator channel 3554. Similarly, on an underside of the housing 3510, a secondary grip 3653 is coupled to an underside of the secondary electrode slider 3551 and extends through an additional channel 3655 in the housing 3510. As previously described with reference to previous embodiments of the user interface, providing both the secondary actuator 3552 and the secondary grip 3653 may allow a user to apply force as needed to cause the secondary electrode (not shown in FIG. 36) to pierce tissue as desired for a particular application. When the secondary electrode slider 3551 is slidably received within the housing 3510, electrodes (not shown in FIG. 36) may extend through a forward opening 3641 in the housing 3510.

In the exploded diagram of FIG. 36, additional aspects of the depth setter rod 3534 and the interlock lever 3540 are shown to further describe the configuration of the user interface 3501. The interlock lever 3640 is secured to the secondary electrode slider 3551. The interlock lever 3540 is configured to engage the depth setter rod 3534. Specifically, in an illustrative embodiment, the depth setter rod 3534 includes a lower-geared surface 3633 and an upper-geared surface 3635. Correspondingly, the interlock lever 3540 includes a lower-geared lock 3643 and an upper-geared lock 3645. When a user manipulates the lever end 3547, the interlock lever 3540 may be rotated to cause the lower-geared lock 3643 to engage the lower-geared surface 3633 of the depth setter rod 3534 and to cause the upper-geared lock 3645 to engage the upper-geared surface 3635 of the depth setter rod 3534. In an illustrative embodiment, the lower-geared lock 3643 and the upper-geared lock 3645 are flexible members configured to rotate over and engage the lower-geared surface 3633 and the upper-geared surface 3635, as further described below. The lower-geared lock 3643 and the upper-geared lock 3645 flex when rotated over the lower-geared surface 3633 and the upper-geared surface 3635 of the depth setter rod 3534, which applies pressure to the lower-geared surface 3633 and the upper-geared surface 3635 of the depth setter rod 3534. The pressure thus applied secures the interlock lever 3540 from being moved relative to the depth setter rod 3534 until the interlock lever 3540 is rotated to disengage the lower-geared lock 3643 and the upper-geared lock 3645 from the lower-geared surface 3633 and the upper-geared surface 3635 of the depth setter rod 3534. When the lower-geared lock 3643 and the upper-geared lock 3645 of the interlock lever 3540 engage the lower-geared surface 3633 and the upper-geared surface 3635, respectively, of the depth setter rod 3534, the slidable sleeve 3536 is secured relative to the depth setter rod 3534 and thus moves in concert with the interlock lever 3540. Accordingly, motion of the slidable sleeve 3536 is then limited to movement permitted by guide slot 3542 which engages the interlock lever 3540, as described further below.

Referring to FIGS. 37A and 37B, the user interface 3501 is shown in a first configuration prior to extension of the primary electrode 207 beyond the distal end 105 of the sheath 103 proximate to the reference point 201, as shown in the inset view. As previously described, the user interface 3501 does not include a sheath actuator to position the sheath 103, although the same may be added to the user interface, for example, at the coupling 3520, or may be included within the electrosurgical apparatus (not shown in FIG. 37A).

In various configurations of the user interface 3501, the slidable shaft 3536 is fully extended from the primary release 3530, corresponding with the distal end 209 of the primary electrode 207 resting within the distal end 105 of the sheath 103. The secondary actuator 3552 is positioned at a rear end 3555 of the secondary channel 3554 in the housing 3510, corresponding with a distal end 213 of a secondary electrode 211 resting within the distal end 209 of the primary electrode 207, prior to deployment of the secondary electrode 211 as previously described with reference to the previous embodiments of the user interface 3501. The interlock lever 3540 also is in an initial position with a lever end 3547 being positioned at a first end 3571 of the guide slot 3542 to secure the secondary actuator 3552 in place at the second end 3555 of the secondary channel 3554.

Deployment of the primary electrode 207 and the secondary electrode 211 begins with a user engaging the primary release 3530. In an illustrative embodiment, the primary release 3530 is engaged by depressing a distal end 3729 of the release lever 3532 to deform the release spring 3637 and to permit movement of the slidable shaft 3536. To extend the primary electrode 207, with the primary release 3530 thus engaged, the housing 3510 is moved in a direction 3708 along the slideable shaft 3536. Whether the desired location has been reached may be determined by reading the depth indicia 3539 on the slideable shaft 3536 at the forward opening 3538 in the primary release 3530. Once the housing 3510 has moved along the slidable shaft 3536 to move the primary electrode 3507 to a desired location, the distal end 3535 of the release lever 3532 is released, thereby allowing the release spring 3637 to return to an undeformed state and locking the slidable shaft 3536 in place relative to the primary release 3530. The primary release 3530 is configured to apply mechanical pressure to slideable shaft 3536 such that, before the distal end 3729 of the release lever 3532 is depressed to engage the primary release 3530, the primary release 3530 and the rest of the user interface 3501 cannot be moved relative to the slidable shaft 3536. Correspondingly, once the distal end distal end 3729 of the release lever 3532 is released to disengage the primary release 3530, the primary release 3530 and the rest of the user interface 3501 cannot be moved relative to the slidable shaft 3536, securing the position of the primary electrode 207, as further described herein.

Referring to FIGS. 38A and 38B, the distal end 209 of the primary electrode 207 has been extended to a desired location proximate to the reference point 201 in a manner as described with reference to FIGS. 37A and 37B. The movement of the housing 3510 relative to the slidable shaft 3536 shown in FIG. 38A has caused the distal end 209 of the primary electrode 207 to move to a desired location proximate to the reference point 201. That the desired location has been reached may be verified by reading the depth indicia 3639 on the slideable shaft 3536 at the forward opening 3538 in the primary release 3530. Also, because the interlock lever 3540 has secured the secondary actuator 3552 at the second end 3555 of the secondary channel 3554, movement of the housing 3510 also causes the secondary actuator 3552 to move the secondary electrode 211 in concert with the movement of the primary electrode 207, with the distal end 213 of the secondary electrode 211 remaining positioned inside the distal end 209 of the primary electrode 207.

Referring to FIG. 39, the interlock level 3540 engages the depth setter rod 3534 to lock a position of the secondary actuator (not shown in FIG. 39). As previously described, the primary release 3530 controls the passage of the slideable shaft (not shown in FIG. 39) through the forward opening 3538 to control positioning of the primary electrode (also not shown in FIG. 39). In addition to the forward opening 3538, a rod opening 3928 separately and slidably receives the depth setter rod 3534 as the slidable shaft is moved through the primary release 3530.

The depth setter rod 3534, as previously described, includes the lower-geared surface 3633 and the upper-geared surface 3635 that are selectively engaged by the lower-geared lock 3643 and the upper-geared lock 3645, respectively, of the interlock lever 3540. The lever end 3547 allows a user to rotate the interlock lever 3540 to cause the geared locks 3643 and 3645 to engage the geared surfaces 3633 and 3635, respectively.

Referring to FIG. 40, the interlock lever 3740 may be positioned so that the lower-geared lock and the upper-geared lock (both of which are behind the slidable shaft 3536 and, thus, are not shown in FIG. 40) slide through the rod opening 3928 without the lower-geared lock and the upper-geared lock (both not shown in FIG. 40) engaging the lower-geared surface 3633 and the upper-geared surface 3635 of the depth setter rod 3534. In this configuration, movement of the primary electrode and the secondary electrode (both not shown in FIG. 40) are controlled by release of the primary release and the housing both (not shown in FIG. 40) as previously described with reference to FIGS. 37 and 38. The position of the lever end 3547 corresponds generally with that of the lever end being at a first, second, or third position within the guide slot (not shown in FIG. 40) further described below in which the lower-geared lock and the upper-geared lock do not secure the secondary electrode slider (also not shown in FIG. 40) to the depth setter rod 3534. A user may engage the lever end 4047 to rotate the interlock lever 3540 in a direction that will lead the lower- and upper-geared locks toward the lower-geared surface 3633 and the upper-geared surface 3635, respectively, of the depth setter rod 3534, as further described below.

Referring to FIG. 41, the interlock lever 3540 has been rotated by user manipulation of the lever end 3547 so that the lower-geared lock 3643 and the upper-geared lock 3645 of the interlock lever 3540 begin to engage the lower-geared surface 3633 and the upper-geared surface 3635 of the depth setter rod 3534 forward of the rod opening 3928. As previously described, in an illustrative embodiment, the lower-geared lock 3643 and the upper-geared lock 3645 of the interlock lever 3540 are flexible so that they may deform slightly in order to engage the depth setter rod 3534. Thus, the position of the lever end 3547 corresponds generally with that of the lever end 3547 being moved between a third position within the guide slot toward a fourth position within the guide slot (not shown in FIG. 40) further described below in which the lower-geared lock and the upper-geared lock do not yet secure the secondary electrode slider (also not shown in FIG. 40) to the depth setter rod 3534, as further described below.

Referring to FIG. 42, the interlock lever 43540 has been further rotated by user manipulation of the lever end 3547 into a locked position in which the lower-geared lock 3643 and the upper-geared lock 3645 of the interlock lever 3540 engage the lower-geared surface 3633 and the upper-geared surface 3635, respectively, of the depth setter rod 3534 forward of the rod opening 3928. In a locked position, corresponding with the lever end 3547 being within a fourth or fifth position within the guide slot (not shown in FIG. 42) further described below in which the lower-geared lock 3643 and the upper-geared lock 3645 secure the interlock lever 3540 to the depth setter rod 3534. In this position, even if the housing and thus the primary electrode (neither of which are shown in FIG. 42) are moved, the secondary actuator 3540 maintains the position of the secondary actuator (not shown in FIG. 42). The function of the interlock lever 3540 in positioning the primary and secondary electrodes is further described below.

In FIGS. 43A-47C, side and top views of the second embodiment of the user interface are shown, along with inset views to show positions of the electrodes corresponding to the configuration of the user interface. In FIGS. 43A-47C, it should be appreciated that the lever end 3547 of the interlock lever 3540 provides a visible and tactile indicator of a phase in which the user interface 3501 operates, for example, such as in extending the secondary electrode 211 or retracting the primary electrode 207.

Referring to FIGS. 43A-43C, the user interface 3501 is shown with the primary electrode 207 extended before any steps have been taken to extend the secondary electrode 211. The primary release 3530 is in a locked position to secure the housing 3510 relative to the slideable shaft 3536. As a result, the distal end 209 of the primary electrode 207 is fixed in position proximate to the reference point 201. The interlock lever 3540 is in an initial locked position as indicated by the lever end 3547 of the interlock lever 3540 being disposed in the first position 3571 of the guide slot 3542. In this position, the lower-geared lock and the upper-geared lock (not shown in FIGS. 43A and 43B) of the interlock lever 3540 do not engage the depth setter rod 3534. However, with the lever end 3547 at the first position 3571, the interlock lever 3540 is restrained from moving along the axis 3521 (FIG. 35) and thus holds prevents the secondary actuator 3552 and the secondary electrode slider 3551 in place within the secondary channel 3554. Thus, because the primary electrode 207 is fixed in position and because the secondary electrode slider 3551 is locked in position, the distal end 213 of the secondary electrode 211 is also locked in position relative to the reference point 201.

Referring to FIGS. 44A-44C, the user interface 3501 is shown with the primary electrode 207 extended and the actuator interlock 3540 manipulated to unlock movement of the secondary electrode 211. The primary release 3530 remains in a locked position to secure the housing 2510 relative to the slideable shaft 3536. As a result, the distal end 209 of the primary electrode 207 remains fixed in position proximate to the reference point 302. The interlock lever 3540 is moved to a second position as indicated by the lever end 3547 of the interlock lever 3740 having been moved to the second position 4473 of the guide slot 3542. In this position, as in the position described with reference to FIGS. 44A-44C, the lower-geared lock and the upper-geared lock (not shown in FIGS. 44A and 44B) of the interlock lever 3540 still do not engage the depth setter rod 3534. However, with the lever end 3547 at the second position 4473, the interlock lever 3540 is no longer restrained from moving along the axis 3521 (FIG. 35) within the secondary channel 3554. The lever end 3547 thus may engage in limited movement within the guide slot 3542. Thus, the secondary actuator 3552 and the secondary slider 3551 also may engage in limited movement within the secondary channel 3554 to move the secondary electrode 211 toward the reference point 201. With the primary electrode 207 thus fixed in position, the distal end 213 of the secondary electrode 211 may be moved toward the reference point 201 independently of the primary electrode 207.

Referring to FIGS. 45A-45C, the primary release 3530 remains in a locked position and the secondary electrode 211 has been extended. As a result, the distal end 209 of the primary electrode 207 remains fixed in position proximate to the reference point 201. The interlock lever 3540 is moved to a third position as indicated by the lever end 3547 of the interlock lever 3540 being disposed in the third position 4575 of the guide slot 3542. In this position, as in the position described with reference to FIGS. 44A-44C, the lower-geared lock and the upper-geared lock (not shown in FIGS. 45A and 45B) of the interlock lever 3540 still do not engage the depth setter rod 3534. The lever end 3547 moves to the third position 4575 within the guide slot 3542 as a user moves the secondary actuator 3552 to move the secondary electrode slider 3551 within the secondary channel 3554. The movement of the secondary actuator 3552 moves the distal end 213 of the secondary electrode 211 to a desired position beyond the reference point 201 while the distal end 209 of the primary electrode 207 remains fixed in position. Insulation 515 on the secondary electrode 211 electrically isolates the distal end 213 of the secondary electrode 211 from the distal end 209 of the primary electrode 207, as previously described.

Referring to FIGS. 46A-46C, the primary release 3530 remains in a locked position to secure the housing 3510 relative to the slideable shaft 3536 and the actuator interlock 3540 has been manipulated to lock the movement of the secondary electrode 211. As a result, the distal end 209 of the primary electrode 207 remains fixed in position proximate to the reference point 201. The interlock lever 3540 is moved to a fourth position 4677 by a user having moved the lever end 3547 of the interlock lever 3540 to the fourth position 4677 of the guide slot 3542. In this position, as described with reference to FIG. 42, the lower-geared lock 3643 and the upper-geared lock 3645 of the interlock lever 3540 engage the lower-geared surface 3633 and the upper-geared surface 3635, respectively, of the depth setter rod 3534. Thus, with the lever end 3547 in the fourth position 4677 of the guide slot 3542, the interlock lever 3540 and, thus, the secondary electrode slider 3551 and the secondary actuator 3552 are locked in position with respect to the depth setter rod 3534. Accordingly, both the distal end 209 of the primary electrode 207 and distal end 213 of the secondary electrode 211 are locked in place relative to the reference point 201.

Referring to FIGS. 47A-47C, the primary release 3530 has been engaged to unlock the position of the housing 3510 relative to the slideable shaft 3536 and the housing 3510 has been moved in a direction 4781 to partially retract the distal end 309 of the primary electrode 207. As a result, the distal end 209 of the primary electrode 207 is partially withdrawn from the reference point 201 toward the distal end 105 of the sheath 103. The interlock lever 3540 is moved to a fifth position by the movement of the housing 3510, with the lever end 3547 of the interlock lever 3540 to the fifth position 4779 of the guide slot 3542. In this position, as described with reference to FIG. 42, the lower-geared lock 3643 and the upper-geared lock 3645 of the interlock lever 3540 continue to engage the lower-geared surface 3633 and the upper-geared surface 3635, respectively, of the depth setter rod 3534. Thus, with the lever end 3547 in the fourth position 4779 of the guide slot 3542, the interlock lever 3540 and, thus, the secondary electrode slider 3551 and the secondary actuator 3552 remain locked in position with respect to the depth setter rod 3534. The movement of the housing 3510 causes the secondary electrode slider 3551 and the secondary actuator 3552 to move to forward in the secondary channel 3554 to allow the secondary electrode slider 3551 to remain locked in position relative to the depth setter rod 3534 while the housing 3510 is moved in the direction 4781. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment. Accordingly, these embodiments of the user interface have allowed the distal end 209 of the primary electrode 207 and the distal end 213 of the secondary electrode 211 to be positioned at desired locations proximate to the reference point 201 in preparation for application of electrical current to treat tissue at or near the reference point 201.

Referring to FIG. 48, another embodiment of the user interface 4801 is shown for positioning electrodes. The user interface 4801 includes components that are moved parallel along an axis 4821 or rotated along a curve 4823 around the axis 4821, as further described below. As also further described below, the user interface 4801 generally is controlled by sliding the outer housing 4810 along the axis 4821, by sliding actuators extending through the outer housing 4810 at a first end 4841 of the outer housing 4810, and by rotating the outer housing around the axis 4821.

The user interface 4801 includes a coupling 4820 to engage a port on an electrosurgical apparatus, such as a bronchoscope, as described with reference to FIGS. 1, 7, and 8. The user interface 4801 also includes a sheath actuator 4804 to position a sheath (not shown in FIG. 48) as previously described with reference to FIGS. 7-11. The sheath actuator 4804 includes a slidable sleeve 4812 and a sheath lock 4806 to engage the slidable sleeve 4812 and secure the slidable sleeve 4812 in place, as described further below. It will be appreciated that, as described with reference to FIG. 35 and regarding another embodiment of the user interface 3501, a sheath actuator may be part of the bronchoscope or a separate device inserted between the user interface 4801 and the bronchoscope (not shown in FIG. 48).

The user interface 4801 includes an outer housing 4810 configured to enable manipulation of the electrodes. The outer sheath 4810 includes a first guide slot 4831 configured to receive and direct movements of a primary actuator 4832 that extends up through the first guide slot 4831. The outer housing 4810 also includes a second guide slot 4851 configured to receive a secondary actuator (not shown in FIG. 48). As is further described below, rotation of the outer housing 4810 along the curve 4823 about the axis 4821 exposes and introduces the secondary actuator into the second guide slot 4851. When the secondary actuator is received through the second guide slot 4851, the secondary actuator may be secured in place with a slidable actuator lock 4859, the operation of which is further described below. Also, although not shown in FIG. 48, as in embodiments shown in FIGS. 1 and 11, leads from a switchable current source are received at the user interface 4801 and a sheath containing primary and secondary electrodes extends from the user interface 4801 via the coupling 4820.

Referring to FIG. 49, the outer housing 4810 includes the first guide slot 4831 to engage the primary actuator 4832. The primary actuator 4832 extends from a primary electrode slider 4914, as described further below. The primary actuator 4832 extends upwardly through the first guide slot 4831 in the outer housing 4810. By sliding the primary actuator 4832 through the first guide slot 4831, a user may extend, lock, and partially retract the primary electrode (not shown in FIG. 49). The outer housing 4810 also includes the second guide slot 4851 that is configured to receive the secondary actuator 4952 and which extends from the secondary electrode slider 4916 through an intermediate guide slot 4933 in the primary electrode slider 4914, as further described below. A ramp 4957 adjacent a second end 4958 of the second guide slot 4851 and on an underside of the outer housing 4810 engages and subverts the secondary actuator 4852 when it is desired to retract the secondary electrode, as will be described further below.

The second guide slot 4851 in the outer housing 4810 is configured to receive the secondary actuator 4952 when, as further described below, rotation of the outer housing 4810 along the curve 4823 about the axis 4821 (FIG. 48) exposes and introduces the secondary actuator 4952 into the second guide slot 4851. When the secondary actuator is received through the second guide slot 4851, the secondary actuator may be secured in place with a slidable actuator lock 4859, the operation of which is further described below.

The primary electrode slider 4914 is longitudinally fixable to the primary electrode (not shown in FIG. 49) such that longitudinal movement of the primary electrode slider 4914 extends and retracts the primary electrode without twisting the primary electrode. The primary electrode slider 4914 is slidably and rotatably received within the outer housing 4810. The primary actuator 4832 extends outwardly from the primary electrode slider 4914 so that it extends upwardly through the outer housing 4810. The primary electrode slider 4914 also includes an intermediate guide slot 4933 configured to receive the secondary actuator 4952 extending from the secondary electrode slider 4916.

The secondary electrode slider 4916 is longitudinally fixable to the secondary electrode (not shown in FIG. 49) such that longitudinal movement of the secondary electrode slider 4916 extends and retracts the secondary electrode without twisting the secondary electrode. The secondary electrode slider 4916 is slidably received within the primary electrode slider 4914. The secondary actuator 4952 extends outwardly from the secondary electrode slider 4916 is receivable through the intermediate guide slot 4933 in the primary electrode slider 4914. In an illustrative embodiment, the secondary actuator 4952 is spring-loaded or similarly extendable such that, when the outer housing 4810 is rotated such that the second guide slot 4851 overlaps the intermediate guide slot 4933 in the primary electrode slider 4914, the secondary actuator 4952 extends upward through the second guide slot 4851. In another illustrative embodiment, when the outer housing 4810 is rotated to move the second guide slot 4851 so that it no longer overlaps the intermediate guide slot 4933 in the primary electrode slider 4914, the ramp 4959 engages and compresses the secondary actuator 4952 to fit beneath the outer housing 4810.

The sheath actuator 4804 includes a slidable sleeve 4812 fixably coupled to the sheath (not shown) and slidably received within the coupling 4820 and securable with the sheath lock 4806. Operation of the sheath actuator 4804 is further described with reference to FIGS. 50 and 51. In an illustrative embodiment, the slidable sleeve 4812 may be fixably coupled to the outer housing 4810, such that movement of the electrodes (not shown in FIG. 49) made by using the user interface 4810 moves the electrodes relative to the sheath.

Referring to FIGS. 50A and 50B and as used in conjunction with a user interface 4801, the sheath actuator 4804 controls a position of the sheath 103. Specifically, a position of the sheath 103 is controlled by sliding the slidable sleeve 4812 within the coupling 4820 and securing the sheath 103 at the desired location by securing the slidable sleeve 4812 with the sheath lock 4806. The sheath actuator 4804 may operate similarly to the sheath lock 706 of FIG. 9, as previously described. The slidable sleeve 4812 is fixably mounted to the outer housing 4810 and is slidably received within the coupling 4820. When the slidable sleeve 4812 is situated to position the sheath 103 containing the electrodes 207 and 211 at a desired location, the sheath lock 4806 is locked to secure the slidable sleeve 4812 in place. The sheath lock 4806 may be a spring loaded lock, a thumbscrew, or another similar mechanism as previously described with reference to FIGS. 7-10 to secure the slidable sleeve 4812 in place to secure the position of the sheath 103.

As previously described and as shown in the inset view, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. Before the sheath actuator 4804 is used to position the distal end 105 of the sheath 103 near the reference point 201, the distal end of the sheath 103 may initially rest at a position away from or immediately adjacent to the reference point 201.

Referring to FIGS. 51A and 51B and as used in conjunction with a user interface 4801, the sheath actuator 4804 is used to move the distal end 105 of the sheath 103 to a position closer to the reference point 201 as shown in the inset view. A relative movement of the outer housing 4810 toward the coupling 4820 by a distance 5019 moves the distal end 105 of the sheath 103 a corresponding distance to move the distal end 105 of the sheath 103 closer to the reference point 201. In turn, the distal end 209 of the primary electrode 207 and the distal end 213 of the secondary electrode 211 are also moved closer to the reference point 201. The relative movement of the outer housing 4810 toward the coupling 4820 is accomplished by the slidable sleeve 4812 being at least partially received within the coupling 5120 and then secured with the sheath lock 4806, as previously described.

FIGS. 52A-57C show how the user interface 4801 moves the electrodes 207 and 211 based on manipulation of the user interface 4801. Referring to FIG. 52A with regard to the user interface 4801, the primary actuator 4832 extends from the primary slider 4914 through the first guide slot 4831 of the outer housing 4810 and is situated at a first position 5233 within the first guide slot 4831 (as shown in the cross-sectional view taken along line A-A and in the top-down view). Correspondingly, as shown in the inset view, in an initial position the distal end 209 of the primary electrode 207 remains positioned within a distal end 105 of the sheath 103, with the distal end 105 of the sheath 103 having been positioned proximate the reference point 201. The distal end 213 of the secondary electrode 211 remains positioned within the distal end 209 of the primary electrode 207.

It should be noted that the secondary actuator 4952 and the intermediate guide slot 4933 are not yet exposed within the second guide slot 4851 in the outer housing 4810 and, thus, are represented by dashed lines in the top-down view. As will be appreciated, manipulation of the outer housing 4810 and the primary actuator 4832 brings the secondary actuator 4952 and the intermediate guide slot 4934 beneath the second guide slot 4851 in the outer housing 4810 where the secondary actuator 4952 may be subsequently engaged by a user.

It should also be noted that the primary actuator 4832 is fixably coupled to the primary electrode slider 4914 and the secondary actuator 4952 is fixably coupled to the secondary electrode slider 4916. Accordingly, linear or rotational movement of the primary actuator 4832 results in a corresponding movement of the primary electrode slider 4914 to move the primary electrode 5207. Correspondingly, linear or rotational movement of the secondary actuator 4852 results in a corresponding movement of the secondary electrode slider 4916 to move the secondary electrode 211. Thus, it should be understood that movement of the primary actuator 4832 may be regarded as causing movement of the primary electrode 207 and movement of the secondary actuator 4952 may be regarded as causing movement of the secondary electrode 211 without associated movement of the respective electrode slider being expressly described.

Referring to FIGS. 53A-53C, the primary actuator 4832 (extending through the first guide slot 4831 of the outer housing 4810 of the user interface 4801) has been moved by a user (not shown) to a second position 5335 within the first guide slot 4831 as shown in the cross-sectional view taken along line B-B and in the top-down view. The user may, for example, push the primary actuator 4832 forward to slide the primary actuator 4832 through the first guide slot 4831 to the second position 5335. Correspondingly, as shown in the inset view, in a second position, the distal end 209 of the primary electrode 207 extends beyond the distal end 105 of the sheath 103 toward the reference point 201 within the target tissue 202. The distal end 213 of the secondary electrode 211 remains positioned within the distal end 209 of the primary electrode 207.

The secondary actuator 4952 (extending through the intermediate guide slot 4934 of the primary electrode slider 4914 and the intermediate guide slot 4934 of the primary electrode slider 4914) are not yet exposed within the second guide slot 4851 in the outer housing 4810 and, thus, continue to be represented by dashed lines in the top-down view. However, it should be appreciated that, with movement of the primary actuator 4832 to the second position 5335 in the first guide slot 4831 brings the intermediate guide slot 4934 parallel with the second guide slot 4951 in the outer housing 4810. As described with reference to FIGS. 54A-54C, relative rotation of the primary actuator 4832 across the first guide slot 4831 brings the secondary actuator 4952 and the intermediate guide slot 4934 beneath the second guide slot 4951 in the outer housing 4810 where the secondary actuator 4952 may be subsequently engaged by a user.

Referring to FIGS. 54A-54C, the primary actuator 4832 (extending through the first guide slot 4831 of the outer housing 4810 of the user interface 4801) has been moved by the user (not shown) to a third position 5437 within the first guide slot 4831 as shown in the cross-sectional view taken along line C-C and in the top-down view. The user may, for example, rotate the primary actuator 4832 laterally while the primary electrode slider 4914 and the secondary electrode slider 4916 remain rotationally stationary to slide the primary actuator 4832 within the first guide slot 4831 to the third position 5437. As shown in the inset view, the relative position of the electrodes 207 and 211 has not changed. The distal end 209 of the primary electrode 207 remains extended beyond the distal end 105 of the sheath 103 near the reference point 201, as shown in FIG. 53C. Similarly, the distal end 213 of the secondary electrode 211 remains positioned within the distal end 209 of the primary electrode 207.

However, with movement of the primary actuator 4832 to the third position 5437, the secondary actuator 4952 extends through the intermediate guide slot 4934 of the primary electrode slider 4914 and now extends through the second guide slot 4851 in the outer housing 5810 of the user interface 4801. The intermediate guide slot 4934 in the primary electrode slider 4914 is overlapped by the second guide slot 4851 in the outer housing 4810. In this position, the secondary actuator 4952 rests at a first position 5453 within the second guide slot 4851. The secondary actuator 4952 may now be engaged by a user to extend the secondary electrode 211, as described with reference to FIGS. 55A-55C.

Referring to FIGS. 55A-55C, the secondary actuator 4952 extends through the first guide slot 4851 in outer housing 4810 of the user interface 4801 and is moved from the first location 5453 to a second location 5555 in the second guide slot 4851. At the second location 5555, the secondary actuator 4952 is now situated adjacent to the slidable actuator lock 4859, the operation of which is further described with reference to FIG. 56. The primary actuator 4832 extends through the first guide slot 4831 of the outer housing 4810 and remains at the third position 5437 within the first guide slot 4831. A user (not shown), for example, may push the secondary actuator 4952 to move the secondary actuator 4952 from the first position 5453 to the second position 5555 in the second guide slot 4851.

As shown in the inset view, with movement of the secondary actuator 4952, the distal end 213 of the secondary electrode 211 is extended beyond the distal end 209 of the primary electrode 207 to a location beyond the reference point 201. Electrical insulation 515 electrically isolates all but the distal end 213 of the secondary electrode 211 from the primary electrode 207. By contrast, with movement of the primary actuator 4832 toward the reference point 201 being limited by the first guide slot 4831, the distal end 209 of the primary electrode 207 remains in the same position as shown in FIG. 54C.

Referring to FIGS. 56A-56C, the secondary actuator 4952 extends through the intermediate guide slot 4934 in the primary electrode slider 4914 and is secured in place by the slidable actuator lock 4859. As previously described with reference to other embodiments of the user interface, once the distal end 213 of the secondary electrode 211 is extended to a desired location opposite the reference point 201 from the distal end 209 of the primary electrode 207, it may be desirable to maintain the secondary electrode 211 in place while the distal end 209 of the primary electrode 207 is partially withdrawn. Because the secondary electrode 211 extends through the primary electrode 209, withdrawal of the primary electrode 209 may apply force to the secondary electrode 211 that, potentially, could cause the distal end 213 of the secondary electrode 211 to retract. The slidable actuator lock 4859, however, may help prevent the secondary actuator 4952 from moving within the second guide slot 4851, thereby helping hold the distal end 213 of the secondary electrode 211 in place.

The slidable actuator lock 4859 slides across the second guide slot 4851 from a base 5669 and engages the secondary actuator 4952 to prevent the secondary actuator 4952 from moving from the second location 5555 in the second guide slot 4851. As a result, when the primary actuator 4832 is engaged to retract the primary electrode 207 as described with reference to FIGS. 57A-57C, the secondary actuator 4952 and, thus, the secondary electrode 211, remain in place.

Referring to FIGS. 57A-57C, with the secondary actuator 4952 secured at the second location 5555 in the second guide slot 4851 by the slidable actuator lock 4859, the primary actuator 4832 is engaged by a user (not shown) to partially retract the distal end 209 of the primary electrode 207. Specifically, the primary actuator 4832 (that extends from the primary slider 4914 through the first guide slot 4831 of the outer housing 4810 of the user interface 4801) has been moved by the user (not shown) to a fourth position 5739 within the first guide slot 4831 as shown in the top-down view and in the cross-sectional view taken along line E-E. The user may, for example, push the primary actuator 4832 to slide the primary actuator 4832 through the first guide slot 4831 to the fourth position 5739. As shown in the inset view, the position of the distal end 213 of the secondary electrode 211 remains unchanged relative to the reference point 201, because the secondary actuator 4952 is held in place by the slidable actuator lock 4859 at the second position 5555 in the second guide slot 4851. However, as shown in FIG. 57C, the distal end 209 of the primary electrode 207 has been partially retracted nearer to the distal end 105 of the sheath 103. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment.

The following pertains to removal of the device. Due to the primary actuator 4832 being located at the fourth position 5739 in the first guide slot 4831, the primary electrode 207 cannot be retracted until the primary actuator 4832 is moved to the third position 5437 within the first guide slot 4831, the slidable actuator lock 4859 unlocks the secondary actuator 4952 and the secondary actuator 4952 is retracted to the first position 5453 within the second guide slot 4851. Thus, accidental retraction of the primary electrode 207 cannot occur while the secondary electrode 211 is in the extended position.

Referring to FIG. 58, in another embodiment a user interface 5801 is provided for positioning electrodes conveyed by a sheath at a desired location at or near a reference point (none of which are shown in FIG. 58). The user interface 5801 includes a sheath actuator 5804, a primary housing 5830, a secondary housing 5850, and a lock rod 5870. As will be described in detail below, movement of the electrodes is accomplished by using the sheath actuator 5804 to position a sheath and to set a position of the lock rod 5870, rotating the secondary housing 5850 along a curve 5823 around an axis 5821 of the user interface 5801, and sliding the primary housing 5850 along the axis 5821. The primary housing 5830 is mechanically secured to a primary electrode (not shown in FIG. 58) such that sliding the primary housing 5830 slides the primary electrode. Similarly, the secondary housing 5850 is mechanically secured to a secondary electrode (not shown in FIG. 58) such that sliding the secondary housing 5850 slides the secondary electrode. By contrast with previous embodiments described with reference to FIGS. 11-57, the user interface 5801 does not include actuators or levers used to manipulate the position of the electrodes. Instead, manipulation of the electrodes is performed by sliding and rotating the secondary housing 5850 and sliding the primary housing 5830, as further described below.

Referring to FIG. 59, in a particular embodiment, the coupling 5820 is configured to engage a port on an electrosurgical apparatus, such as a bronchoscope, as described with reference to FIGS. 1, 7, and 8. The coupling 5820 slidably receives the primary housing 5830 and the lock bar 5870. Once the sheath (not shown in FIG. 59) is disposed at a desired location relative to the reference point (also not shown in FIG. 59), a sheath lock 5806 may be used to fix the sheath in place and also to fix a position of the lock bar 5870 relative to the reference point. The primary housing 5830 and the lock bar 5870 also are slidably and rotatably received within the secondary housing 5850. As described in detail below, the sliding and rotation of the primary housing 5830 and the lock bar 5870 relative to the secondary housing 5850 controls the relative movement and fixing of positions of the primary housing 5830 and the secondary housing 5850 and, thus, the relative movement and fixing positions of the primary and secondary electrode, respectively.

Referring to FIGS. 60A and 60B, operation of the sheath actuator 5804 is described to explain positioning of the sheath 105 and the lock bar 5870. As further described below, in an initial configuration, sliding of the secondary housing 5850 also slides the primary housing 5830. Thus, sliding the secondary housing 5850 slides the primary housing 5830 relative to the coupling 5820.

Referring to FIGS. 61A and 61B, movement of the secondary housing 5850 through the distance 6019 results in the primary housing 5830 advancing through the distance 6019 into the coupling 5820. Correspondingly, the sheath 103 advances into the body to move the distal end 105 of the sheath 103 toward the reference point 202. In this configuration, movement of the secondary housing 5850 also causes the distal end 209 of the primary electrode 207 (which rests within the distal end 105 of the sheath 103) and the distal end 213 of the secondary electrode 211 (which rests within the distal end 209 of the primary electrode 207) to be correspondingly advanced toward the reference point. Once the distal end 105 of the sheath 103 reaches a desired location relative to the reference point 202, the sheath lock 5806 may be used to lock the sheath 103 in place. In a particular embodiment, the sheath lock 5806 also may lock a position of the lock rod 5870, which thereby fixes a reference position for positioning of the primary housing 5830 and the secondary housing 5850, as will be further described below.

FIGS. 62-64C illustrate components of the user interface 5801. Referring to FIG. 62, the lock rod 5870 includes a positioning section 6271 and a locking section 6273. The positioning section 6271 may be received and secured, for example, in the coupling 5820 as previously described to fix a position of the lock rod. The locking section 6273 supports a plurality of outwardly-extending teeth 6275 which are engaged by one or more inward facing teeth supported by the primary housing 5830 and the secondary housing 5850, as further described below, to facilitate locking positions of the housings 5830 and 5850 to prevent them from sliding along the lock rod 5870.

Referring to FIG. 63A, a first side of the primary housing 5830 is shown. In a particular embodiment, the primary housing 5830 is generally cylindrical in shape to permit sliding and rotating within a chamber within the secondary housing 5850, as further described with reference to FIGS. 64A-70C. The primary housing 5830 includes an outward-facing guide slot 6333 configured to receive a guide member (not shown in FIG. 63A) extending inwardly from a secondary housing 5850. The engagement of the guide member with the guide slot 6333 controls relative movement of the primary housing 5830 and the secondary housing 5850, as further described below.

Referring to FIG. 63B, a second side of the primary housing 5830 is shown. In a particular embodiment, the primary housing 5830 includes a primary lock channel 6335 that is configured to receive the lock rod 5870. Within the primary lock channel 6335, one or more inwardly-facing teeth 6337 are configured to engage the teeth 6275 extending from the lock rod 5870 to prevent the primary housing 5830 from sliding relative to the lock rod 5870 when the lock rod 5870 is received within the primary lock channel.

Referring to FIG. 63C, a cross-sectional view of the primary housing 5830 shows the guide slot 6333 and the primary lock channel 6335. At the point along the primary housing 5830 where the cross-sectional view of FIG. 64C is taken, the guide slot 6333 enables sliding of the guide member (not shown) within the guide slot 6333 because, with reference to FIG. 63A, there are no transverse sides of the guide slot 6333 at this location to block sliding of the guide member. The primary lock channel 6335 includes a groove configured to receive the lock bar 5870. It should be noted that the primary housing 5830 defines an open core 6334 through which the primary electrode, the secondary electrode, the sheath, or other apparatuses (none of which are shown in FIG. 63C) may extend or may be received.

Referring to FIG. 63D, another cross-sectional view of the primary housing 5830 shows the guide slot 6333 and the primary lock channel 6335. At the point along the primary housing 5830 where the cross-sectional view of FIG. 64D is taken, the guide slot 6333 enables rotating of the guide member (not shown) across the guide slot 6333, although, with reference to FIG. 63A, adjacent transverse sides may block sliding of the guide member. Within the primary lock channel 6335, the one or more teeth 6337 extend to engage the teeth 6275 on the lock bar 5870 when it is received within the primary lock channel 6335 to prevent the primary housing 5830 from sliding along the lock bar 5870.

Referring to FIG. 64A, a side view of the secondary housing 5850 is shown. As previously stated, in contrast to the embodiment of the user interface 4801 of FIGS. 48-57, the secondary housing 5850, which is an outer housing, does not support levers, separate actuators, or openings through which such levels and separate actuators extend. Instead, the secondary housing 5850 in and of itself is an actuator to be engaged by a user to manipulate positions of electrodes (not shown in FIG. 64A). In the illustrated embodiment, the secondary housing 5850 is shown to have a cylindrical outer shape, but the secondary housing 5850 may support knurled grips or feature a different outer shape that may be desirable for holding or manipulating the user interface.

Referring to FIGS. 64B and 64C, cross-sectional views of the secondary housing 5850 show an inner channel 6454 defined by an inner wall 6452 that is configured to slidably and rotatably receive the primary housing 5830. A secondary lock channel 6458 defined by a secondary channel wall 6456 is configured to receive the lock bar 5870 which, as described below, may slide within the secondary lock channel 6458 or be moved across the secondary lock channel 6458 by the rotation of the secondary housing 5850 to selectively reposition the lock bar 5870.

The secondary channel 6458 includes three lobes which control relative movement of the housings 5830 and 5850 relative to the lock bar 5870 as described in detail with reference 65A-65C, 66A-66C, 67A-67C, 68A-68C, 69A-69C, and 70A-70C. With the lock bar 5870 in a first lobe 6461, the primary housing 5830 and the secondary housing 5850 may slide freely relative to the lock bar 5870. With the lock bar 5870 in a second lobe 6463, the secondary channel wall 6456 presses against the lock rod 5870, causing the lock rod 5870 to engage the teeth 6337 in the primary lock channel 6335 of the primary housing 5830, thereby preventing the primary housing 5830 from sliding relative to the lock rod 5870. However, with the lock rod 5870 in the second lobe 6463, the secondary housing 5850 remains free to slide relative to the lock bar 5870. In a third lobe 6465, one or more inward-facing teeth 6459 configured to engage the outward-facing teeth 6275 extending from the lock bar 5870. Thus, with the lock bar 5870 in the third lobe 6465, the secondary housing 5850 is blocked from sliding relative to the lock bar 5870. However, when the lock bar 5870 is in the third lobe 6465, the teeth 6337 in the primary lock channel 6335 of the primary housing 5830 no longer engage the lock rod 5870, so the primary housing 5830 is free to slide relative to the lock bar 5870.

Referring again to FIG. 64C, an inwardly-extending guide member 6455 is configured to be received within the guide slot 6333 of the primary housing 5830 described with reference to FIGS. 63A and 63C. Engagement of the guide member 6455 with the guide slot 6333 controls relative movement of the primary housing 5830 and the secondary housing 5850, as further described below.

Referring to FIG. 65A, a side view of the user interface 5801 is shown in an initial configuration for extending both the primary electrode 207 and the secondary electrode 211 (FIG. 65D). FIGS. 65A-70D are used to illustrate how movement of the user interface 5801 is used to control positions of the distal end 209 of the primary electrode 207 and the distal end 213 of the secondary electrode 211 within a body. Specifically, sliding and rotating of the outer, secondary housing 5850 and sliding of the inner, primary housing 5830 positions the electrodes 207 and 211 relative to reference point 202. It should be noted that in the side views of the user interface 5801 of FIGS. 65A, 66A, 67A, 68A, 69A, and 70A, the coupling 5820 and the secondary housing 5850 are shown in cutaway views (represented by dashed lines) to show the relative movement of the primary housing 5830 relative to the coupling 5820 and the secondary housing 5850. Also in the views of FIGS. 65A, 66A, 67A, 68A, 69A, and 70A, the lock rod 5870 would be positioned behind the user interface and, thus, is not shown in FIGS. 65A, 66A, 67A, 68A, 69A, and 70A. However, the lock bar 5870 and its engagement with the primary housing 5830 and the secondary housing 5850 are shown in the cross-sectional views, such as shown in the cross-sectional views of FIGS. 65B and 65C. Movement of the electrodes 207 and 211 relative to the reference point is shown in the corresponding inset views, such as shown in FIG. 65D.

Referring again to FIG. 65A, in the initial configuration for extending both the primary electrode 207 and the secondary electrode 211, the guide member 6455 is received in a first transverse guide segment 6541 of the guide slot 6333 of the secondary housing 5850 (FIG. 65D). With the guide member 6455 of the secondary housing 5850 engaged in the first transverse guide segment 6541 of the guide slot 6333 of the primary housing 5830, the housings 5830 and 5850 can only be moved in concert along the axis 5821 (FIG. 58) of the user interface 5801.

Referring to FIGS. 65B and 65C, with the guide member 6455 in the first transverse guide segment 6541 of the guide slot 6333, the lock rod 5870 is received in a first lobe 6561 of the secondary lock channel 6458. When received in the first lobe 6561 of the secondary lock channel 6458, neither the teeth 6459 in the secondary lock channel 6458 of the secondary housing 5850 nor the teeth 6337 in the primary lock channel 6335 engage the lock rod 5870. Thus, both the primary housing 5830 and the secondary housing 5850 may slide freely relative to the lock rod 5870, although, as previously described, the engagement of the guide member 6455 with the guide slot 6333 cause the primary housing 5830 and the secondary housing 5850 to move in concert (i.e., to move simultaneously through the same distance).

Referring to FIG. 66A, a side view of the user interface 5801 is shown in a second configuration once the distal end 209 of the primary electrode 207 and the distal end 213 of the secondary electrode 211 have been extended into the reference point 201 as shown in FIG. 66D. As described with reference to FIG. 65A, engagement of the guide member 6455 with the guide slot 6333 of the secondary housing 5850 causes the primary housing 5830 and the secondary housing 5850 to move in concert through a distance 6691. As shown in FIGS. 66B and 66C, and as previously explained with reference to FIGS. 65B and 66C, the lock rod 5870 is in the first lobe 6461 of the secondary lock channel 6456 where it does not engage the teeth 6459 in the secondary lock channel 6458 of the secondary housing 5850 or the teeth 6337 in the primary lock channel 6335, enabling the primary housing 5830 and the secondary housing 5850 to slide freely relative to the lock rod 5870.

Referring to FIG. 67A, the secondary housing 5850 is rotated in a direction 6793 to move the guide member 6455 into a second segment 6743 of the guide slot 6333. With the guide member 6455 in the second segment 6743 of the guide slot 6333, the secondary housing 5850 is free to move relative to the primary housing 5830. However, the guide slot 6333 blocks further rotation of the guide member 6455 in the direction 6793.

Referring to FIGS. 67B and 67C, it can be seen that the rotation of the secondary housing 5850 results in the lock rod 5870 moving into the second lobe 6463 of the secondary lock channel 6458 where the secondary channel wall 6456 impinges upon the lock rod 5870 so that the lock rod 5870 engages the teeth 6337 in the primary lock channel 6335 of the primary housing 5830, thus preventing the primary housing 5830 from sliding relative to the lock rod 5870. However, with the lock rod 5870 in the second lobe 6463, the secondary housing 5850 remains free to slide relative to the lock rod 5870. Referring to FIG. 67D, it can be seen that the rotation of the secondary housing 5850 does not result in movement of the electrodes 207 and 211.

Referring to FIG. 68A, the secondary housing 5850 is slidably moved through a distance 6891, independently of the primary housing 5830, to extend the distal end 213 of the secondary electrode 211 to an opposing side of the reference point 202 from the distal end 209 of the primary electrode 207. The guide member 5455 now extends into a third segment 6845 of the guide slot 6333 where the guide member 6455 is limited from further sliding in the direction of the distance 6891, but is free to move across the guide slot 6333 to permit rotation of the secondary housing 5850 relative to the primary housing 5830.

Referring to FIGS. 68B and 68C, it can be seen that the lock rod 5870 remains in the second lobe 6463 of the secondary lock channel 6458. Thus, the secondary channel wall 6456 continues to impinge upon the lock rod 5870 so that the lock rod 5870 engages the teeth 6337 in the primary lock channel 6335 of the primary housing 5830, thus continuing to prevent the primary housing 5830 from sliding relative to the lock rod 5870. With the lock rod 5870 remaining in the second lobe 6463, the secondary housing 5850 continues to be free to slide relative to the lock rod 5870.

Referring to FIG. 69A, the secondary housing 5850 is rotated in a direction 6993. The guide member 5455 now extends into a fourth segment 6947 of the guide slot 6333 where the guide member 6455 is limited from further rotating in the direction 6993, but now permits relative sliding movement of the primary housing 5830 relative to the secondary housing 5850.

Referring to FIGS. 69B and 69C, it can be seen that the lock rod 5870 moves into the third lobe 6465 of the secondary lock channel 6458. As a result, the lock rod 5870 no longer engages the teeth 6337 in the primary lock channel 6335 of the primary housing 5830, enabling the primary housing 5830 to slide relative to the lock bar 5870. However, with rotation of the secondary housing 5850 causing the lock bar 5870 to be received into the third lobe 6465 of the secondary lock channel 6458, the teeth 6459 extending from the secondary housing 5850 now engage the lock rod 5870, thereby preventing sliding movement of the secondary housing 5850 relative to the lock rod 5870. Referring to FIG. 69D, it should be noted that the rotation of the secondary housing 5850 again results in no movement of the electrodes 207 and 211.

Referring to FIG. 70A, the primary housing 5830 is moved through a distance 7091 to partially retract the primary housing 5830 within the secondary housing 5850 to partially retract the distal end 209 of the primary electrode 207 away from the distal end 213 of the secondary electrode 211 as shown in FIG. 70D. The primary housing 5830 is free to slide relative to the lock rod 5870. As previously described with reference to FIGS. 69B and 69C and as shown in FIGS. 70B and 70C, the rotation of the secondary housing 5850 caused the lock rod 5870 to be rotated into the third lobe 6465 of the secondary lock channel 6458 in the secondary housing 5850. As a result, the lock rod 5870 was moved away and disengaged from the teeth 6337 in the primary lock channel 6355 of the primary housing 5830. With the lock rod 5870 in the third lobe 6465 of the secondary lock channel 6458 of the secondary housing 5850, the lock rod 5870 engages the teeth 6459 in the third lobe 6465 of the secondary lock channel 6458 of the secondary housing 5850, thereby preventing the secondary housing 5850 from sliding relative to the lock bar 5870. In this manner, once the secondary electrode 211 has been extended and secured in position, the primary electrode 207 may be moved to position the distal end 209 of the primary electrode 207 relative to the distal end 213 of the secondary electrode 211 to facilitate application of an electric current to provide desired treatment.

It will be appreciated that the illustrative embodiment of the user interface described with reference to FIGS. 62-70D describe significant detail in the structure and operation of the user interface 5801, but has set forth relatively simple manipulation—of only the secondary housing 5850 to position the electrodes 207 and 211 until the primary housing 5830 is retracted in a final step. In furtherance thereof, FIGS. 71A-76B are provided to illustrate operation of the embodiment of the user interface described with reference to FIGS. 62-70D.

Figure 71A:
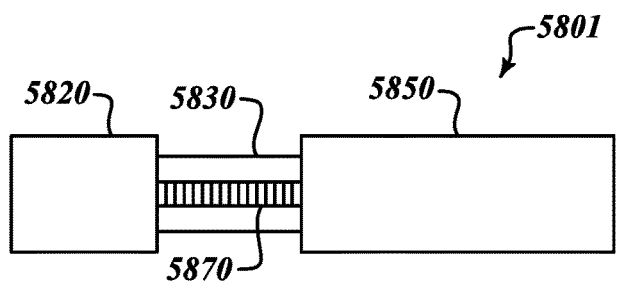
Figure 71B:
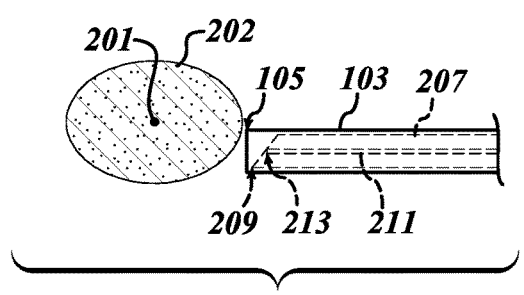

Referring to FIG. 71A, the user interface 5801 is shown in readiness for deployment of the electrodes 207 and 211 in the vicinity of the reference point 202. As shown in FIG. 71B, the distal end 209 of the primary electrode 207 rests inside the distal end 105 of the sheath 103 and the distal end 213 of the secondary electrode 211 rests inside the distal end 209 of the primary electrode 207.

Figure 72A:
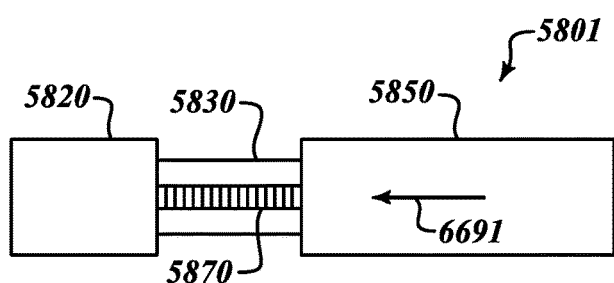
Figure 72B:
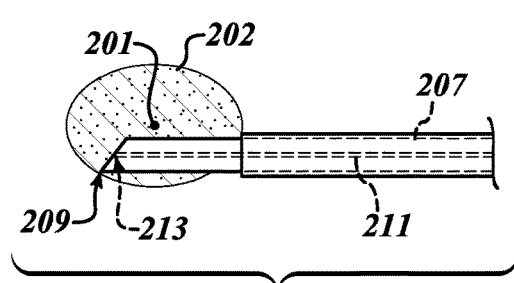

Referring to FIG. 72A, the user interface 5801 is shown with the secondary housing 5850 and the primary housing 5830 moved in the direction 6691 to, as shown in FIG. 72B, simultaneously extend the distal end 209 of the primary electrode 207 and the distal end 213 of the secondary electrode 211 into the reference point 202, as previously described with reference to FIGS. 66A-66D.

Figure 73A:
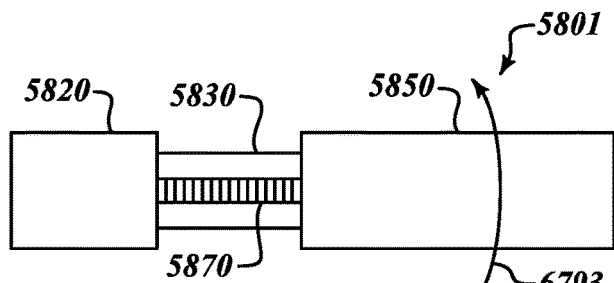
Figure 73B:
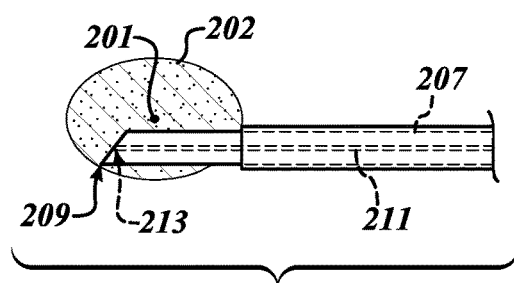

Referring to FIG. 73A, the user interface 5801 is shown with the secondary housing 5850 rotated in the direction 6793 to, as shown in FIG. 73B, secure the primary electrode 207 from being moved relative to the reference point 202. The primary electrode 207 is thus secured in place while, the secondary housing 5850 is remains free to slide, as previously described with reference to FIGS. 67A-67D.

Figure 74A:
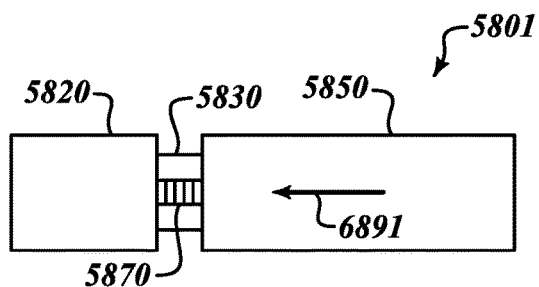
Figure 74B:
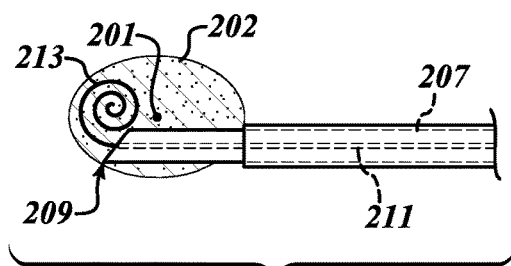

Referring to FIG. 74A, the user interface 5801 is shown with the secondary housing 5850 moved in the direction 6891 to, as shown in FIG. 74B, extend the distal end 213 of the secondary electrode 211 across the reference point 202, as previously described with reference to FIGS. 68A-68D.

Figure 75A:
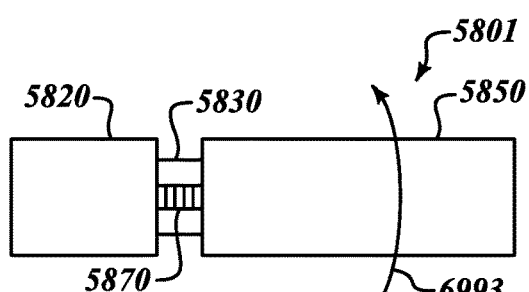
Figure 75B:
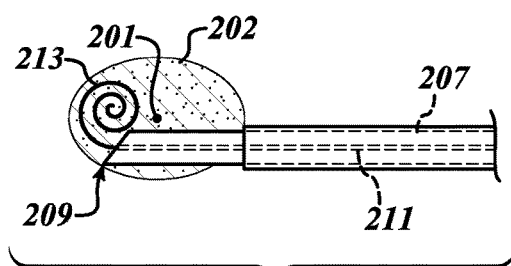

Referring to FIG. 75A, the user interface 5801 is shown with the secondary housing 5810 rotated in the direction 6993 to, as shown in FIG. 75B, secure the distal end 213 of the secondary electrode 211 in place across the reference point 202 while preparing for the partial retraction of the distal end 209 of the primary electrode 207, as previously described with reference to FIGS. 69A-69D.

Figure 76A:
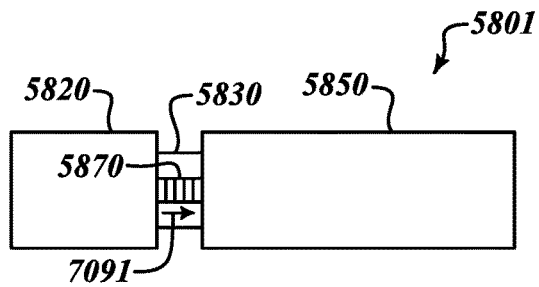
Figure 76B:
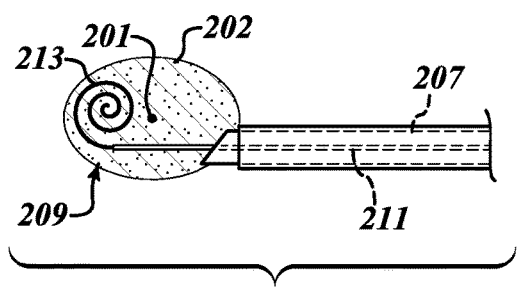

Referring to FIG. 76A, the user interface 5801 is shown with the primary housing 5830 moved in the direction 7091 as previously described with reference to FIGS. 70A-70D to partially retract the distal end 209 of the primary electrode 207. As shown in FIG. 76B, the distal end 209 of the primary electrode 207 is thus partially withdrawn from the reference point 202 while leaving the distal end 213 of the secondary electrode 211 in place, thereby readying the electrodes 207 and 211 for administration of treatment.

Figure 77:
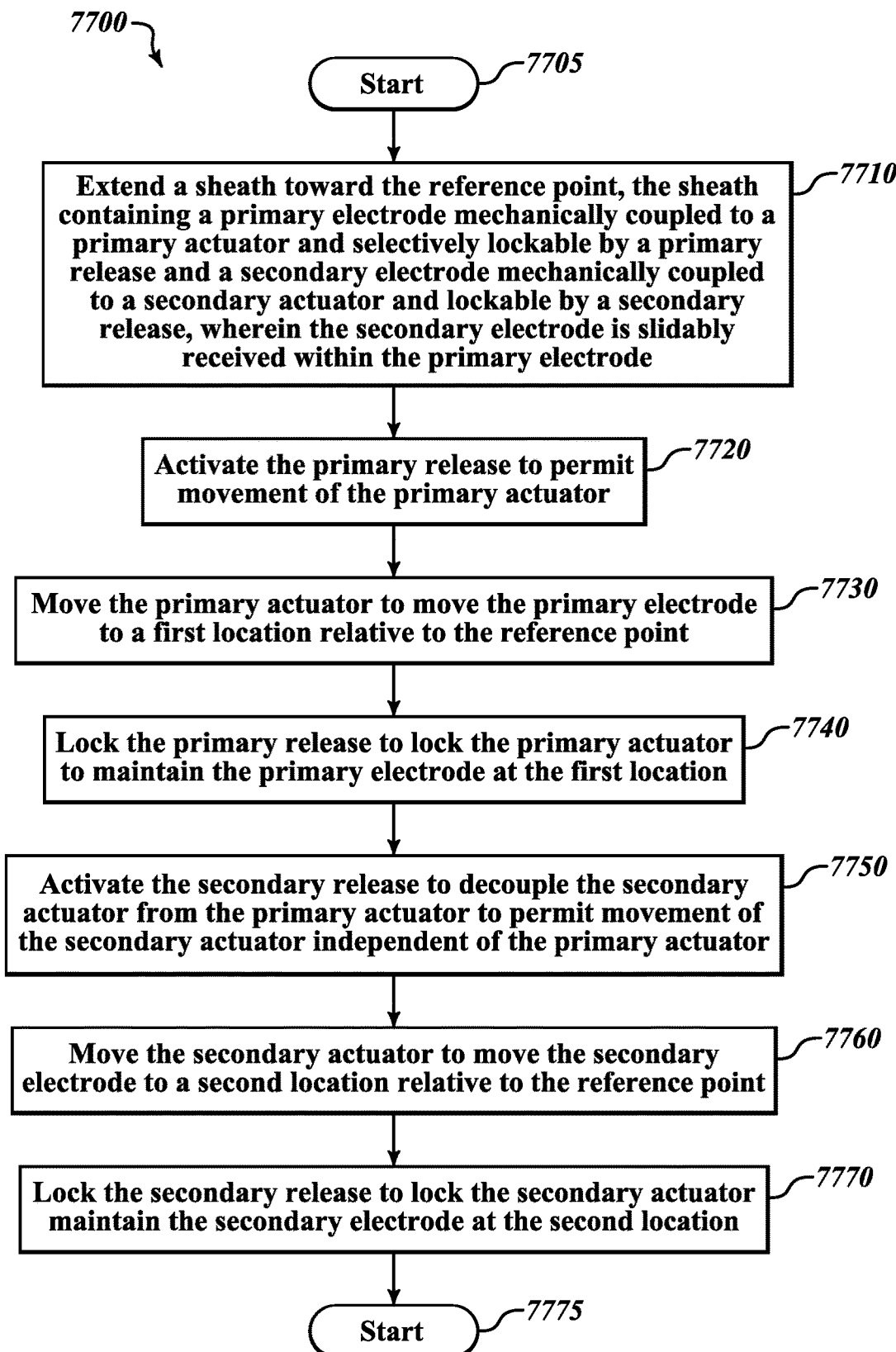

Referring to FIG. 77, an illustrative method 7700 of positioning electrodes for treatment is provided. The method 7700 starts at a block 7705. At a block 7710, a sheath containing a primary electrode and a secondary electrode is extended, where the secondary electrode is contained within the primary electrode and initially coupled to move with the primary electrode as previously described, for example, with reference to FIGS. 8, 51, and 61. At a block 7720, the primary electrode is moved to a first location near a reference point as previously described, for example, with reference to FIGS. 14, 38, 53, and 64. At a block 7730, the primary electrode is locked in position at the first location as previously described, for example, with reference to FIGS. 14, 38, 54, and 65. At a block 7740, movement of the secondary electrode (independent of the primary electrode) is unlocked as previously described, for example, with reference to FIGS. 19, 44, 54, and 65. At a block 7750, the secondary electrode is moves to a second location near the reference point as previously described, for example, with reference to FIGS. 20, 45, 55, and 66. At a block 7760, the secondary electrode is locked in position at the second position as previously described, for example, with reference to FIGS. 26, 46, 55, and 68. The method 7700 ends at a block 7765, with the electrodes now positioned for the administration of treatment.

Figure 78:
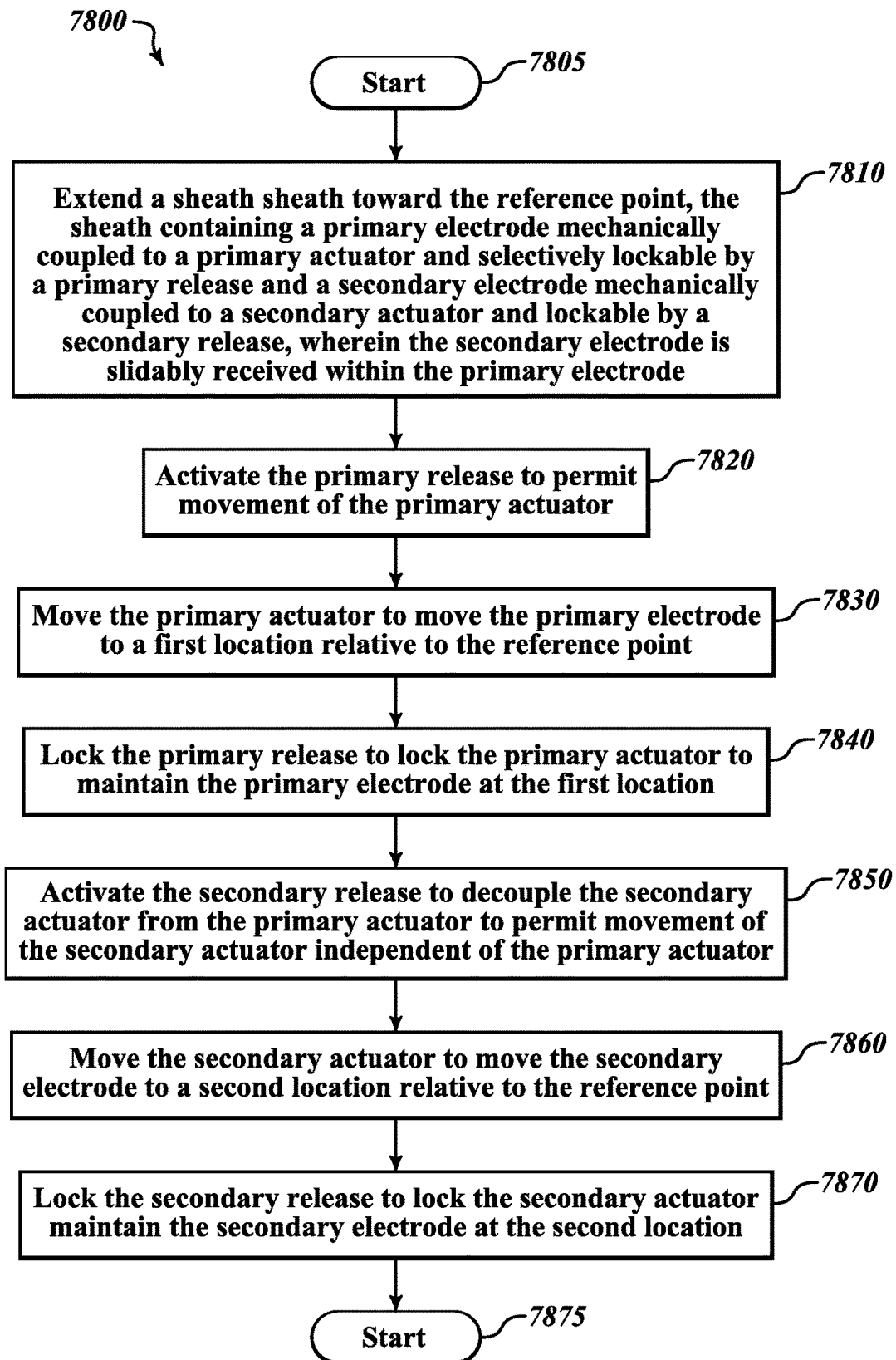

Referring to FIG. 78, an illustrative method 7800 of positioning electrodes for treatment is provided. The method 7800 relates to the use of a user interface as previously described, for example, with reference to FIGS. 11-34.

The method 7800 starts at a block 7805. At a block 7810, a sheath is extended toward a reference point, the sheath containing a primary electrode mechanically coupled to a primary actuator and selectively lockable by a primary release and a secondary electrode mechanically coupled to a secondary actuator and lockable by a secondary release, wherein the secondary electrode is slidably received within the primary electrode. At a block 7820, the primary release is activated to permit movement of the primary actuator as previously described, for example, with reference to FIG. 13. At a block 7830, the primary actuator is moved to move the primary electrode to a first location relative to the reference point as previously described, for example, with reference to FIG. 13. At a block 7840, the primary release is locked to lock the primary actuator to maintain the primary electrode at the first location as previously described, for example, with reference to FIG. 14.

At a block 7850, the secondary release is activated to decouple the secondary actuator from the primary actuator to permit movement of the secondary actuator independent of the primary actuator as previously described, for example, with reference to FIG. 19. At a block 7860, the secondary actuator is moved to move the secondary electrode to a second location relative to the reference point as previously described, for example, with reference to FIG. 20. At a block 7870, the secondary release is locked to lock the secondary actuator to maintain the secondary electrode at the second location as previously described, for example, with reference to FIG. 20. The method 7800 ends at a block 7875, with the electrodes now positioned for the administration of treatment.

Figure 79:
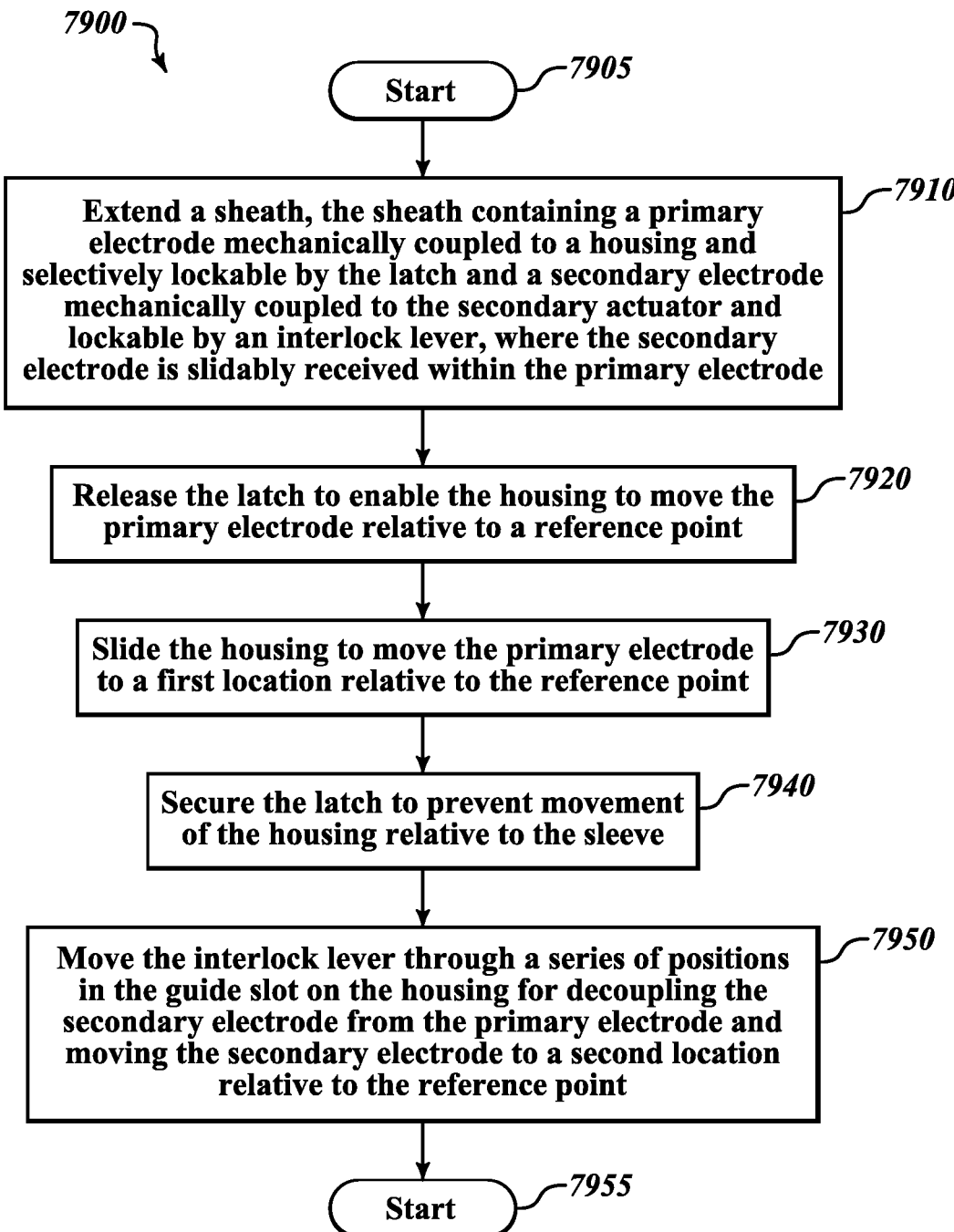

Referring to FIG. 79, an illustrative method 7900 of positioning electrodes for treatment is provided. The method 7900 relates to the use of a user interface as previously described, for example, with reference to FIGS. 35-47.

The method 7900 starts at a block 7905. At a block 7910, a sheath is extended, with the sheath containing a primary electrode mechanically coupled to a housing and selectively lockable by the latch and a secondary electrode mechanically coupled to the secondary actuator and lockable by an interlock lever, where the secondary electrode is slidably received within the primary electrode. At a block 7920, the latch is released to enable the housing to move the primary electrode relative to a reference point as previously described, for example, with reference to FIG. 38. At a block 7930, the housing is slid to move the primary electrode to a first location relative to the reference point as previously described, for example, with reference to FIG. 38. At a block 7940, the latch is secured to prevent movement of the housing relative to the sleeve as previously described, for example, with reference to FIG. 38. At a block 7950, the interlock lever is moved through a series of positions in the guide slot on the housing for decoupling the secondary electrode from the primary electrode and moving the secondary electrode to a second location relative to the reference point as previously described, for example, with reference to FIGS. 44-46. The method 7900 ends at a block 7955, with the electrodes now positioned for the administration of treatment.

Figure 80:
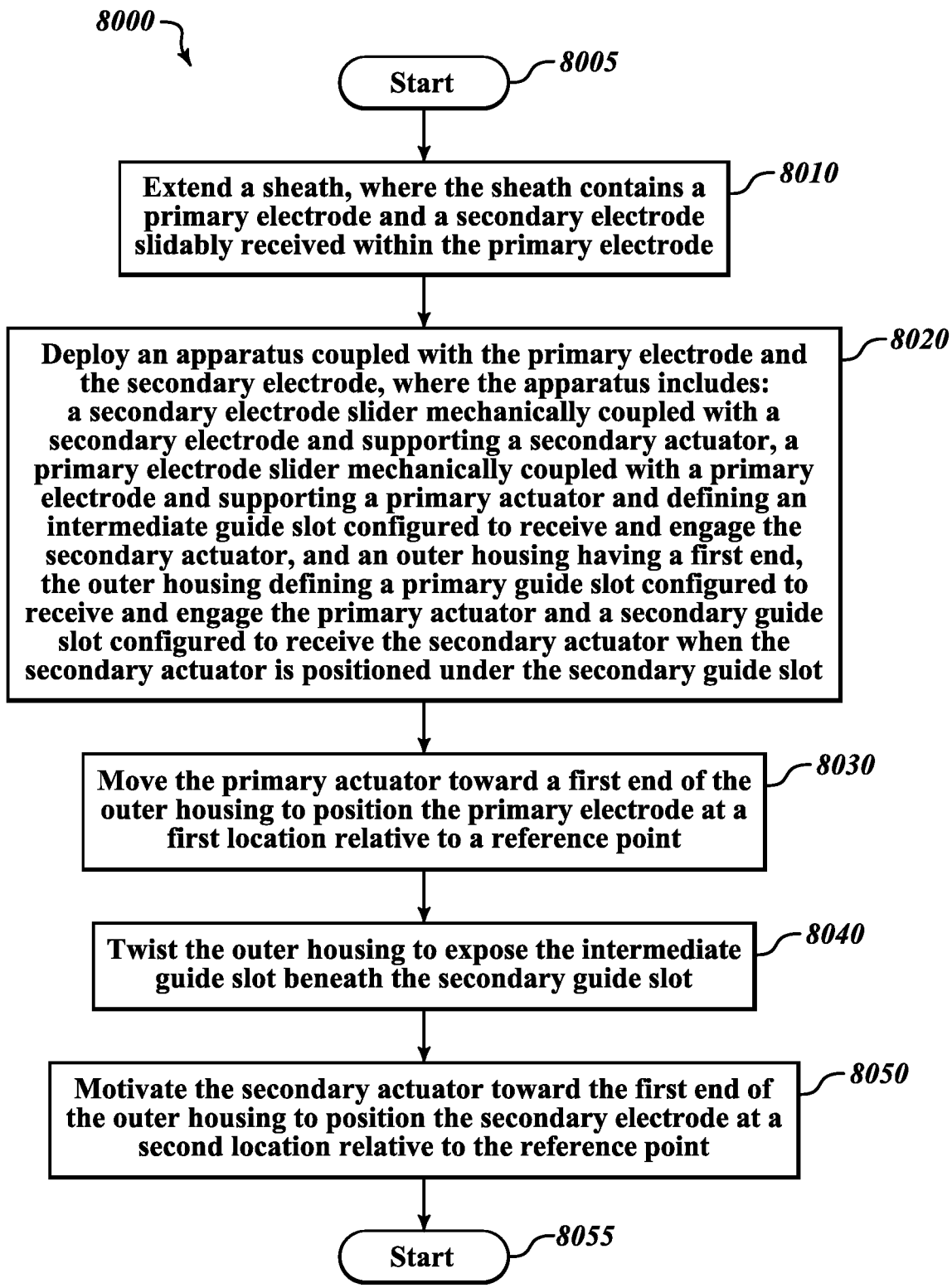

Referring to FIG. 80, an illustrative method 8000 of positioning electrodes for treatment is provided. The method 8000 relates to the use of a user interface as previously described, for example, with reference to FIGS. 48-57.

The method 8000 starts at a block 8005. At a block 8010, a sheath is extended, where the sheath contains a primary electrode and a secondary electrode slidably received within the primary electrode as previously described, for example, with reference to FIG. 51.

At a block 8020, an apparatus coupled with the primary electrode and the secondary electrode is deployed. The apparatus includes a secondary electrode slider mechanically coupled with a secondary electrode and supporting a secondary actuator. The apparatus also includes a primary electrode slider mechanically coupled with a primary electrode and supporting a primary actuator, and also defining an intermediate guide slot configured to receive and engage the secondary actuator. The apparatus also includes an outer housing having a first end, with the outer housing defining a primary guide slot configured to receive and engage the primary actuator and a secondary guide slot configured to receive the secondary actuator when the secondary actuator is positioned under the secondary guide slot, all as previously described, for example, with reference to FIGS. 48-57.

At a block 8030, the primary actuator is moved toward the front end of the outer housing to position the primary electrode at a first location relative to the reference point as previously described, for example, with reference to FIG. 53. At a block 8040, the outer housing is rotated to expose the intermediate guide slot beneath the second guide slot as previously described, for example, with reference to FIG. 54. At a block 8050, the secondary actuator is moved toward the front end of the outer housing to position the secondary electrode at a second location relative to the reference point as previously described, for example, with reference to FIG. 55. The method 8000 ends at a block 8055, with the electrodes now positioned for the administration of treatment.

Figure 81:
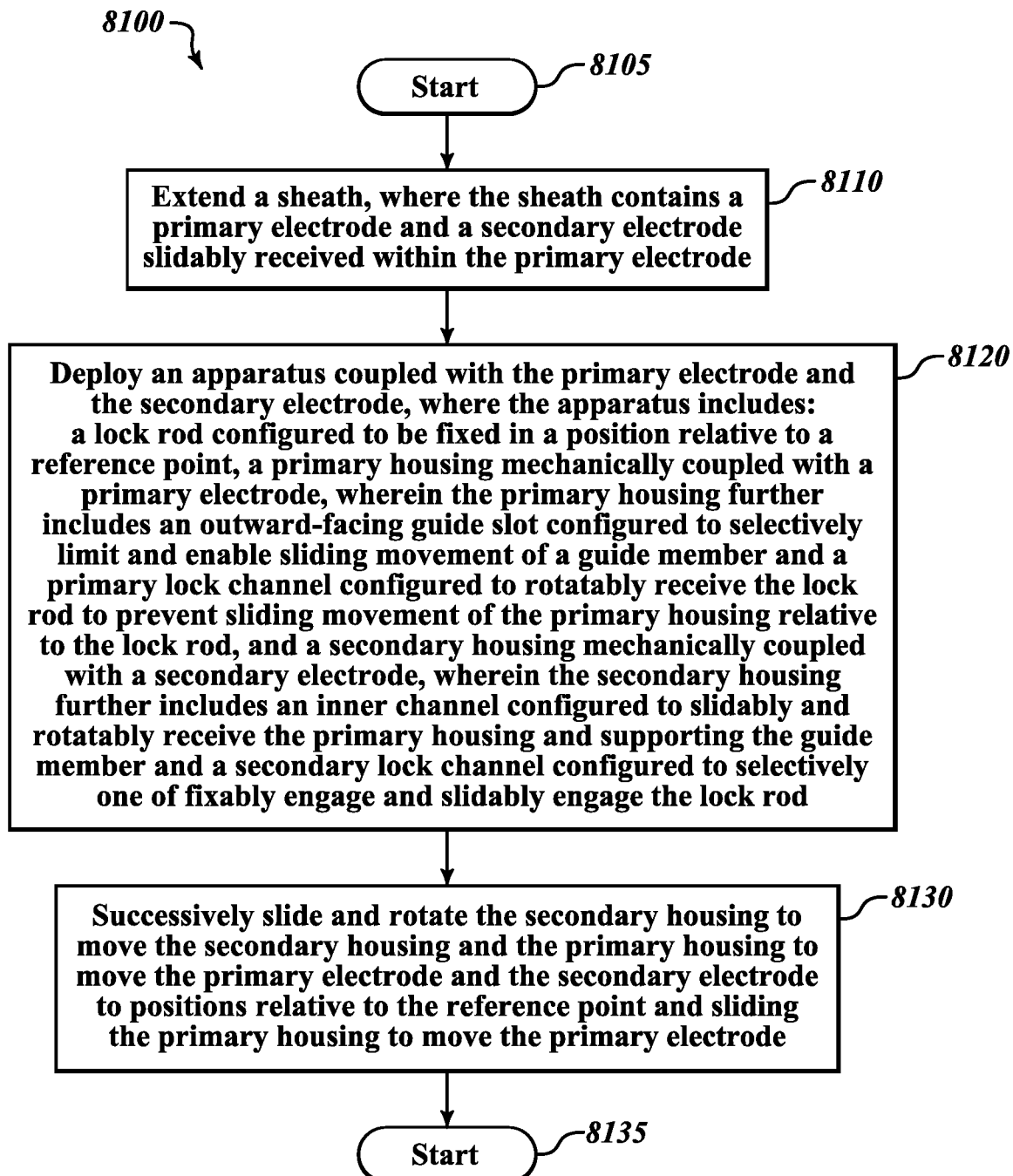

Referring to FIG. 81, an illustrative method 8100 of positioning electrodes for treatment is provided. The method 8100 relates to the use of a user interface as previously described, for example, with reference to FIGS. 58-76.

The method 8100 starts at a block 8105. At a block 8010, a sheath is extended, where the sheath contains a primary electrode and a secondary electrode slidably received within the primary electrode as previously described, for example, with reference to FIG. 61.

At a block 8120, an apparatus coupled with the primary electrode and the secondary electrode is deployed. The apparatus includes a secondary electrode slider mechanically coupled with a secondary electrode and supporting a secondary actuator. The apparatus includes a lock rod configured to be fixed in a position relative to a reference point. The apparatus also includes a primary housing mechanically coupled with a primary electrode. The primary housing also includes an outward-facing guide slot configured to selectively limit and enable sliding movement of a guide member and a primary lock channel configured to rotatably receive the lock rod to prevent sliding movement of the primary housing relative to the lock rod. The apparatus further includes a secondary housing mechanically coupled with a secondary electrode. The secondary housing further includes an inner channel configured to slidably and rotatably receive the primary housing and supporting the guide member. The secondary housing also includes a secondary lock channel configured to selectively one of fixably engage and slidably engage the lock rod.

At a block 8130, the secondary housing is successively slide and rotated to move the secondary housing and the primary housing to move the primary electrode and the secondary electrode to positions relative to the reference point and the primary housing is slide to move the primary electrode, for example, with reference to FIGS. 65A-76. The method 8000 ends at a block 8035, with the electrodes now positioned for the administration of treatment.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus for slidably moving multiple features relative to a sheath inserted into a body and positioned relative to a reference point, the device comprising:
   a primary electrode;
   a secondary electrode;
   a primary actuator configured to move the primary electrode in a first direction and in a second direction opposite to the first direction;
   a secondary actuator configured to move the secondary electrode in the first direction and the second direction; and
   a control mechanism configured to selectively mechanically engage the first actuator and the second actuator to:
   upon the first actuator being moved into at least one first position,
      movement of the secondary actuator in either of the first direction
      and the secondary direction is automatically blocked by engagement of the control mechanism with the primary actuator;
   upon the second actuator being moved into at least one second position,
      movement of the primary actuator in either of the first direction
      and the secondary direction is automatically blocked by engagement of the control mechanism with the secondary actuator; and
   lock positions of the primary actuator and the secondary actuator.

2. The apparatus of claim 1, further comprising:
   a sheath actuator configured to move a sheath relative to the reference point; and
   a sheath lock configured to fix a position of the sheath relative to the reference point.

3. The apparatus of claim 1, wherein the control mechanism includes an actuator interlock configured to prevent movement of the primary actuator while the secondary electrode is moved independently of the primary electrode to deploy the secondary electrode.

4. The apparatus of claim 3, wherein the actuator interlock is further configured to restrict movement of the secondary actuator within a selected range.

5. The apparatus of claim 3, wherein the actuator interlock is further configured to prevent movement of the secondary actuator while the primary actuator is moved to partially retract the primary electrode in the second direction.

6. The apparatus of claim 1, wherein the control mechanism includes at least one trigger configured to be activated to unlock motion of at least one of the primary actuator and the secondary actuator.

7. The apparatus of claim 1, wherein the control mechanism includes at least one guide channel configured to selectively permit movement of one of the primary actuator and the secondary actuator.

8. The apparatus of claim 7, wherein the guide channel is configured to enable at least one of:
rotating of the primary actuator to unlock motion of the primary actuator;
rotating of the secondary actuator to unlock motion of the secondary actuator;
sliding of the primary actuator to move the primary electrode within a first range of motion; and
sliding of the secondary actuator to move the secondary electrode within a second range of motion.

9. The apparatus of claim 1, further comprising a position indicator configured to indicate a distance of travel of the primary electrode relative to the reference point.

10. A system for treating tissue at a reference point, the system comprising:
a controllable electrical power source configured to selectively provide electrical power between a first pole and a second pole;
an electrosurgical apparatus configured to be inserted into a body to convey a sheath containing a primary electrode electrically coupled to the first pole of the electrical power source and a secondary electrode electrically coupled to the second pole of the electrical power source to a vicinity of a reference point;
a sheath actuator configured to move the sheath relative to the reference point;
a sheath lock configured to selectively fix a position of the sheath relative to the reference point;
a primary actuator configured to move the primary electrode in a first direction and in a second direction opposite to the first direction;
a secondary actuator configured to move the secondary electrode in the first direction and in the second direction; and
a control mechanism configured to selectively mechanically engage the first actuator and the second actuator to:
upon the first actuator being moved into at least one first position,
movement of the secondary actuator in either of the first direction
and the secondary direction is automatically blocked by
engagement of the control mechanism with the primary actuator;
upon the second actuator being moved into at least one second position,
movement of the primary actuator in either of the first direction
and the secondary direction is automatically blocked by
engagement of the control mechanism with the secondary actuator; and
lock positions of the primary actuator and the secondary actuator.

11. The system of claim 10, wherein the control mechanism includes an actuator interlock configured to prevent movement of the primary actuator while the secondary electrode is moved independently of the primary electrode to deploy the secondary electrode.

12. The system of claim 11, wherein the actuator interlock is further configured to restrict movement of the secondary actuator within a selected range.

13. The system of claim 11, wherein the actuator interlock is further configured to prevent movement of the secondary actuator while the primary actuator is moved to partially retract the primary electrode in the second direction.

14. The system of claim 10, wherein the control mechanism includes at least one trigger configured to be activated to unlock motion of at least one of the primary actuator and the secondary actuator.

15. The system of claim 10, wherein the control mechanism includes at least one guide channel configured to selectively permit movement of one of the primary actuator and the secondary actuator.

16. The system of claim 15, wherein the guide channel is configured to enable at least one of:
rotating of the primary actuator to unlock motion of the primary actuator;
rotating of the secondary actuator to unlock motion of the secondary actuator;
sliding of the primary actuator to move the primary electrode within a first range of motion; and
sliding of the secondary actuator to move the secondary electrode within a second range of motion.

17. The system of claim 10, further comprising a position indicator configured to indicate a distance of travel of the primary electrode relative to the reference point.

* * * * *